United States Patent
Rolandi et al.

(10) Patent No.: US 10,751,050 B2
(45) Date of Patent: Aug. 25, 2020

(54) MICROSTRUCTURE-BASED WOUND CLOSURE DEVICES

(71) Applicant: University of Washington through its Center for Commercialization, Seattle, WA (US)

(72) Inventors: Marco Rolandi, Seattle, WA (US); Vittorio Ruvolo, Novi Ligure (IT); Ronald J. Berenson, Mercer Island, WA (US); Chase Ruebel, Seattle, WA (US); Jungho Jin, Seattle, WA (US)

(73) Assignee: University of Washington, Seattle, WA (US)

( * ) Notice: Subject to any disclaimer, the term of this patent is extended or adjusted under 35 U.S.C. 154(b) by 219 days.

(21) Appl. No.: 14/408,244

(22) PCT Filed: Jun. 17, 2013

(86) PCT No.: PCT/US2013/046181
§ 371 (c)(1),
(2) Date: Mar. 23, 2015

(87) PCT Pub. No.: WO2013/188884
PCT Pub. Date: Dec. 19, 2013

(65) Prior Publication Data
US 2015/0305739 A1    Oct. 29, 2015

Related U.S. Application Data

(60) Provisional application No. 61/710,246, filed on Oct. 5, 2012, provisional application No. 61/660,561, filed on Jun. 15, 2012.

(51) Int. Cl.
*A61B 17/08*    (2006.01)
*A61M 37/00*    (2006.01)
*A61F 13/00*    (2006.01)

(52) U.S. Cl.
CPC ........ *A61B 17/08* (2013.01); *A61B 2017/081* (2013.01); *A61F 2013/00723* (2013.01);
(Continued)

(58) Field of Classification Search
CPC ..... A61B 17/08; A61B 17/083; A61B 17/085; A61B 17/064; A61B 2017/081;
(Continued)

(56) References Cited

U.S. PATENT DOCUMENTS 3,926,193 A * 12/1975 Hasson ................ A61B 17/085
606/218
4,430,998 A * 2/1984 Harvey ................ A61B 17/085
606/216

(Continued)

FOREIGN PATENT DOCUMENTS

JP    2003533326 A    11/2003
JP    2009545382 A    12/2009
(Continued)

OTHER PUBLICATIONS

Exam Report dated Sep. 2, 2016 in European Application No. 13733182.3, 4 pages.
(Continued)

*Primary Examiner* — Katherine H Schwiker
(74) *Attorney, Agent, or Firm* — Perkins Coie LLP

(57) ABSTRACT

The present invention relates generally to wound closure devices comprising one or more microstructures. The devices are designed such that the microstructures are able to grip the skin or tissue surrounding a wound, optionally closing the wound, or securing the tissue or skin in place. Also provided are wound closure systems that comprise one or more microstructure wound closure devices along with other components, such as protective covers and wound healing therapeutics. A variety of packaging specifications
(Continued)

are disclosed, as is a dispenser apparatus configured to enable simple one-handed application of the wound closure devices. Methods described herein provide for the closure of various wounds with the wound closure devices and systems.

20 Claims, 28 Drawing Sheets

(52) U.S. Cl.
CPC ............... *A61M 2037/0046* (2013.01); *A61M 2037/0061* (2013.01)

(58) Field of Classification Search
CPC ........ A61B 5/150977; A61B 5/150984; A61B 17/0642; A61B 2017/0641; A61B 2017/0647; A61B 2017/086; A61B 2017/1103; A61B 2017/1107; A61B 2017/111; A61B 2017/1139; A61B 2017/1132; A61B 2017/1135; A61B 2017/1142; A61B 2017/06176; A61B 2017/0618; A61B 2017/0412; A61B 2017/00579; A61B 17/11; A61B 17/1146; A61M 37/0015; A61M 2037/0043; A61M 2037/0061; A61M 2037/0053
USPC .......................................... 606/186, 215–221
See application file for complete search history.

(56) References Cited

U.S. PATENT DOCUMENTS

| | | | | |
|---|---|---|---|---|
| 5,047,047 A * | 9/1991 | Yoon | ..................... | A61B 17/083 606/213 |
| 5,234,462 A * | 8/1993 | Pavletic | ............... | A61B 17/085 606/215 |
| 5,531,790 A * | 7/1996 | Frechet | ................... | A61B 90/02 606/1 |
| 2002/0133129 A1 | 9/2002 | Arias et al. | | |
| 2003/0065360 A1 | 4/2003 | Jacobs et al. | | |
| 2003/0074021 A1 * | 4/2003 | Morriss | ................. | A61B 17/064 606/215 |
| 2004/0010276 A1 | 1/2004 | Jacobs et al. | | |
| 2004/0138705 A1 | 7/2004 | Heino et al. | | |
| 2004/0260340 A1 * | 12/2004 | Jacobs | ................. | A61B 17/064 606/213 |
| 2006/0093658 A1 | 5/2006 | Sathyan et al. | | |
| 2007/0021779 A1 * | 1/2007 | Garvin | .................... | A61B 17/08 606/216 |
| 2008/0275409 A1 | 11/2008 | Kane et al. | | |
| 2010/0048744 A1 | 2/2010 | Park et al. | | |
| 2012/0221044 A1 * | 8/2012 | Archibald | ............... | A61B 17/08 606/214 |

FOREIGN PATENT DOCUMENTS

| | | | | |
|---|---|---|---|---|
| JP | WO 2011016230 A1 * | 2/2011 | ........ | A61M 37/0015 |
| WO | 02/072189 A2 | 9/2002 | | |
| WO | 2006124671 A2 | 11/2006 | | |
| WO | 2007/127976 A2 | 11/2007 | | |
| WO | 2008020632 A1 | 2/2008 | | |
| WO | WO 2010124712 A1 * | 11/2010 | ........... | A61B 17/085 |
| WO | 2011067297 A1 | 6/2011 | | |
| WO | 2011135531 A2 | 11/2011 | | |
| WO | 2013188884 | 12/2013 | | |

OTHER PUBLICATIONS

Written Opinion dated Jun. 29, 2016 in Singapore Application No. 11201408221Y, 6 pages.
Search Report dated Oct. 28, 2015 in New Zealand Application No. 702677, 2 pages.
Search Report and Written Opinion dated Nov. 19, 2015 in Singapore Application No. 11201408221Y, 10 pages.
International Search Report and Written Opinion dated Aug. 13, 2013 in International Application No. PCT/US2013/046181, 9 pages.
Notification of Transmittal of the International Search Report and the Written Opinion dated Aug. 13, 2013, issued in corresponding International Application No. PCT/US2013/046181, filed Jun. 17, 2013, 9 pages.
Examination Report dated Nov. 7, 2016 in corresponding Australian Patent Application No. 2013273965, 3 pages.
Examination Report dated Jun. 1, 2017 in Australian Application No. 2013273965, 4 pages.
Written Opinion dated May 18, 2017 in Singapore Application No. 11201408221Y, 6 pages.
Office Action dated Mar. 14, 2017 in Japanese Patent Application No. 2015-517482, 7 pages.
Francesko et al., "Chitin, Chitosan and Derivatives for Wound Healing and Tissue Engineering," Adv Biochem Engin/Biotechnol (2011) 125: 1-27.
Lawton et al., "Novel Haemostatic Dressings," JR Army Med Corps, vol. 155(4): 309-314.
Lee et al., "β-Chitin-Based Wound Dressing Containing Silver Sulfurdiazine," Journal of Materials Science: Materials in Medicine, vol. 11 (2000) pp. 817-823.
Mahdavi et al., "A Biodegradable and Biocompatible Gecko-Inspired Tissue Adhesive," Proceedings of the National Academy of Sciences, (2008) vol. 105(7): pp. 2307-2312.
Sugamori et al., "Local Hemostatic Effects of Microcrystalline Partially Deacetylated Chitin Hydrochloride," J Biomed Mater Res, vol. 49 (2000) pp. 225-232.
Yusof et al., "Preparation and Characterization of Chitin Beads as a Wound Dressing Precursor," Journal of Biomedical Materials Research, vol. 54 (2001) pp. 59-68.
Zhong et al., "A Chitin Nanofiber Ink for Airbrushing, Replica Molding, and Microcontact Printing of Self-Assembled Macro-, Micro-, and Nanostructures," Adv Materials (2011) 23, pp. 4776-4781.
Zhong et al., "A Facile Bottom-Up Route to Self-Assembled Biogenic Chitin Nanofibers," Soft Matter (2010) vol. 6(21), pp. 5298-5301.
Examination Report in European Patent Application No. 13733182.3, dated Jul. 11, 2017, 5 pages.
"Japanese Application Serial No. 2015-517482, Examiners Decision of Final Refusal dated Sep. 11, 2018", W English Translation, 7 pgs.
"International Application Serial No. PCT US2013 046181, International Preliminary Report on Patentability dated Dec. 16, 2014", 6 pgs.
"International Application Serial No. PCT US2013 046181, International Preliminary Report on Patentability dated Dec. 24, 2014", 7 pgs.
Exam Report in Canadian Patent Application No. 2,875,227, dated Feb. 21, 2019, 4 pages.
Extended Search Report in European Patent Application No. 19174754.2, dated Oct. 21, 2019, 204 pages.
Examination Report dated Jan. 7, 2020 in India Patent Application No. 2939/KOLNP/2014, 6 pages.

* cited by examiner

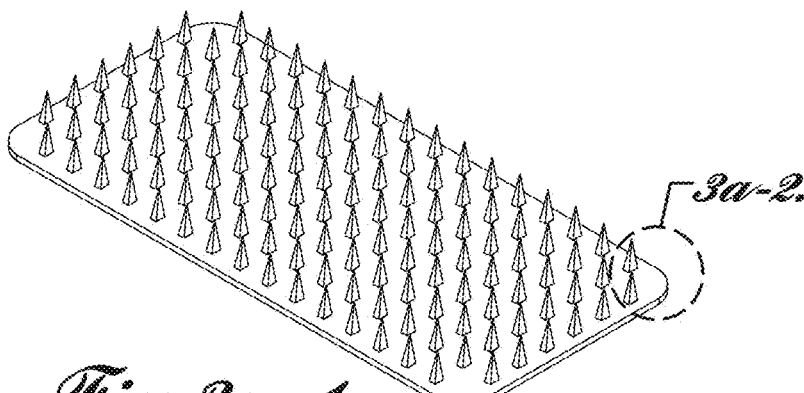
Fig.3a-1.
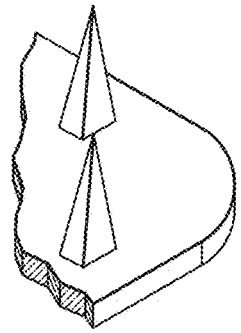
Fig.3a-2.
100 MICRONEEDLES /CM^2
8 NEEDLES X 17 NEEDLE ARRAY
(MINUS CORNERS) 132 TOTAL NEEDLES
*FOR 104-2A 177 NEEDLES / CM^2
10 X 23(MINUS CORNERS) 226 TOTAL NEEDLES
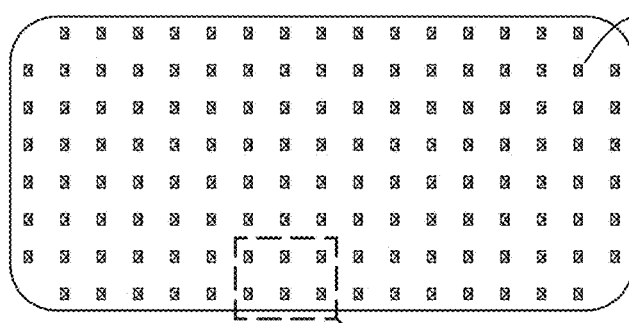
Fig.3a-3.
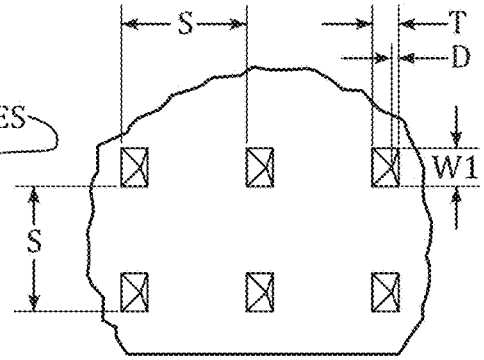
Fig.3a-4.
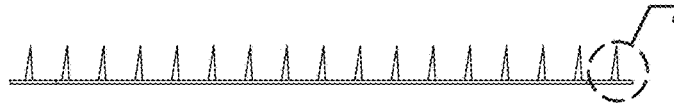
Fig.3a-5.
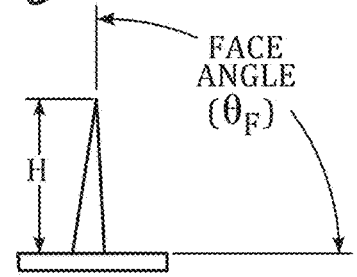
Fig.3a-6.
| PART NUMBER | TYPE | HEIGHT (H) | WIDTH (W1) | WIDTH (W2) | THICKNESS (T) | TIP OFFSET (D) | SPACING (S) | FACE ANGLE |
|---|---|---|---|---|---|---|---|---|
| 104-1 | MICRONEEDLE 1MN | 700 | 200 | NA | 125 | 25 | 1 | 92.1 |
| 104-2 | MICRONEEDLE 2MN | 700 | 250 | NA | 150 | 50 | 1 | 94.1 |
| 104-2A | MICRONEEDLE 2MN | 700 | 250 | NA | 150 | 50 | 0.75 | 94.1 |
| 104-3 | MICRONEEDLE 3MN | 950 | 300 | NA | 200 | 50 | 1 | 93 |
| DIMENSIONS ARE IN MILLIMETERS. TOLERANCES: .X +/- .1; .XX +/-.05; ANGULAR +/-.5 DEG ||||||||||
Fig.3b.

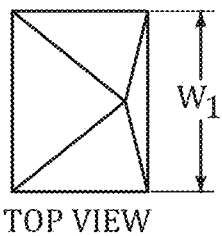
TOP VIEW
Fig.4a.
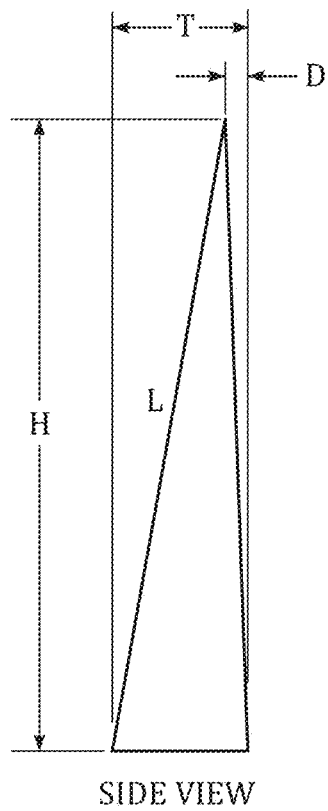
SIDE VIEW
Fig.4b.
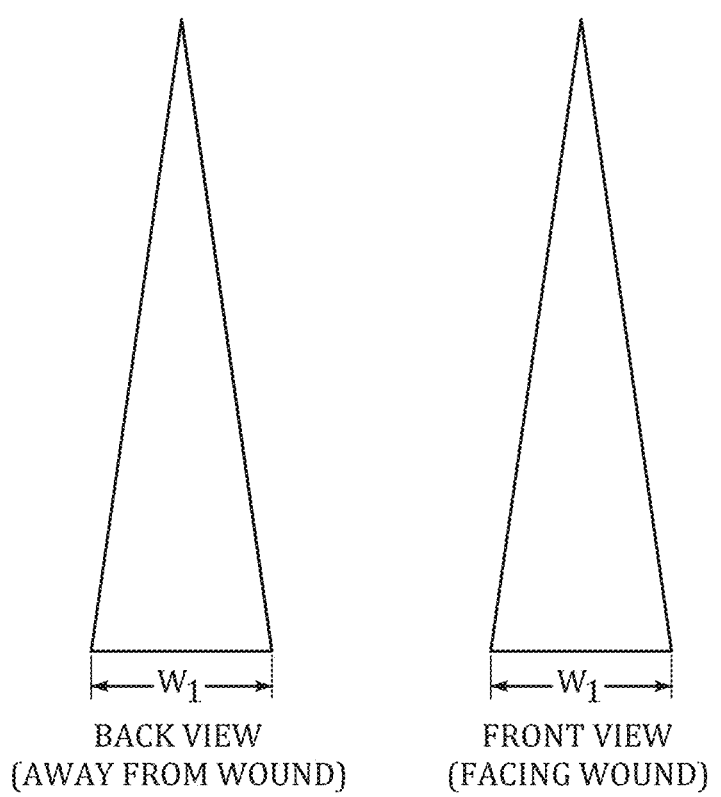
BACK VIEW
(AWAY FROM WOUND)
Fig.4c.
FRONT VIEW
(FACING WOUND)
Fig.4d.

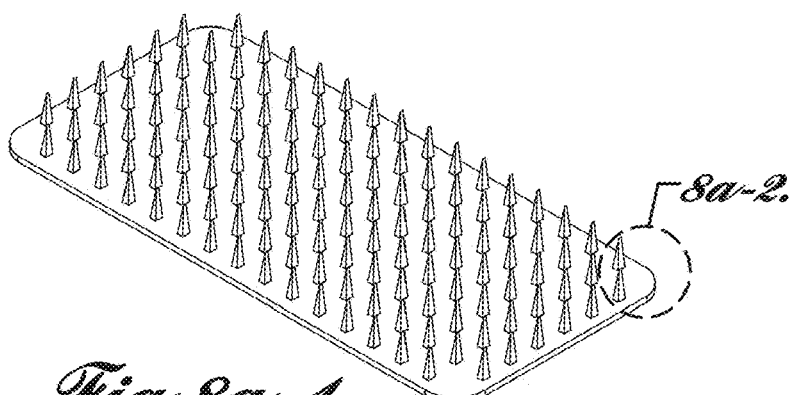

*Fig. 8a-1.*

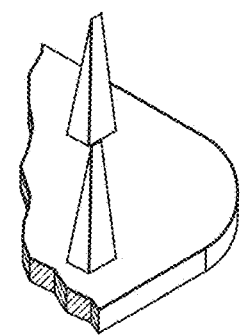

*Fig. 8a-2.*

100 MICRONEEDLES /CM^2
8 NEEDLES X 17 NEEDLE ARRAY
(MINUS CORNERS) 132 TOTAL NEEDLES
*FOR 104-5A 177 NEEDLES / CM^2
10 X 23(MINUS CORNERS)
226 TOTAL NEEDLES

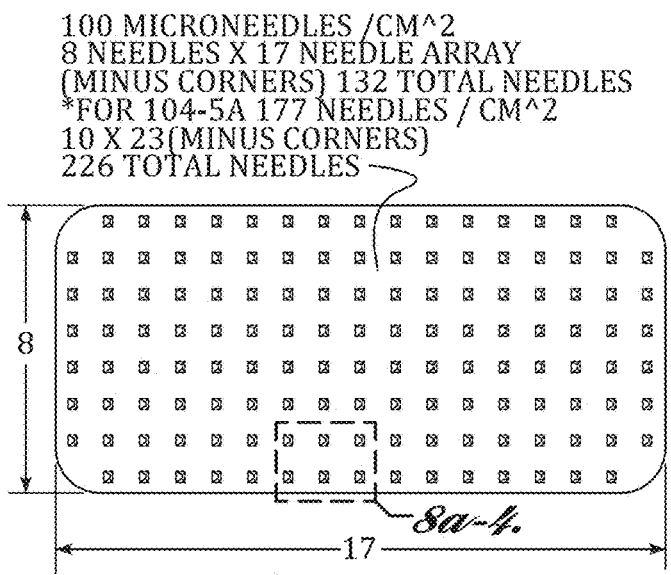

*Fig. 8a-3.*

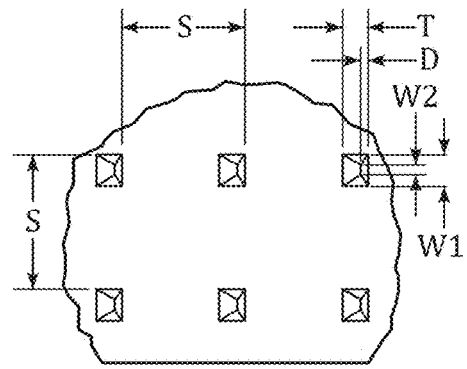

*Fig. 8a-4.*

*Fig. 8a-5.*

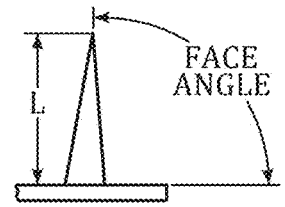

*Fig. 8a-6.*

MICROSTRUCTURE BASED WOUND CLOSURE DEVICES

| PART NUMBER | TYPE | LENGTH (L) | WIDTH (W1) | WIDTH (W2) | THICKNESS (T) | TIP OFFSET (D) | SPACING (S) | FACE ANGLE |
|---|---|---|---|---|---|---|---|---|
| 104-4 | MICROBLADE 1MB | 700 | 200 | 50 | 125 | 25 | 1 | 92.1 |
| 104-5 | MICROBLADE 2MB | 700 | 250 | 50 | 150 | 50 | 1 | 94.1 |
| 104-5A | MICROBLADE 2MB | 700 | 250 | 50 | 150 | 50 | 0.75 | 94.1 |
| 104-6 | MICROBLADE 3MB | 950 | 300 | NA | 200 | 50 | 1 | 93 |

DIMENSIONS ARE IN MILLIMETERS. TOLERANCES: .X +/- .1; .XX +/- .05; ANGULAR +/- .5 DEG

*Fig. 8b.*

TOP VIEW h = 700μm
d1 = 125μm
d2 = 25μm
w1 = 200μm
w2 = 50μm

SIDE VIEW

BACK VIEW
(AWAY FROM WOUND)

FRONT VIEW
(FACING WOUND)

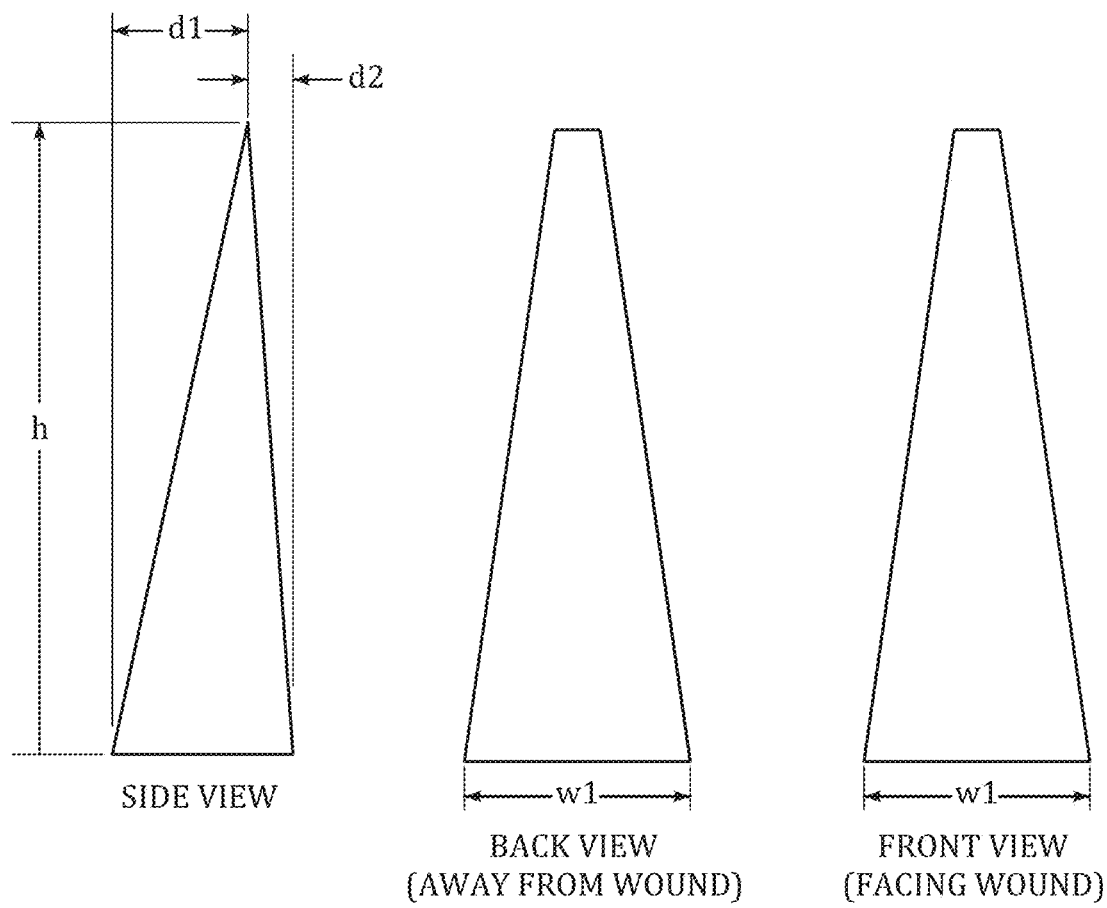

TOP VIEW h = 950μm
d1 = 200μm
d2 = 50μm
w1 = 300μm
w2 = 75μm

SIDE VIEW

BACK VIEW
(AWAY FROM WOUND)

FRONT VIEW
(FACING WOUND)

1000 MICRON LENGTH
250 MICRON BASE
20 MICRON TIP
24 DEGREE ANGLE
MICRONEEDLE

NON-STRETCH SILICONE
STRETCH SILICONE
2.0"
0.5"
400 MICRONEEDLE/CM^2 ARRAY

OPTIONAL COATING
SILICONE SUBSTRATE

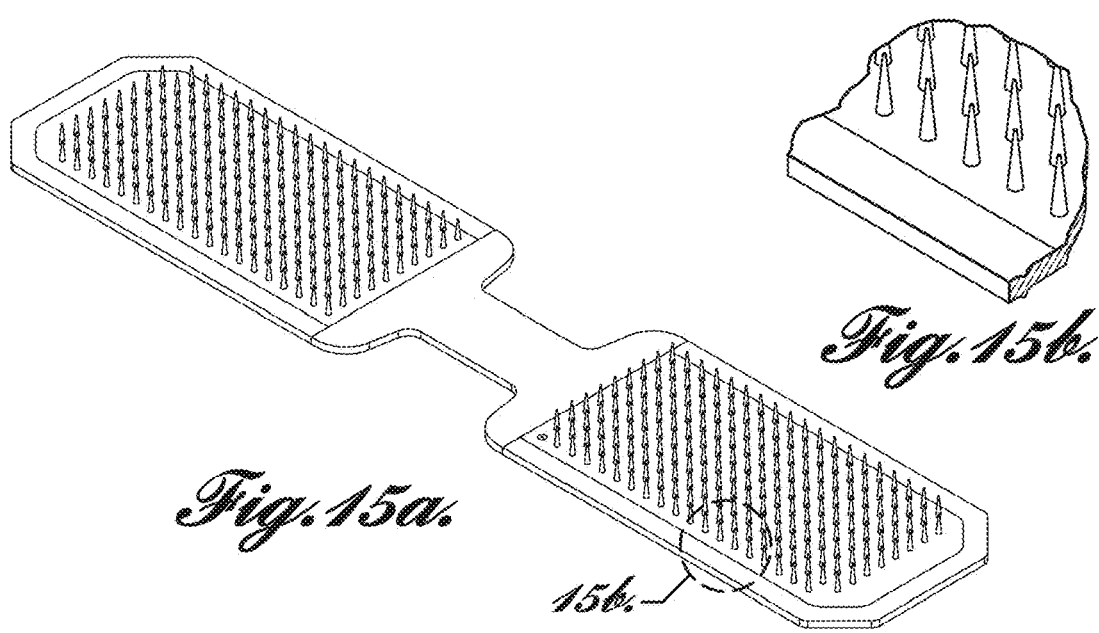
Fig.15a.
Fig.15b.
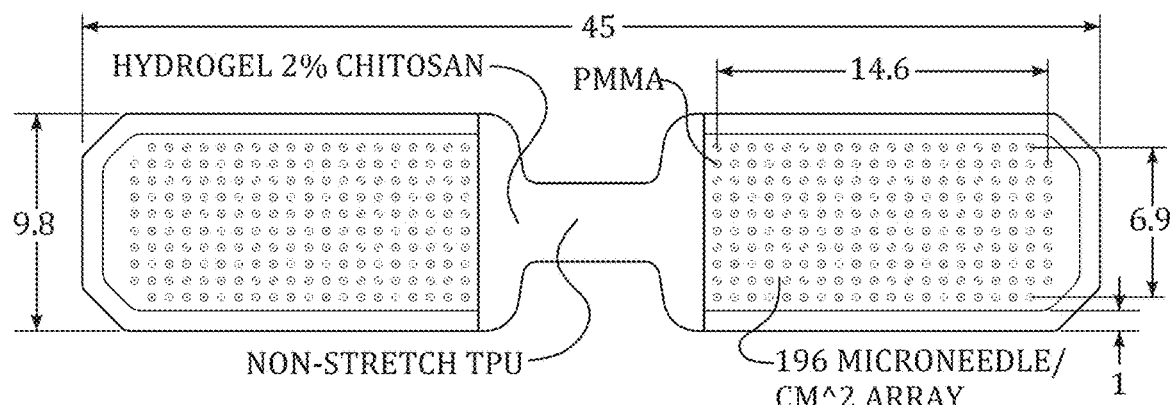
Fig.15c.
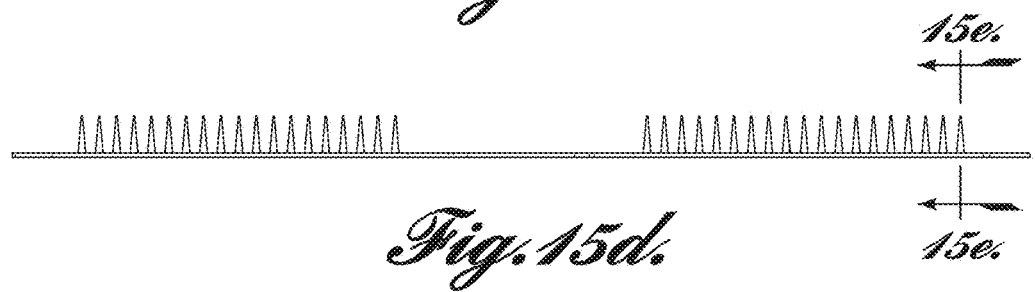
Fig.15d.
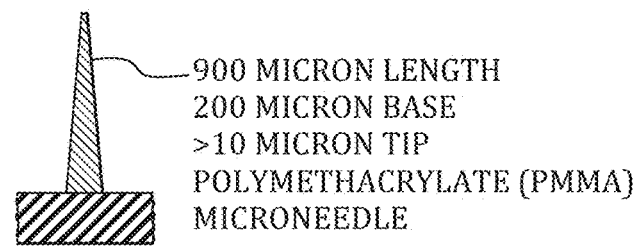
Fig.15e.

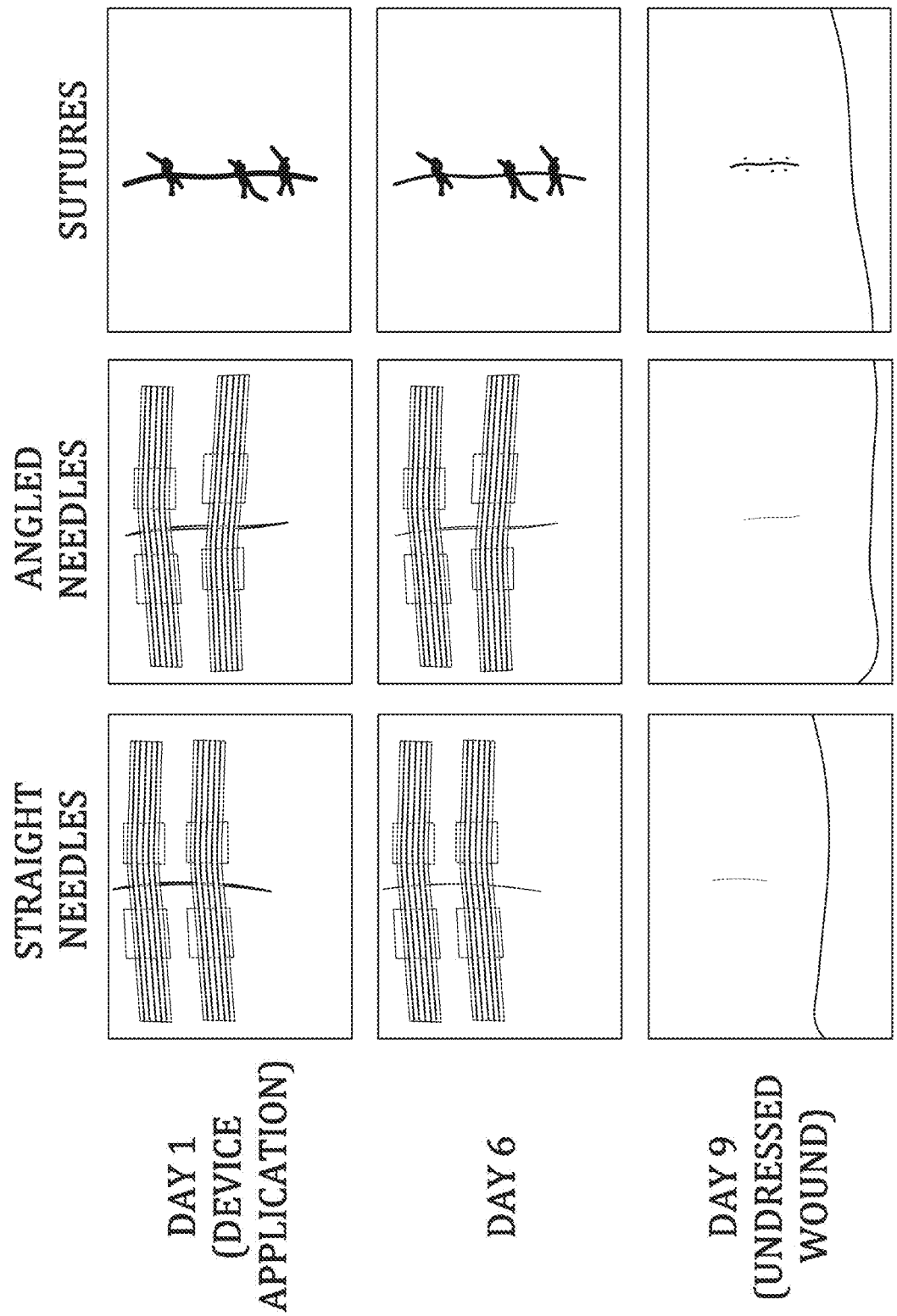

DAY 9 UNDRESSED WOUND
STRAIGHT NEEDLES

DAY 9 UNDRESSED WOUND
ANGLED NEEDLES

DAY 9 UNDRESSED WOUND
SUTURES

MICROSTRUCTURE-BASED WOUND CLOSURE DEVICES

CROSS REFERENCE TO RELATED APPLICATIONS

This application claims priority to U.S. Provisional Application No. 61/660,561, filed on Jun. 15, 2012, and U.S. Provisional Application No. 61/710,246, filed on Oct. 5, 2012, both of which are herein incorporated by reference in their entirety.

BACKGROUND

Compositions and methods for wound closure are known in the art. Depending on the severity of the wound, the most common treatments range from simple adhesive-based, over the counter products, such as BAND-AIDs®, butterfly strips, and Steri-Strips, to more specialized products, such as sutures and staples. Proper application of sutures and staples requires a trained specialist; and although these techniques can be quite effective at closing wounds, they are invasive, and painful procedures that frequently require the use of an anesthetic. Furthermore, these procedures can leave unsightly scars, both from the secondary insertion holes as well as spacing and depth variations that result in varying tensions applied to the laceration or surgical incision between the suturing points and intervening spaces. Moreover, these skin closure techniques necessitate follow-up visits to a hospital or doctor's office for removal of sutures and staples; a particularly sub-optimal feature in the event of an infection, wherein it is often necessary to remove the sutures such that the wound may be reopened and cleaned. Additionally, simply covering the wound with a bandage, such as a BAND-AID® is often not sufficient to close more severe or deeper wounds; the adhesives used to attach these devices and the Steri-Strips and butterfly strips are not adequate to close these wounds without detaching or creep. Skin moisture adds to the problem by further reducing adherence of the adhesive based bandage, and may lead to their premature release from the skin and wound site before closure of the wound and proper healing. Also, the adhesive can induce symptomatic allergic and inflammatory reactions.

The present invention relates to improved wound closure devices that in some embodiments enable simple, minimally invasive wound closure, without the need for follow-up care. The devices are easily applied and removed, often with little to no pain, thus obviating reliance on trained specialists for their application and removal. In some embodiments, the devices of the present invention can achieve wound closure without resulting in the aforementioned closure-induced scarring that can occur with the prior art techniques. Furthermore, in certain embodiments the wound closure devices disclosed herein may be appropriately secured to a wound without the need for adhesive, thus avoiding potential allergic complications.

SUMMARY

The present invention relates generally to wound closure devices comprising one or more microstructures. In some embodiments, the microstructures are capable of penetrating into skin or tissue. In some embodiments, the device comprises a plurality of microstructures. The microstructures are fabricated on, affixed to, or connected to a base or backing that may optionally be made out of the same material as the microstructures, or a different material. In some embodiments, the base or backing is flexible, stretchable, or both flexible and stretchable. In some embodiments, the microstructures are fashioned into one or more microstructure arrays, upon a base. In particular embodiments, the wound closure devices comprise at least two microstructure arrays, each array being patterned upon a base (said base optionally comprising one or more arrays), and said arrays optionally being affixed to a backing, according to the present disclosure. In such embodiments, at least one of said arrays is capable of securing the device on one side of a wound, and at least one other of said arrays is capable of securing the device on another side of the wound. In other particular embodiments, the wound closure devices comprise only one microstructure array, said array fabricated on a base portion, and said base portion optionally being affixed to a backing. In such embodiments, at least one of the microstructures comprised in the array is capable of securing the device on one side of the wound and at least one other microstructure comprised on the array is capable of securing the device on the other side of the wound.

Devices of the present invention are useful wound closure products, capable of performing a variety functions (e.g., protecting a wound from its surrounding environment, preventing infection, closing a wound, and increasing the delivery of therapeutic compounds through skin).

In particular embodiments, the devices are specifically designed such that their application does not result in inflammation. In some embodiments, the wound closure devices disclosed herein induce little to no inflammation and result in little to no additional scarring (e.g., the railroad track effect that results from staples and sutures). In some embodiments, the devices of the present invention have the important advantage of being easily applied and removed without the need for extensive training or specialized equipment. Furthermore, in certain embodiments, the devices are secured to the skin of a patient in the absence of an adhesive, avoiding allergic reactions caused by adhesives. Thus, the wound closure devices of the present invention provide an attractive and versatile alternative to traditional wound closure devices.

In some embodiments, the wound closure devices of the present invention comprise a flexible and/or stretchable backing upon which one or more microstructures are affixed. In some embodiments, one or more microstructure arrays are affixed to a flexible and/or stretchable backing. The flexibility and/or stretchability of the backing may be uniform throughout; or, optionally one or both of these properties may vary across, or along, the device, a microstructure array, or between two or more microstructure arrays.

In some embodiments, the wound closure device of the present invention comprises one or more microstructure arrays, optionally affixed to a backing, such that at least one microstructure array is capable of penetrating into skin or tissues. In particular embodiments, such devices comprise microstructures that penetrate into the superficial epidermis, epidermis, superficial dermis, or deep dermis. In other embodiments, the wound closure device comprises a plurality of microstructure arrays such that the microstructures do not penetrate the skin or tissue surface.

In certain embodiments, the wound closure devices may comprise at least two microstructure arrays as described herein, said arrays being optionally affixed to a backing. In some particular embodiments, the wound closure devices may comprise two or more arrays optionally affixed to a backing, as described herein, such that at least two arrays are separated by space with no arrays. This space, referred to throughout as an "isthmus", may be of any suitable length, width, or shape, and may be comprised of any suitable material. In some embodiments, the isthmus ranges from 1 mm in length to 15 mm in length. In certain embodiments the isthmus is not stretchable, while in other embodiments this space is stretchable.

In some embodiments, the wound closure devices of the present invention comprise one or more microstructures at an angle with respect to a base or backing. In one such embodiment, microstructures are angled in a way to translate the longitudinal tension from the skin pulling the wound apart along the device into a force that pushes the device downward onto the skin, thus, e.g., effectively anchoring the device onto the skin. Wound closure devices of the present invention may in some embodiments also include microstructure arrays comprising microstructures with variable angles relative to a base, e.g., wherein at least two microstructures comprised in a single array extend from a base at different angles than one another. A non-limiting example of such an array, e.g., is one that comprises both straight microstructures (i.e., protruding from a base at a 90° angle) and angled microstructures (e.g., protruding from the base at an angle less than 90°, such as 51°). Additionally, individual microstructure length can vary based upon its position in a microstructure array, or based upon its position on a wound closure device.

In various embodiments, the microstructure arrays of the present invention are fashioned or affixed upon a base in a particular shape or pattern, said shape or pattern optionally being of any shape or geometry described herein. In some embodiments, such patterned arrays are further affixed to a backing (e.g., a flexible and/or stretchable backing); while in other embodiments they are not. In some certain embodiments, arrays according to the present disclosure are fashioned or affixed on a base portion, optionally at an angle, wherein the arrays are patterned in a rectangular shape, said arrays comprising microstructures of any shape or geometry described herein; and said arrays optionally being affixed to a backing.

In some certain embodiments, the wound closure devices of the present invention comprise a plurality of microstructure arrays that are capable of penetrating or grasping skin or tissue; said arrays either being affixed to a flexible and stretchable backing, or being comprised on a single flexible and stretchable base, in a configuration such that at least two arrays are separated by an isthmus, as described herein; and said devices having the capability of being stretched across a wound and secured on either side via the traction or grip of the microstructures. Accordingly, such a device may be applied by first securing at least one microstructure array to the skin or tissue on one side of the wound, then stretching the device across the wound so as to secure another microstructure array to the skin or tissue on the other side of the wound. In such a manner, the retractile force of the stretched device can in some embodiments pull and/or secure the wound closed, thus further promoting healing; while in other embodiments such a force stabilizes the position of the device on the skin, but does not directly induce the closure of the wound.

In other certain embodiments, the wound closure devices of the present invention comprise a plurality of microstructure arrays that are capable of penetrating or grasping skin or tissue; said arrays either being affixed to a non-stretchable backing, or being comprised on a single non-stretchable base, in a configuration such that at least two arrays are separated by an isthmus, as described herein. In such embodiments, the devices are useful e.g., for securing tissue in place. Non-limiting examples of how this type of device may be used include the securing of a wound closed that has already been closed by some other method e.g., via suturing, or with forceps.

The wound closure devices of the present invention may optionally be covered to further protect the lesion from the surrounding environment, and to assist in maintaining proper securing of the device as placed. Covers may optionally comprise adhesive.

The wound closure devices of the present invention may comprise microstructures of various shapes, sizes, and structures. Accordingly, in some embodiments, one or more microstructure arrays are fashioned, optionally upon a base, said microstructures optionally comprising a variety of shapes, sizes, structures, and geometries; and said arrays optionally being affixed to a backing Certain embodiments provide for microstructures selected from the group consisting of microneedles, microblades, microanchors, microfishscale, micropillars, microhairs, and combinations thereof. The wound closure devices of the present invention may comprise microstructure arrays comprising any density of microstructures. In some embodiments, the density of microstructures comprised in an individual array varies from 2 microstructure per array, to more than 1000 microstructures per array. In certain embodiments, the arrays comprise a density of microstructures arrays varying from 1 microstructure per $cm^2$ to 1000 microstructures per $cm^2$. Accordingly, in various embodiments the array pitch is varied from approximately 30 μm to more than 1 cm.

The microstructures comprised in the wound closure devices disclosed herein may be made of any material or mixture of materials. In some embodiments, the material is a natural material, or a mixture of natural materials; while in other embodiments it is a synthetic material, or a mixture of synthetic materials. Still other embodiments provide for microstructures, according to the present disclosure, comprising mixtures of one or more synthetic materials and one or more natural materials. In particular embodiments, microstructures are made of a material selected from a polymer, a metal, a biomaterial, and a combination thereof. In some embodiments, a microstructure of the present invention is comprised of nanostructures, (e.g., nanofibers). In some embodiments, the microstructures are coated with nanostructures (e.g., nanofibers). In some embodiments the microstructures are comprised of, or consist essentially of biodegradable materials. In some embodiments this is very important to ensure complications, such as inflammation, tissue damage, and infection, due to broken needles do not occur. In other embodiments, the microstructures do not comprise biodegradable materials. In other embodiments the microstructures comprise biodegradable materials and non-biodegradable materials.

In certain embodiments, microstructures of the present invention are comprised of a polymer selected from poly (methyl methacrylate) (PMMA), silicon, and chitin.

The wound closure devices of the present invention may also optionally comprise other components such as, but not limited to, nanostructures (e.g., nanostructure arrays or nanofibers); bioactive compounds (e.g., drugs, therapeutics, hydrogels, healing substances, and combinations thereof), etc. In some particular embodiments, the wound closure devices further comprise chitin (e.g., chitin nanofibers). In other embodiments the wound closure devices of the present invention further comprise a hydrogel.

Some embodiments of the present invention provide for microstructure arrays designed to penetrate the skin to enable delivery of drugs or other therapeutic agents. In one particular embodiment, the microstructures are long enough to penetrate the skin, but not deep enough to reach nerve endings that cause pain. Some embodiments can incorporate both microstructures coated with drugs as well as microstructures with open internal structure in which drugs can be incorporated.

In some embodiments, the wound closure device is applied to the skin without the use of an applicator or instrument. In other embodiments, the wound closure device is applied to the skin using an applicator or instrument, such as a forceps or tweezers, to hold the device, or to provide assistance in delivering force during the application of the device over the wound.

In some embodiments, the wound closure devices of the present invention may optionally include adhesive to assist in the application and optionally in the stabilization of the device upon the skin. Adhesive may be present on the device in any suitable location. In some embodiments, the wound closure devices comprise an adhesive backing, or a base that comprises adhesive.

In some embodiments, adhesive is provided to the device on a tab that is attached to at least one end of the device. The tab is not part of the device but is attached to the device in order to enable adhesion. The device actually remains on the wound, while a tab can be removed. The tabs can be added to one or both distal ends of the device. In other embodiments, adhesive is provided on a tab that is attached to at least one side of the device.

Still other embodiments provide for devices as described herein comprising adhesive tabs positioned on at least one end and at least one side of the device. These adhesive tabs may be any length, optionally being shorter, longer, or equal in length to any one or more sides of the device. Furthermore, some embodiments provide for adhesive tabs that are removable, e.g., adhesive tabs comprising perforations that enable the adhesive portion to be easily torn off by hand. In some embodiments the adhesive is any medical grade adhesive, such as, e.g., an acrylate (such as, e.g., is used on the Steri-Strips or Steri-Strip S isthmus), or hydrogel-based adhesives that can stick to wet surfaces (e.g., Polyethylene glycol (PEG) hydrogel). In other embodiments the adhesive component comprises nanostructures that provide glueless adhesion. Adhesion of a device to skin or tissue induced by such adhesives may last for as little as a minute (e.g., when the adhesive is utilized to help apply the device) or such adhesion may last for 10 days or more. Accordingly, adhesion to the skin or tissue as the result of an adhesive may last for 5 min, 10 min, 15 min, 20 min, 30 min, 60 min, 2 hr, 4 hr, 6 hr, 12 hr, 24 hr, 2 days, 4 days, 6 days, 8 days, 10 days, or more, including all integers (31 min, 32 min, 33 min, 13 hr, 14 hr, 15 hr, 3 day, 5 days, etc.) and ranges (1 min-10 days, 1 min-1 hr, 5 min-20 min, etc.) of the adhesion durations set forth herein.

Embodiments of the present invention provide for wound closure devices as disclosed herein that are available in a single package comprising only one such device, as well as packages comprising a plurality of said devices. In one embodiment, the wound closure devices are in the form of a roll, said roll optionally comprising individually wrapped wound closure devices, or alternatively a plurality of wound closure devices that are not individually wrapped. In particular embodiments, the devices are sterile, and are packaged so as to maintain such sterility until being opened.

The present invention furthermore provides for hand held dispensers that allow for easy application of the wound closure devices of the present invention. In one embodiment, the dispenser is a roll-on, handheld dispenser, optionally enabling rapid single hand operation.

Some embodiments of the present invention further provide for a kit comprising a wound closure system. Wound closure systems comprise one or more wound closure devices, as described herein, as well as other optional components such as, e.g., one or more cover (optionally comprising adhesive) to be applied over the wound closure device; one or more containers (e.g., bottles, pouches, packets, tubes) comprising a drug or therapeutic which can optionally be applied to the wound prior to the application of the device; cleansing and/or sterilization means (e.g., antiseptics, antibiotics, sterile saline); analgesics (e.g., Benzocaine or Lidocaine); and instructions for using the various components of the wound closure system singly, or in combination.

The wound closure devices of the present invention are suitable for treating internal and external wounds alike. In some embodiments, the wound closure devices are applied to a subject's skin; and in other embodiments the wound closure devices are applied to a subject's tissue (e.g., internal tissue). Accordingly, the wound closure devices of the present invention find utility in a variety of settings including, but not limited to, the treatment of wounds in urgent care settings (e.g., surgery or trauma centers including emergency rooms, operating rooms, ambulances battlefields, and sites of accidents); in hospitals and clinics; in over the counter settings (e.g., for use at home).

In some embodiments, the wound closure devices of the present invention have alternative utilities. For example, the devices disclosed herein may also be used in cosmetics, wherein microstructures, as described herein, may be used to penetrate the skin producing skin rejuvenation via acute injury resulting in stimulating the dermis and collagen formation inducing effects achieved with cosmetic laser procedures and skin rollers made of microneedles. This achieves improvement in the appearance of the skin by reducing wrinkles and increasing skin volume. In contrast to cosmetic laser procedures, application of the wound closure devices do not produce symptomatic inflammation resulting in pain, redness, swelling and temporary disfigurement; symptoms which can present for up to a few days after the laser procedure. In contrast to rollers made of microneedles, the wound closure devices can be applied to regions of the skin that are not easily accessible to microneedles, such as between the nose and mouth. In addition, our wound closure devices can be applied and left in place overnight or for days potentially providing more stimulation to the dermis than is achieved with short-term treatment with a microneedle roller. Finally, the wound closure device generates more uniform distribution of holes in the skin than can be achieved with a microneedle roller which is rolled onto the skin surface.

BRIEF DESCRIPTION OF THE DRAWINGS

FIG. 1a: A master of the desired dimensions is made with a metal, silicon, or a polymer via micromachining, microlithography, etching, laser cutting, or a combination thereof. FIG. 1b: The master is replicated using a polymeric material, for example silicone, to form a mold. FIG. 1c: The mold is separated from the master. FIG. 1d: The mold is filled with a solution or a melt of the microstructure material (e.g., by drop casting or spraying). FIG.

1e: The microstructure material is solidified (e.g., cured or dried). FIG. 1f: The microstructures are separated from the mold.

FIGS. 3a-1 to 3a-6 schematically illustrate examples of microneedles as part of an array of microneedles specifically designed for wound closure. Note the asymmetric microneedle shape designed to avoid the microneedle lifting out of the skin when tension is applied to, or occurs on, the wound. FIG. 3b is a table with exemplary microneedle dimensions.

FIGS. 4a to 4d schematically illustrate a microneedle.

FIGS. 8a-1 to 8a-6 schematically illustrate examples of microblades as part of an array of microblades specifically designed for wound closure. Note the asymmetric microblades shape designed to avoid the microblades lifting out of the skin when tension is applied to, or occurs on, the wound. FIG. 8b is a table with exemplary microblade dimensions.

FIGS. 10a to 10d schematically illustrate a microblade of type 2 MB (one of the examples from FIG. 8b).

FIGS. 15a to 15e show schematic drawings of an exemplary device made of a polyurethane backing, with two PMMA microneedle arrays comprising medium density needles. Note the narrow isthmus, the option of including adhesive surrounding the needle arrays, and the option of adding chitosan hydrogel on the isthmus.

(FIG. 17a) shows a device comprising a polyurethane backing, with a polyester filament as an isthmus. The microstructures are spaced at a 1 mm pitch. (FIG. 17b) shows a device which comprises a backing and isthmus that are both made of polyester. The microstructures are at a uniform pitch of 1.5 mm. (FIG. 17c) shows a device comprising a backing and isthmus both made of a paper/fiber mixture with added polyester filament supports for strength. The microstructures are at a uniform pitch of 1.5 mm.

(FIG. 22a) shows a schematic of the size of the wounds and their locations on the porcine. (FIG. 22b) shows a photograph of the animal prior to wound creation, with numbers placed near the incision sites. (FIG. 22c) shows a representative example of one of the wounds, prior to closure.

FIG. 23 shows results of the preclinical study described in FIGS. 22a to 22c (see Example 4). Two wounds were closed with microstructure array wound closure devices as described herein, and one wound was closed with sutures. Wounds were observed for 12 days, and photographs from Day 0 (before wound closure), Day 1 (one day after wound closure), Day 6, and Day 9 (undressed wound—i.e. devices and covers removed from wound) are shown. On Day 9, no abnormalities were observed on or around the wounds treated with the microstructure array closure devices, however the wound closed with sutures showed both inflammation and erythema (Draize Score of 2 on scale of 0-4).

DETAILED DESCRIPTION

Figure 1A:
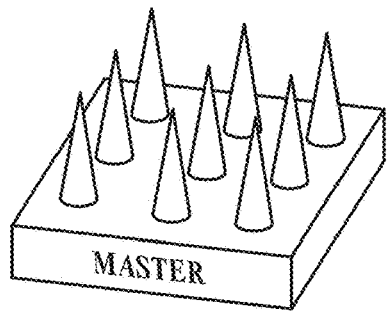
FIGS. 1a to 1f show a schematic representing a representative replica molding process for fabrication of microneedles.
Figure 1B:
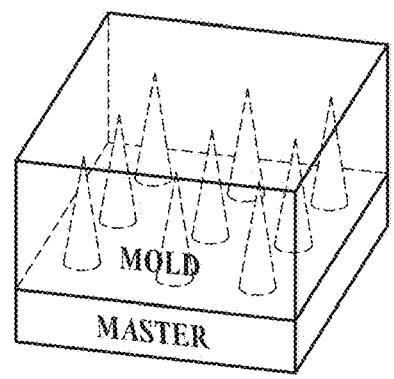
Figure 1C:
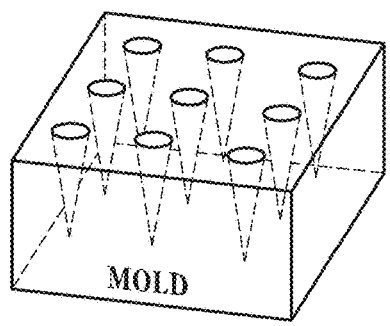
Figure 1D:
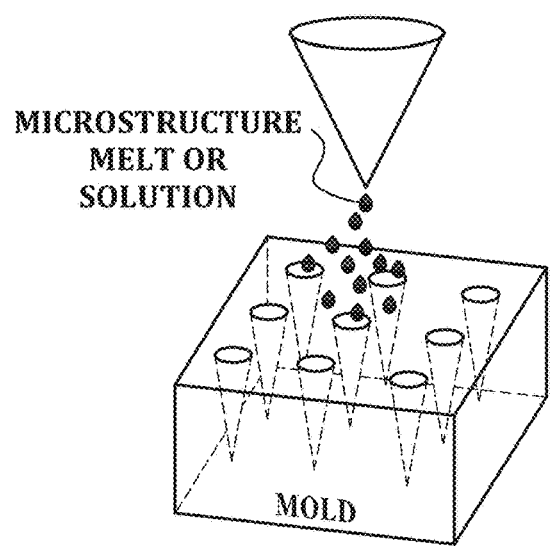
Figure 1E:
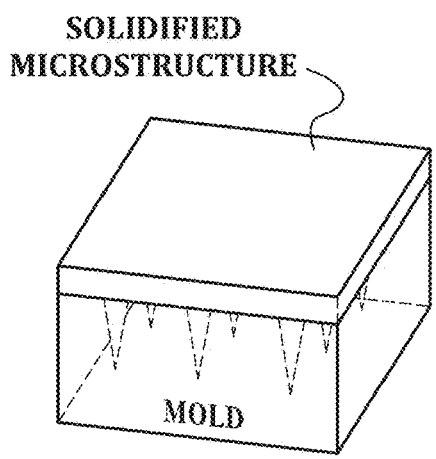
Figure 1F:
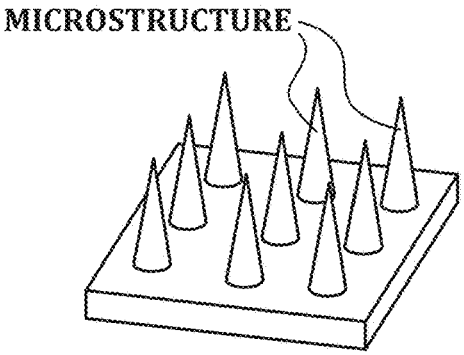

The particulars shown herein are by way of example and for purposes of illustrative discussion of the preferred embodiments of the present invention only, and they are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and Abbreviations

The terminology used herein is for the purpose of describing particular embodiments only, and is not intended to limit the scope of the present invention, which will be limited only by the appended claims. Unless defined otherwise, all technical and scientific terms used herein have the same meaning as commonly understood by one of ordinary skill in the art to which this invention belongs. As used in the specification and appended claims, unless specified to the contrary, the following terms have the meaning indicated.

As used herein and unless otherwise indicated, the terms "a" and "an" are taken to mean "one", "at least one" or "one or more". Unless otherwise required by context, singular terms used herein shall include pluralities and plural terms shall include the singular.

Reference to the term "e.g." is intended to mean "e.g., but not limited to" and thus it should be understood that whatever follows is merely an example of a particular embodiment, but should in no way be construed as being a limiting example. Unless otherwise indicated, use of "e.g." is intended to explicitly indicate that other embodiments have been contemplated and are encompassed by the present invention.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In any embodiment discussed in the context of a numerical value used in conjunction with the term "about," it is specifically contemplated that the term about can be omitted.

Unless the context requires otherwise, throughout the present specification and claims, the word "comprise" and variations thereof, such as, "comprises" and "comprising" are to be construed in an open, inclusive sense, that is as "including, but not limited to".

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Reference throughout this specification to "one embodiment" or "an embodiment" or "some embodiments" or "certain embodiments" mean that a particular feature, structure or characteristic described in connection with the embodiment is included in at least one embodiment of the present invention. Thus, the appearances of the phrases "in one embodiment" or "in an embodiment" or "in certain embodiments" in various places throughout this specification are not necessarily all referring to the same embodiment. Furthermore, the particular features, structures, or characteristics may be combined in any suitable manner in one or more embodiments.

"Optional" or "optionally" means that the subsequently described event of circumstances may or may not occur, and that the description includes instances where said event or circumstance occurs and instances in which it does not.

"Substantially" or "essentially" means nearly totally or completely, for instance, 95% or greater of some given quantity.

As used herein, the term "wound closure device" as used generally means a device used for closing a wound, covering a wound, protecting a wound, a wound dressing, a bandage, etc.

As used herein, the term "wound" means an injury to tissue or skin caused by a scrapes, cuts, abrasion, surgical procedures (e.g., caused by minimally invasive surgery, laparoscopic surgery, robotic surgery, incisional biopsies, general surgery, and cosmetic surgery), denuded skin, burns, ulcers (e.g., diabetic ulcers, ulcers from vascular insufficiency, pressure sores, and burns), or other skin problems (e.g., allergies). Wound may range from superficial (e.g., affecting merely the epidermis) to more traumatic (e.g., lesions which affect layers of skin or tissue at depths which are beneath the epidermis). Wounds may be of any length or shape, e.g., in some embodiments, wounds are straight, jagged or curved.

As used herein, the term "tissue" means any human or other animal tissue including, but not limited to skin, muscle, tendon, bone, heart, lung, kidney, brain, bowel, colon, rectum, stomach, esophagus, etc.

Reference to the term "PMMA" as used herein is meant to refer to poly(methyl methacrylate), which is also known as Poly(methyl 2-methylpropenoate (IUPAC name), polymethyl methacrylate, or more commonly known as Plexiglass™.

The terms "affixed" and "attached" are used interchangeably throughout, and have their ordinary meaning, e.g., being connected or fastened to something else.

Accordingly, other terms such as "connected", "fastened", and "bound" may also be used in a similar manner.

The term "everted" or "eversion" as used herein is intended to have its normal medical meaning, e.g., in regard to the eversion of a wound. Accordingly, an everted wound refers to a wound that is closed (or at least substantially closed), wherein the wound edge is slightly raised above the normal skin level. Wound edge eversion is a common suturing technique to reduce the formation of linear pits and visible scarring.

The term "grasping" is used herein, to describe a microstructure-based anchoring of a wound closure device to its intended location on the surface of the skin or tissue to which it is applied; said anchoring not requiring penetration into the skin or tissue by the microstructures, but instead e.g., being anchored via friction generated by the contact of the microstructures with the skin or tissue. In some embodiments, the device is anchored by grasping, optionally with or without the assistance of the other various components of the present wound closure devices and systems, e.g., a protective cover or adhesive.

The term "penetration" or "penetrate" is meant herein to refer to the action of piercing the skin or tissue, e.g., with one or more of the microstructures disclosed herein.

The term "inflammation" is meant to have its ordinary medical meaning, i.e. a biological response of a tissue to a harmful stimulus. Common signs of inflammation include pain, heat, redness (erythema), swelling (edema), and loss of function.

The term "base" is meant generally to describe a supporting means from which one or more microstructures protrude. In some embodiments, the base comprises a plurality of microstructures; and in other embodiments devices comprising singular microstructures on a base are provided. The base may be a separate component upon which one or more microstructures are affixed; or alternatively, the microstructures and the base may be one continuous component that are fabricated at the same time, optionally from the same or different materials. For example, but not to be limited in any way, some embodiments of the present invention provide for wound closure devices comprising one or more microstructure arrays patterned on a base, wherein both the base and the microstructures are made out of PMMA. In one such embodiment, the microstructures are manufactured using a replica molding technique, wherein both the microstructures and the array are manufactured simultaneously, and are thus in essence one single component (See FIGS. 1a to 1f). Further embodiments provide for a variety of base specifications including, e.g., thickness, length, width, and composition. In certain embodiments, the base comprises a substantially planar upper surface and a substantially planar lower surface; said upper surface comprising one or more microstructures, and said lower surface optionally being affixed to a backing. In such an embodiment, the upper surface comprising the microstructures is intended to be put in contact with the skin or tissue of the patient and the lower surface is intended to be exposed to the external environment, or optionally to be in contact with a protective cover, e.g., a cover comprising adhesive.

The term "array" and "microstructure array" are used herein to describe a two-dimensional configuration of two or more microstructures on a "base", as described herein, said base having a substantially planar upper surface from which the microstructures protrude. The "array" may be in any suitable shape or pattern, and the array may be of any suitable size or dimensions. Furthermore, arrays may comprise any suitable number or density of microstructures, said microstructures optionally extending from the base at angle, or in a substantially perpendicular manner.

An "array region" as used herein is meant to describe an area of the present devices upon which one or more microstructure arrays are affixed. Accordingly, in some embodiments the array region is a portion of the backing upon which one or more bases are affixed, said bases each comprising one or more microstructure or microstructure arrays. In some particular embodiments, the devices of the present invention comprise at least two "array regions" that are separated from one another by an isthmus, as described herein. A non-limiting example of such a design is shown in FIGS. 13a to 13e; wherein a wound closure device is depicted, said device comprising two array regions, each region comprising one microstructure array affixed to a backing; wherein the two array regions are separated by an isthmus of the exact same width as the backing Another similar non-limiting example is shown in FIGS. 15a to 15e, wherein the device comprises two array regions separated by an isthmus with a narrow width compared to the width of the backing upon which the arrays are affixed.

The term "isthmus" as used herein refers to a space with no arrays, that separates two or more microstructure "arrays" or "array regions". "Isthmus separation" refers to the distance separating two arrays on opposing sides of an isthmus. The isthmus may comprise any suitable material, and may in some embodiments be rigid, flexible, and/or stretchable. The size and shape of the isthmus may vary, and in some embodiments the device will comprise an isthmus and a backing, both being made out of the same material, while in other embodiments the material comprised in the isthmus will differ from that of the backing. In certain embodiments, the isthmus is simply created by affixing two or more microstructure arrays upon a backing such that a space separates the two arrays. In still other embodiments, the isthmus is a portion of a base comprising a plurality of microstructure arrays (i.e., the isthmus and the microstructures are made of the same material). Non-limiting examples of two different types of isthmuses can be seen in FIGS. 13a to 13e and 15a to 15e wherein the shape, composition (silicone vs. thermoplastic polyurethane ("TPU")), and properties (i.e. stretchable vs. non-stretchable) have been varied. Furthermore, FIGS. 15a to 15e demonstrate the optional addition of a therapeutic (e.g., 2% Chitosan hydrogel) to the isthmus to further promote wound healing. In some embodiments, the isthmus ranges from 1 mm in length to 15 mm in length. Accordingly, in these embodiments, the devices of the present invention may comprise isthmuses that are 1 mm in length, or they may comprise isthmuses that are 2 mm; 3 mm; 4 mm; 5 mm; 6 mm; 7 mm; 8 mm; 9 mm; 10 mm; 11 mm; 12 mm; 13 mm; 14 mm; or 15 mm in length, including all decimals (e.g., 1.5 mm, 1.6 mm, 1.7 mm, etc.) and ranges (e.g., 1-15 mm, 5-10 mm, 10-15 mm, 3-4 mm, 5-6 mm, 6-8 mm, etc.) in between, of the isthmus lengths set forth herein. The width of the isthmus may vary. In some embodiments the isthmus width is the same as the base or backing of the device. In other embodiments, the isthmus is wider or narrower than the base or backing of the device. Thus, the width of the isthmus may range from as small as 1 mm to as large as 50 cm or more. Accordingly, isthmus widths may range from approximately 1 mm, 2 mm, 3 mm, 4 mm, 5 mm, 6 mm, 7 mm, 8 mm, 9 mm, 1 cm, 2 cm, 3 cm, 4 cm, 5 cm, 10 cm, 20 cm, 30 cm, 40 cm, 50 cm, or longer, including all integers (e.g., 11 mm, 12 mm, 13 mm, etc.) and ranges (e.g., 2 mm-50 cm, 5 mm-15 mm, 5 mm-10 mm, etc.) in between of the isthmus widths set forth herein.

As used herein, when components of the wound closure devices are said to be positioned or distributed "anisotropically", it is meant that the components are not uniform throughout, but instead their properties vary directionally. Thus, e.g., in some embodiments, anisotropic positioning refers to variation in the components of individual microstructures comprised in a microstructure array, said microstructures comprising directional variability in their physical properties, e.g., their aspect ratios or angles of attachment to a backing. In other embodiments, this variability may be in regard to directional differences between different arrays. Anisotropic variability may be in one direction, or in more than one direction.

As used herein, the term "microstructure" refers to a three-dimensional structure projecting from or connected to a base. A microstructure may be an integral part of the base (i.e., the microstructure and base are monolithic). Alternatively, the microstructure may be of separate construction than the base but be joined to the base (e.g., through adhesive, bonding, etc.).

Microstructures typically have dimensions on the micron size scale, although certain dimensions may extend into the millimeter size scale (e.g., length) and certain dimensions may be smaller than one micron (e.g., nano scale tip width).

Representative microstructures include microneedles, microblades, microanchors, microfishscale, micropillars, and microhairs.

A microstructure includes a foundation, a tip, and a body joining the foundation with the tip.

As used herein, the term "foundation" refers to the two-dimensional area where the base meets the microstructure. The foundation may be better understood with reference to FIGS. 5a and 5c. The foundation can be any two-dimensional shape, including a circle, oval, ellipse, triangle, rectangle, square, quadrilateral, or higher-order polygon.

As used herein, the term "tip" refers to the end of the microstructure distal to the foundation and base. The tip may be a single point (e.g., a needle), a line (e.g., a blade), or other shape.

As used herein, the term "body" refers to the portion of the microstructure between the foundation and the tip. The body may be better understood with reference to FIGS. 5a and 5c. The body may also be referred to herein as a "shaft" of the microstructure. The body has a "length" that is equal to the longest distance connecting a point on the foundation to the tip.

The microstructure can be either straight or curved. In certain embodiments, the body connects the foundation to the tip without curvature along its length. In other embodiments, the body is curved along its length between the foundation and the tip.

As used herein, the term "straight" refers to a microstructure having no curvature (i.e., no concave or convex surfaces) along the body between the foundation and the tip. Examples of straight microstructures are illustrated schematically in FIGS. 4a to 6a and photographically in FIGS. 2a and 2c.

As used herein, the term "curved" refers to a microstructure having one or more concave or convex surfaces along the body between the foundation and the tip. Examples of curved microstructures are illustrated schematically in FIGS. 6b and 6d and photographically in FIGS. 2b, 12a, and 12b.

Straight and curved microstructures can be defined in terms of a "face angle" ($\theta_F$), which is the smallest angle formed between the base and the microstructure. Referring to the straight microstructure illustrated in FIG. 6a, the face angle is constant along the entire body from the foundation to the tip. The curved and articulated microstructures in FIGS. 6b and 6c, respectively, include multiple different face angles along the body, as illustrated by comparing Angle $\theta_1$, formed between the base and tangent $T_1$, to Angle $\theta_2$, formed between the base and tangent $T_2$. Angle $\theta_1$ is different than Angle $\theta_2$. The face angle will always be greater than the overall angle of the microstructure. In certain embodiments, the face angle is greater than 90 degrees (e.g., for a straight microstructure at 90 degrees relative to the base). In certain embodiments, the face angle is less than 90 degrees. In one embodiment, the face angle is from 5-90 degrees. In one embodiment, the face angle is from 10-80 degrees. In one embodiment, the face angle is from 20-70 degrees. In one embodiment, the face angle is from 50-70 degrees.

Figure 6A:
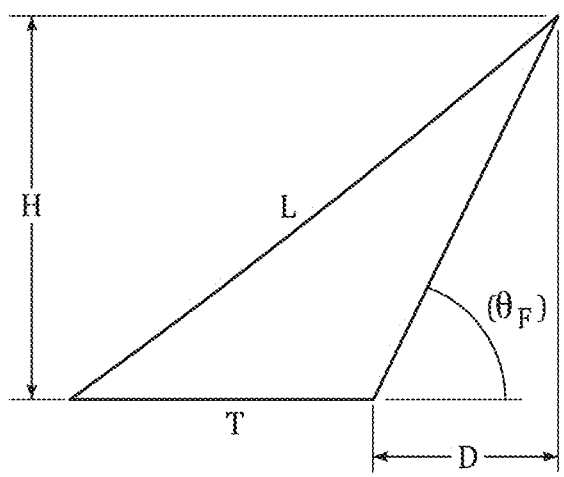
FIG. 6a schematically illustrates an angled microstructure.
Figure 6B:
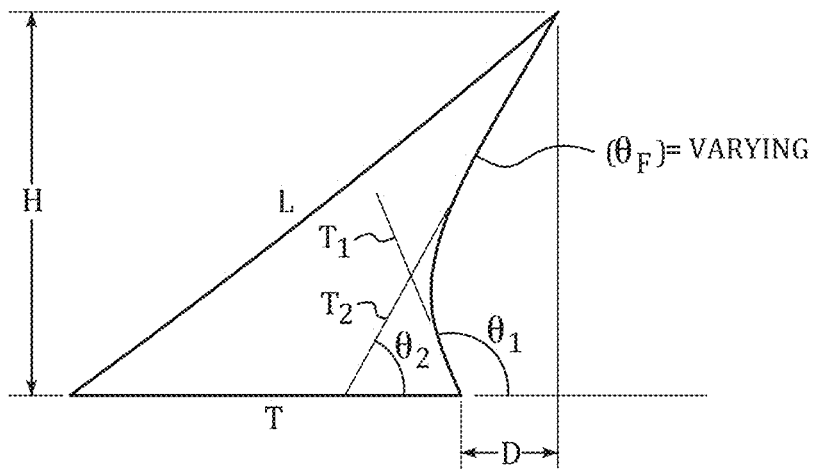
FIG. 6b schematically illustrates a curved microstructure.
Figure 6C:
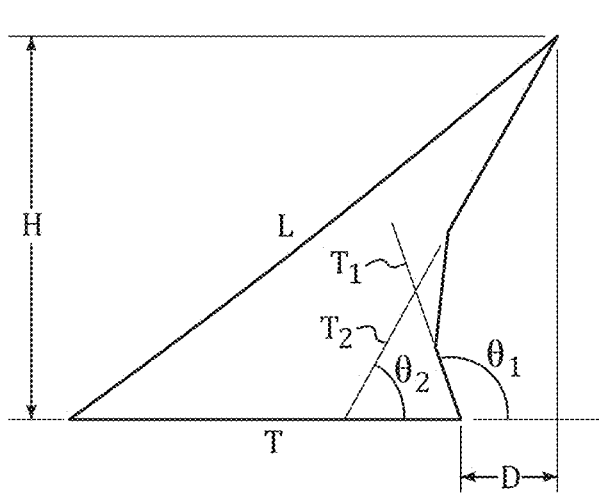
FIG. 6c schematically illustrates an articulated microstructure.

As used herein, the term "articulated" refers to a microstructure that does not curve continuously but instead curves via one or more joints connecting straight portions. An articulated microstructure may also be referred to as "beveled." An articulated microstructure is illustrated in FIG. 6c.

Figure 6D:
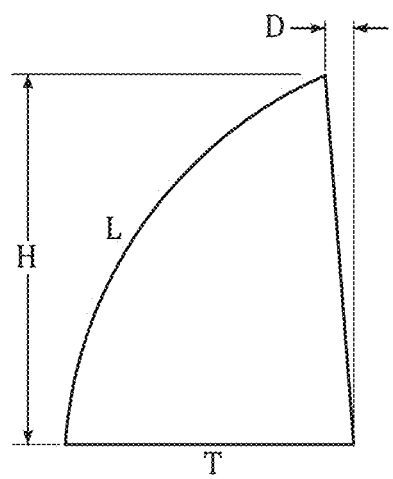
FIG. 6d schematically illustrates a curved microstructure.

As used herein, the term "convex" refers to a microstructure having at least one line along the outer surface of the body that deviates outwardly from a straight line between the foundation and the tip. An exemplary convex microstructure is illustrated in FIG. 6d.

As used herein, the term "concave" refers to a microstructure having at least one line along the outer surface of the body that deviates inwardly from a straight line between the foundation and the tip. An exemplary concave microstructure is illustrated in FIG. 6b.

As used herein, the term "angled" refers to a microstructure that is not perpendicular to the base. The angle of a microstructure in relation to the base can be understood with reference to FIG. 5a, which illustrates a straight microstructure having a line, through the body, connecting the tip to a center point. The "center point" is the center of the foundation. The angle ("center point angle"; $\theta_c$) formed between the line and the base defines the angle of the entire microstructure.

For microstructures, if the tip is not directly above the center point then the microstructure is angled.

Curved microstructures may be defined by an angle if a tip-to-center point line can be drawn so as to define an angle in relation to the base. However, extensively curved microstructures may not allow a straight line to be drawn through the body from the tip to the center point.

As used herein, the term "microneedle" is intended to refer to any microstructure comprising straight or tapered shafts. In one embodiment, the diameter of the microneedle is greatest at the base end of the microneedle and tapers to a point at the end distal the base. The microneedle can also be fabricated to have a shaft that includes both a straight (untapered) portion and a tapered portion. The microneedles can be formed with shafts that have a circular cross-section in the perpendicular, or the cross-section can be non-circular. For example, the cross-section of the microneedle can be polygonal (e.g. star-shaped, square, rectangular, and triangular), oblong, or another shape. The tip portion of the microneedles can have a variety of configurations. The tips can be symmetrical or asymmetrical about the longitudinal axis of the microneedle shaft. In one embodiment, the tips are beveled. In another embodiment, the tip portion is tapered. In one embodiment, the tapered tip portion is in the shape of a pyramid on a shaft portion having a square cross-section, such that the microneedle is in the shape of an obelisk. Of course, the tip and/or shaft can be rounded, or have another shape, as well. In some embodiments the microneedles comprise a shape that is a e.g., rod, cone, square, rectangle, pyramid, cylinder.

As used herein, the term "microblade" is intended to refer to a needle-like microstructure comprising a tip that is not a point, but is instead a blade. This embodiment is illustrated, for example, in FIGS. 8a-1 to 8a-6 and 12b, which shows a picture of a microstructure array comprising microblades. The tip portion of these structures is wide in a first dimension (50 µm in this picture) and very narrow in a second dimension, with respect to the first dimension (e.g., less than 10 µm in this picture) Furthermore, in some embodiments, the thickness at the tip is smaller than the width of the microblades near their base.

As used herein, the term "microanchor" is intended to refer to any microstructure capable of anchoring a device according to the present disclosure to skin or tissue. Examples of microanchors include microstructures with ends shaped like hooks or barbs. As used herein, the term "barb" refers to a tip configuration comprising angled portions projecting away from the tip in order to secure the barb within the penetrated skin or tissue.

As used herein, the term "microfishscale" is intended to refer to any microstructure comprising a scale that partially overlaps, with other scales of microscale dimensions and mimics the scale of a fish.

As used herein, the term "micropillar" is intended to refer to any microstructure comprising a cylindrical shape.

As used herein, the term "microhair" is intended to refer to any microstructure comprising hair-like features which enable the contacting and sticking of the microhair to another object via van der Waals forces.

The term "tapered" is meant to describe a microstructure wherein the width or diameter gradually diminishes along the length of the needle from the base to the tip, such that the base comprises the largest width or diameter, and the tip comprises the smallest width or diameter. A "partially tapered" microstructure is one in which a portion of the microstructure is tapered and a portion of the microstructure is not tapered. For example, but not to be limited, such a microstructure can comprise a tapered portion extending from a block shaped base; or e.g., a cylindrical base portion can extend toward the tip for a certain length, and then a tapered portion can continue to the tip. Alternatively, the microstructure can comprise a tapered portion extending from the base, with a non-tapered portion being at the tip end of the microstructure.

The term "stretchable" as used herein is meant to encompass any material that can be elongated in any direction, e.g., as a result of a pulling force. "Stretchable" encompasses the term "elastic" and thus an object that is said to be stretchable should be understood to optionally comprise elasticity. Thus in some embodiments, if an object is said to be stretched, this is meant to include at least two embodiments; the first being that the stretching force will be counteracted by a retractile force, and thus once the stretching force is removed, the object will inherently attempt to retract (e.g., as is the case with an elastic object). The second embodiment is one in which the object does not inherently comprise elasticity, and thus no such retractile force is inherent.

The term "flexible" is meant to describe any material that is capable of sustaining a bending force without being damaged. In some embodiments, a "flexible" material comprises enough flexibility as to allow the device of the present invention to bend so as to fit the contours of the biological barrier, such as, e.g., the skin, vessel walls, or the eye, to which the device is applied.

The term "backing" as used herein, is meant to describe an optional component of the present wound closure devices which is attached to one or more arrays. In some embodiments the backing attaches two or more microstructure arrays together. As is thoroughly described in the detailed description, the backing may comprise any suitable material, and in several embodiments it is flexible, stretchable, elastic, or combinations thereof.

The term "cover" as used herein in meant to describe an optional component of the wound closure systems disclosed herein whereby it covers the wound. After application of the wound closure devices of the present invention, such a cover may be optionally applied over and/or attached to the top of the device, e.g., assist in securing the device in place. The covers may be made of any suitable material, as is discussed and defined thoroughly in the detailed description section below. In some embodiments the covers comprise adhesive.

When it is said that one or more microstructures are "affixed to a backing" it is meant that the microstructures may optionally be either directly affixed to the backing, or indirectly affixed to the backing (e.g., in some embodiments, "affixed to a backing" is meant to encompass the scenario wherein the microstructures are fashioned on, or affixed to, a base, said base being affixed to a backing). Accordingly, the phrase "one or more microstructures affixed to a backing" can appropriately be used interchangeably with the phrase "a backing comprising one or more microstructures."

As used herein, the term "pitch" is meant to describe the distance between the tips of two or more adjacent microstructures in a given array, or in two or more separate arrays. In some embodiments the pitch ranges from 30 µm to 1 cm or more. Accordingly, certain embodiments provide for microstructure arrays as disclosed herein, wherein the microstructures are separated from one another with a pitch of 30 µm, 50 µm, 70 µm, 90 µm, 100 µm, 150 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1 mm, 1.1 mm, 1.2 mm, 1.3 mm, 1.4 mm, 1.5 mm, 2 mm, 2.5 mm, 3 mm, 3.5 mm, 4 mm, 4.5 mm, 5 mm, 6 mm, 7 mm, 8 mm, 9 mm, 10 mm, or more, including all decimals (e.g., 3.1 mm, 3.2 mm, 3.3 mm, etc.) and ranges (e.g., 1-10 mm, 5-10 mm, 7-10 mm, etc.) in between, of the microstructure array pitches set forth herein. The pitch may be constant throughout an array, e.g., an equal distance separates all microstructure tips from one another in a given array; or the pitch may vary.

Reference herein to the term "tape" or "microstructure tape" or "microstructure array tape", is simply meant to describe an adhesive-comprising microstructure array roll bandage, as described herein.

Reference to a "Draize score" refers to a score according to the Draize scale, which is a standard scoring system used to measure skin toxicities of devices and drugs.

As used herein, the term "adhesive" or "glue" are used interchangeably. These terms are meant to have their ordinary meaning, e.g., any substance that is capable of binding two or more materials together. In some embodiments, the adhesive is intended to be used on the skin. In such embodiments the adhesive may be a medical grade adhesive such as, e.g., an acrylate (such as, e.g., are used on the Steri-Strips or Steri-Strip S isthmus), or hydrogel based adhesives that can stick to wet surfaces (e.g. Polyethylene glycol (PEG) hydrogel). In other embodiments the adhesive component comprises nanostructures that provide glueless adhesion.

The term "applicator" as used herein is meant to describe any machine or instrument that is used to affix a wound closure device, e.g., to the skin or tissue surrounding a wound. Accordingly, the use of medical instruments such as forceps, tweezers, clamps, pins, etc., to apply such a device would be considered to be use of an applicator. The term "applicator" also refers to the roll on hand held dispenser disclosed herein. Thus, when it is said that the device is applied without an applicator, this is to be understood as being applied by human hand, without the aid of a machine or instrument.

Microstructures

The microstructures comprised in the wound closure devices disclosed herein may be made of any material or mixture of materials. In some embodiments, the material is a natural material, or a mixture of natural materials; while in other embodiments it is a synthetic material, or a mixture of synthetic materials. In some embodiments, the microstructures are comprised of nontoxic, biodegradable, bioresorbable, or biocompatible materials, or combinations thereof; and in other embodiments they are not. Still other embodiments provide for microstructures, according to the present disclosure, comprising mixtures of one or more synthetic materials and one or more natural materials. In particular embodiments, microstructures are made of a material selected from a polymer, a metal, a biomaterial, and a combination thereof.

In certain embodiments, microstructures of the present invention are comprised of a material selected from the group consisting of PMMA, silicone, chitin, chitosan, ecoflex, titanium, glass, metal, steel, silicon, silk, catgut, chromic catgut, polyglycolic acid, polydioxanone, polytrimethulene carbonate, nylon, polypropylene, polyester, polybutester, poly(lactic-co-glycolic acid), polylactone, elastin, resilin, collagen, cellulose, and any combination thereof.

Embodiments of the present invention provide for microstructures selected from the group consisting of microneedles, microblades, microanchors, microfishscale, micropillars, microhairs, and combinations thereof. Microstructures may be designed to be able to penetrate into skin or tissue, or they may be designed to merely grasp skin or tissue without actual penetration. In some embodiments, the microstructures are designed to penetrate the skin or tissue to specific depths, e.g., through the epidermal or dermal layers, or to the various sublayers thereof.

The wound closure devices of the present invention may comprise microstructures of any desired size, dimension, and geometry. Additionally, microstructures may optionally comprise surfaces which are substantially smooth, or which comprise uneven surfaces, e.g., a microstructure comprising sides which are wavy, or which comprise protrusions, indentations, or depressions.

In one aspect, the microstructure includes a foundation adjacent to a base, a tip, and a body connecting the foundation to the tip.

In one embodiment, a line extending from the tip perpendicular to the base does not pass through the foundation. Angled and/or curved microstructures may have a shape that positions the tip beyond the foundation. Examples of such microstructures are illustrated schematically in FIG. 5a and photographically in FIG. 2b. Additionally, it will be appreciated that any microstructure, no matter the body shape, angle, and/or curvature, that has a tip position as described is contemplated by the present embodiment.

In one embodiment, a line extending from the tip perpendicular to the base passes through the foundation. Angled and/or curved microstructures may have a shape that positions the tip within the perimeter of the foundation. Examples of this microstructure configuration are illustrated schematically in FIG. 5b and photographically in FIG. 2a. Additionally, it will be appreciated that any microstructure, no matter the body shape, angle, and/or curvature, that has a tip position as described is contemplated by the present embodiment.

Figure 5A:
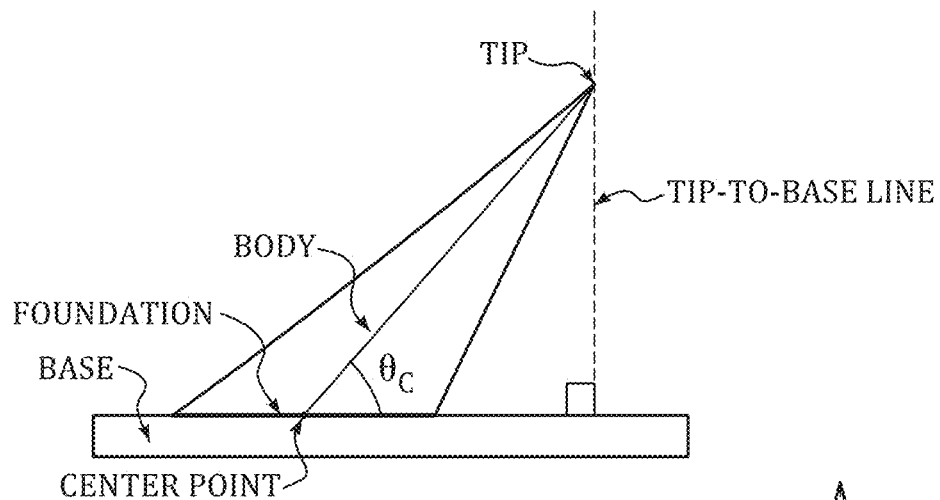
FIG. 5a schematically illustrates a microstructure (e.g., a microneedle or microblade) angled and proportioned such that a line extending from the tip perpendicular to the base does not pass through the foundation.
Figure 5B:
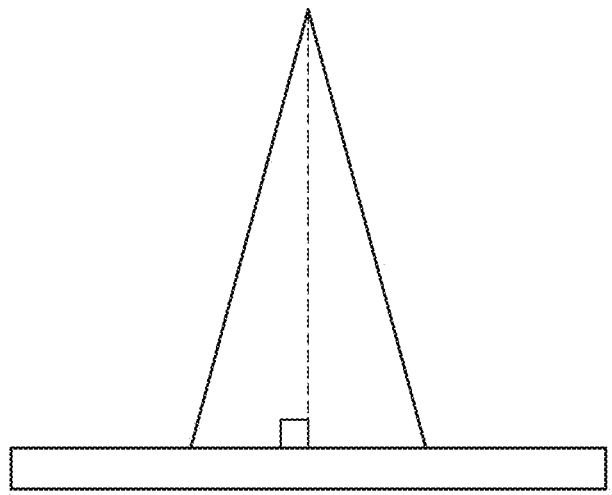
FIG. 5b schematically illustrates a microstructure (e.g., a microneedle or microblade) angled and proportioned such that a line extending from the tip perpendicular to the base passes through the foundation.
Figure 5C:
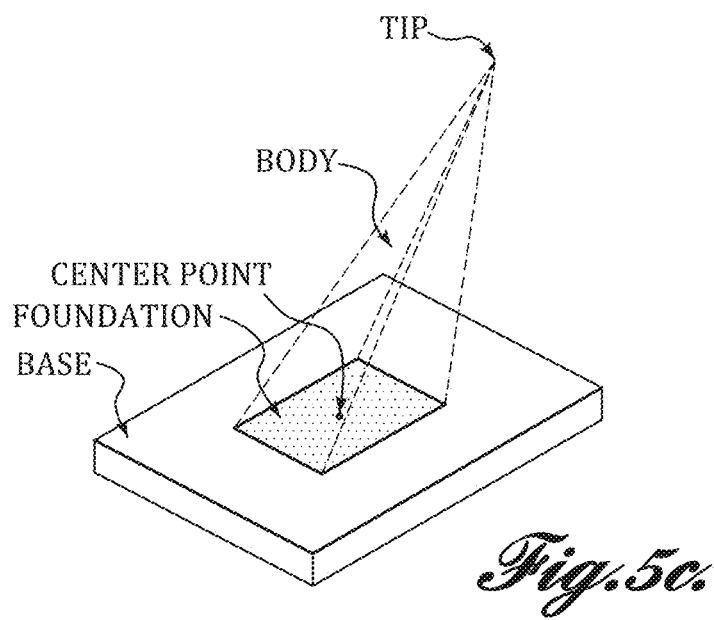
FIG. 5c schematically illustrates a microstructure similar to FIG. 5a in partial-phantom perspective view.

In one embodiment, an angle between the body and the base is a constant angle. In such an embodiment, the center point angle and the face angle are constant. FIGS. 5a and 6a are examples of such a microstructure.

In one embodiment, two or more different angles are formed between the body and the base between the foundation and the tip. Curved or articulated microstructures are examples of such a microstructure. FIGS. 6b and 6c are examples of such a microstructure.

The body of the microstructures can have concave surfaces, convex surfaces, and a combination of concave and convex surfaces. In one embodiment, the body comprises at least one concave surface. In one embodiment, the body comprises at least one convex surface. In one embodiment, the body comprises at least one concave surface and at least one convex surface.

In certain embodiments, the microstructures comprise microneedles. Microneedles narrow from a foundation to a tip. Representative microneedles are illustrated in FIGS. 3a-1 to 3a-6.

Referring to FIG. 3a-4, each microneedle includes a foundation that has a width (W1) and thickness (T). While the microneedles illustrated in FIGS. 3a-1 to 3a-6 have rectangular foundations, it will be appreciated that this is only one embodiment of the microneedles. Other embodiments include microneedle foundations that are circular, oval, triangular, square, higher-order polygons, and combinations thereof.

The tip of the microneedle extends a length (L) from the foundation. The tip can also be offset a distance (D) such that the tip is not centered vertically above the foundation. In certain embodiments, the tip is centered vertically above the center point of the foundation. In other embodiments, the tip is positioned vertically above a point on the perimeter of the foundation.

While the tip of a microneedle converges to a single point, the tip has some diameter as a result of fabrication.

As illustrated in FIG. 3a-6, each microneedle has a face angle (OF) formed between a side wall of the microneedle and the surface supporting the microneedle.

In certain embodiments, the microstructures comprise microblades. Microblades narrow from a foundation to a tip. Representative microblades are illustrated in FIGS. 8a-1 to 3a-6.

Referring to FIG. 8a-4, each microblade includes a foundation that has a width (W1) and thickness (T). While the microblades illustrated in FIGS. 3a-1 to 3a-6 have rectangular foundations, it will be appreciated that this is only one embodiment of the microblades. Other embodiments include microblade foundations that are circular, oval, triangular, square, higher-order polygons, and combinations thereof.

The tip of the microblade extends a length (L) from the foundation. The tip can also be offset a distance (D) such that the tip is not centered vertically above the foundation. In certain embodiments, the tip is centered vertically above the center point of the foundation. In other embodiments, the tip is positioned vertically above a point on the perimeter of the foundation.

Unlike a microneedle, a microblade has a tip that forms a line, not a single point. The microblade tip has a width (W2) and a nominal thickness.

As illustrated in FIG. 8a-6, each microblade has a face angle formed between a side wall of the microblade and the surface supporting the microblade.

Microneedles and microblades interact with the skin of a patient in different ways, given their different characteristics. For example, microblades provide more surface area than microneedles of the same length and width. By providing a larger surface area, microblades are able to remain anchored to the skin with higher lateral tension than microneedles. Consequently, a smaller number of microblades can be used to close a wound under tension than can be achieved with microneedles.

Microstructures may have heights ranging from approximately 1 µm to approximately 3 mm. Thus, microstructures may have heights of approximately 1 µm, 10 µm, 50 µm, 100 µm, 150 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1 mm, 1.5 mm, 2 mm, 3 mm, or higher, including all integers (e.g., 2 µm, 3 µm, 4 µm, etc.) and ranges (e.g., 100-1000 µm, 500-1000 µm, 700-1000 µm, 950-1000 µm, etc.) in between, of the microstructure heights set forth herein. Accordingly, the microstructure arrays of the present invention may comprise individual microstructures that have heights of approximately 1 µm up to approximately 3 mm, as described above. Longer (e.g., 3 mm or longer) microstructures are needed for treatment areas that include thicker dermal tissue (e.g., the back).

Microstructures may have widths or diameters, as measured by the area meeting the foundation of the base, ranging from approximately 15 µm up to approximately 2 mm (e.g., see Width 'W1' in FIGS. 8a-4). Thus, microstructures may have widths or diameters of approximately 15 µm, 30 µm, 50 µm, 100 µm, 150 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1 mm, 1.5 mm, 2 mm, or wider, including all integers (e.g., 101 µm, 102 µm, 103 µm, etc.) and ranges (e.g., 100-1000 µm, 200-500 µm, 500-1000 µm, 700-1000 µm, etc.) in between, of the microstructure widths and diameters set forth herein. Accordingly, the microstructure arrays of the present invention may comprise individual microstructures that have widths or diameters of at least or approximately 15 µm up to approximately 2 mm, as described above.

Microstructures may have tips with widths or diameters of approximately 10 nm up to approximately 50 µm (e.g., see Width 'W2' in FIGS. 8a-4). Thus, microstructures may have tips with a width or diameter of approximately 10 nm, 20 nm, 30 nm, 40 nm, 50 nm, 60 nm, 70 nm, 80 nm, 90 nm, 100 nm, 125 nm, 150 nm, 175 nm, 200 nm, 300 nm, 400 nm, 500 nm, 600 nm, 700 nm, 800 nm, 900 nm, 1 µm, 5 µm, 10 µm, 15 µm, 20 µm, 25 µm, 30 µm, 35 µm, 40 µm, 45 µm, 50 µm, or wider, including all integers (e.g., 11 nm, 12 nm, 13 nm, etc.) and ranges (e.g., 10 nm-50 µm, 200-1000 µm, 500-1000 µm, 700-1000 µm, etc.) in between, of the microstructure widths or diameters set forth. Accordingly, the microstructure arrays of the present invention may comprise individual microstructures that have tips with widths or diameters of approximately 10 nm up to approximately 50 µm, as described above.

If a microstructure includes a tip offset (D), the offset can be from 1 nm to one-half the thickness (T) or width (W1) of the foundation of the microstructure. In one embodiment, the tip offset is from 20% to 33% of the thickness of the foundation of the microstructure.

Microstructure Bases

Bases, which may optionally comprise the various microstructures and microstructure arrays, may be made of any suitable material. The base may be transparent or substantially transparent (e.g., to enable non-invasive wound observation) or alternatively, it is not transparent (e.g., to hide the wound). The base may optionally comprise nontoxic, biodegradable, bioresorbable, or biocompatible materials, or combinations thereof. The base may be made out of the same material as the microstructures it comprises, or it may be made of a different material.

Accordingly, as is the case with the microstructures, the present invention provides for microstructure bases comprising any material or mixture of materials. In some embodiments, the material is a natural material, or a mixture of natural materials; while in other embodiments it is a synthetic material, or a mixture of synthetic materials. Still other embodiments provide for microstructure bases, according to the present disclosure, comprising mixtures of one or more synthetic materials and one or more natural materials. In particular embodiments, microstructure bases are made of a material selected from a polymer, a metal, a biomaterial, a hydrogel, a glass, and a combination thereof.

In certain embodiments, microstructure bases of the present invention are comprised of a material selected from the group consisting of PMMA, silicone, chitin, chitosan, titanium, glass, metal, steel, silicon, silk, catgut, chromic catgut, polyglycolic acid, polydioxanone, polytrimethulene carbonate, nylon, polypropylene, polyester, polybutester, poly(lactic-co-glycolic acid), elastin, resilin, collagen, cellulose, and any combination thereof.

In one certain embodiment, the microstructures and the bases are both comprised of PMMA. In another certain embodiment, the microstructures and the bases are both comprised of silicone.

The thickness of the base may be substantially uniform throughout the device, or alternatively it may be varied. In some embodiments, the thickness of the base is determined by the material that it is made out of, e.g., a 1 mm thickness for a silicone base may be used, as this material comprises acceptable flexibility at such a thickness; a base comprising PMMA, on the other hand may be fashioned at approximately 125 µm or less thick in some instances, so as to maintain some degree of flexibility. Alternatively, a PMMA base may be thicker, e.g., 300 µm thick, if a stiffer base is desired. One skilled in the art can easily determine the appropriate thickness of a base depending on the material from which it is made, and the desired flexibility or lack thereof of the base. Accordingly, in some embodiments, the thickness of the base ranges from approximately 10 µm to approximately 1 mm. In particular embodiments, the base thickness is approximately 10 µm, 20 µm, 30 µm, 40 µm, 50 µm, 60 µm, 70 µm, 80 µm, 90 µm, 100 µm, 125 µm, 150 µm, 175 µm, 200 µm, 300 µm, 400 µm, 500 µm, 600 µm, 700 µm, 800 µm, 900 µm, 1 mm or thicker, including all integers (e.g., 126 µm, 127 µm 128 µm, etc.) and ranges (e.g., 50 µm-200 µm, 100-160 µm, 120-140 µm, etc.) in between, of the microstructure base thicknesses set forth.

Bases may be as long or wide as is necessary to comprise the desired microstructure array or arrays. For example, but not to be limited in any way, the dimension of a base may be as small as 1 mm wide in the dimension perpendicular to the wound, so as to have one set of microstructures parallel to the wound; and this dimension may range as wide as 10 cm or larger. For the dimension parallel to wound the bases can range from 2 mm, to as large as 50 cm long or more (e.g., as is optionally the case in some of the microstructure array roll bandages disclosed herein). Accordingly, base lengths may range from approximately 2 mm, 5 mm, 10 mm, 2 cm, 3 cm, 4 cm, 5 cm, 10 cm, 20 cm, 30 cm, 40 cm, 50 cm, or longer, including all integers (e.g., 11 mm, 12 mm, 13 mm, etc.) and ranges (e.g., 2 mm-50 cm, 5 mm-15 mm, 5 mm-10 mm, etc.) in between, of the base lengths parallel to the wound set forth; and base widths may range from approximately 1 mm, 3 mm, 5 mm, 7 mm, 9 mm, 1 cm, 2 cm, 3 cm, 4 cm, 5 cm, 10 cm, or longer, including all integers (e.g., 11 mm, 12 mm, 13 mm, etc.) and ranges (e.g., 1 mm-10 cm, 2 mm-10 mm, 5 mm-10 mm, etc.) in between, of the base lengths perpendicular to the wound set forth, as described herein.

Angled Microstructures

In some embodiments, the wound closure devices of the present invention comprise microstructures at an angle relative to the backing or base. The microstructures may be positioned at any suitable angle. In some embodiments they are affixed at an angle relative to a backing or base, wherein the angle is approximately 15, 30, 45, 60, 75, or 90 degrees, including all integers (e.g., 16°, 17°, 18°, etc.) and ranges (e.g., 15°-90°, 30°-90°, 45°-70°, etc.) in between, of the angles set forth. In one embodiment, the microstructures are at an angle of greater than 50 degrees relative to the backing or base. In one embodiment, the microstructures are at an angle of from 45 to 70 degrees relative to the backing or base. In one embodiment, the microstructures are at an angle of from 50 to 70 degrees relative to the backing or base.

In some embodiments, the wound closure devices of the present invention also include microstructures with an angle relative to the backing or base that is variable depending on its position in any microstructure array. In certain embodiments, the angle of one or more microstructures is approximately constant along the entire length of the microstructure, and in other embodiments, the angle of the microstructure varies along the length of the microstructure.

Microstructures may be angled in any direction. In some embodiments, all microstructures in a particular array are angled in the same direction, or in approximately the same direction; while in other embodiments they are not. In certain embodiments, microstructures on a device are angled towards a wound. In some particular embodiments, the microstructures in an array comprise subsets of microstructures angled in different directions.

Microstructure Arrays

The wound closure devices of the present invention may comprise microstructure arrays patterned on one or more bases in a variety of shapes and dimensions. FIGS. 3a-1 to 3a-6 and 8a-1 to 8a-6 show schematic designs of several arrays we have produced. The details of exemplary microneedles (FIG. 3b) and microblades (FIG. 8b) are provided in a table. Furthermore, photographs of one such microneedle array and microblade arrays are provided in FIGS. 7a and 7b, and FIGS. 12a and 12b, respectively.

In particular, devices of the present invention may comprise arrays in which the length or width of an array is designed to enable treatment of specific wound types or sizes. For example, but not to be limited in any way, the dimension of an array that runs parallel to a wound can be as wide as 50 cm e.g., to treat a 50 cm long straight wound; or, alternatively it can be as narrow 2 mm wide, e.g., to treat a 2 to 5 mm long wound. Similarly, the length of the other dimension of an array (i.e., the dimension that runs perpendicular to the wound) may be as small as 1 mm and as large as 50 mm. Accordingly, the dimensions of an individual array may comprise lengths and/or widths of 1 mm, or they may comprise lengths and/or widths of 2 mm, 3 mm, 5 mm, 7 mm, 9 mm, 10 mm, 2 cm, 3 cm, 4 cm, 5 cm, 10 cm, 15 cm, 25 cm, 50 cm, or more, including all integers (e.g., 11 cm, 12 cm, 13 cm, etc.) and ranges (e.g., 3 mm-50 cm, 9 mm-5 cm, 1 cm-50 cm, etc.) in between, of the microstructure array lengths and widths set forth.

The microstructure arrays may comprise any appropriate number of microstructures. In some embodiments, the number of microstructures comprised in an individual array varies from 1 microstructure per array, to more than 1000 microstructures per array. The microstructure arrays may comprise any density of microstructures. In some embodiments, the density of microstructures comprised in an individual array varies from 1 microstructure per $cm^2$, to 1000 microstructures per $cm^2$. In one embodiment, the density of microstructures comprised in an individual array is from 1 to 100 per $cm^2$. In one embodiment, the density of microstructures comprised in an individual array is from 5 to 50 per $cm^2$. In one embodiment, the density of microstructures comprised in an individual array is from 10 to 20 per $cm^2$. In one embodiment, the density of microstructures comprised in an individual array is from 5 to 10 per $cm^2$.

In particular embodiments, the density of microstructures in an array is decreased to reduce or eliminate the induction of an inflammatory response to the wound closure device. Without being limited by theory, data suggest that arrays comprising lower densities of microstructures (e.g., see FIG. 7a and FIG. 12a) induce less (or no) inflammation than arrays with higher microstructure densities (e.g., see Example 3).

In various embodiments, the microstructure arrays of the present invention comprise microstructures patterned in a variety of shapes or patterns. Any shape or pattern of microstructure arrays is within the scope of the present invention. In some embodiments, the array patterning comprises straight edges. In some embodiments, the arrays are patterned with rounded edges. In still further embodiments, the array patterning comprises shapes with both rounded and straight edges. In some certain embodiments, arrays are patterned in a shape selected from the group consisting of oval, diamond, pyramid, and circle. In some certain embodiments, arrays are patterned in a rectangular shape. In some certain embodiments, arrays are patterned in the shape of a square. In some embodiments, arrays comprise pluralities of microstructures that are pattern into separate shapes, wherein two or more regions of the array comprise a higher density of microstructures than the other regions of the array. Take for example, but not to be limited in any way, a single square shaped array, which may in one embodiment comprise e.g., groups of microstructures in any locale, such as, one group in each of the corners of the array, wherein the four microstructure groups are separated by a region of the array that does not comprise any microstructures, or optionally comprises microstructures at a different density than the density of the microstructures comprised in one of the groups.

Another non-limiting example of this concept is, e.g., a wound closure device that is made up of a single base comprising a single microstructure array, wherein the base comprises a shape that is similar as the device shown in FIGS. 15a to 15e. Such a base comprises group of microstructures on one end of the device and another group on the other end of the device, such that the groups are separated by a space that does not comprise any microstructures.

In some embodiments, the individual microstructures are distributed uniformly throughout an individual array, and in other embodiments the microstructures are not distributed evenly throughout an array. In certain embodiments, wherein the devices comprise a plurality of arrays, distribution of the individual microstructures may be constant between different arrays (e.g., all arrays comprising uniformly distributed microstructures), or they may be varied between arrays (e.g., some arrays comprising uniformly distributed microstructures), and other arrays comprising microstructures distributed in a non-uniform manner.

In some embodiments, the size, dimension, and geometry of the microstructures are constant throughout an individual array, while in other embodiments these properties are varied, e.g., anisotropically. Additionally, in certain embodiments wherein the devices comprise a plurality of arrays, these physical properties may be constant between different arrays (e.g., all arrays comprising identical designs), or they may be varied (e.g., different arrays optionally comprising different designs). Accordingly, some embodiments provide for wound closure devices comprising arrays that are homogeneous with regard to the microstructures they comprise; while other embodiments provide for wound closure devices comprising arrays that are heterogeneous with regard to the microstructures they comprise.

In some embodiments, the devices comprise two different microstructure arrays, said arrays comprising angled microstructures; wherein the microstructures from one array are angled toward the microstructures of the other array, and vice versa. In such embodiments, an isthmus may separate the two different microstructure arrays, such that the arrays are angled towards a wound onto which the device is applied (e.g., if the isthmus is positioned above the wound).

Optionally, the angles of the opposing microstructures comprised in the separate arrays may be the same (e.g., both arrays comprising microstructures that are angled towards the microstructures of the other array at e.g., approximately 45°), substantially the same, or they may be different. Similarly, another embodiment provides for a wound closure device comprising more than two microstructure arrays, wherein at least two of said arrays are angled towards one another as described above. In some embodiments, opposing arrays that are angled towards each other may be located in the same array region (i.e., they are not separated by an isthmus). In some embodiments, opposing arrays that are angled towards each other may be located in different array regions (i.e., they are separated by an isthmus).

The arrays have an aspect ratio defined in relation to the position on the device to be positioned above a wound (e.g., the isthmus). The length is defined as the dimension of the array extending perpendicularly away from the wound. The width is defined as the dimension of the array extending parallel to the wound. In one embodiment the aspect ratio of the array is from 0.1 to 10. In one embodiment the aspect ratio of the array is from 0.4 to 3. In one embodiment the aspect ratio of the array is from 1 to 5. In one embodiment the aspect ratio of the array is from 2 to 3.

Microstructure Manufacture

The microstructures comprised in the wound closure devices disclosed herein may be manufactured using any method available to the skilled artisan. In some embodiments, the microstructures are made by microfabrication processes that are based on established methods e.g., those used to make integrated circuits, electronic packages and other microelectronic devices, augmented by additional methods used in the field of micromachining and micromolding.

Arrays of microstructures can be fabricated, e.g., using combinations of replica molding; injection molding; microlithography; die cutting and etching; cutting; laser cutting; etching such as have been described, e.g., in WO2007127976A2; WO2002072189A2; WO2002064193A2; U.S. Pat. Nos. 6,503,231 and 6,334,856, WO1999064580 and WO2000074763; WO2012167162, all of which are incorporated herein by reference. For example, but not to be limited, microstructures can be fabricated by (i) etching the microstructure directly, (ii) etching a mold and then filling the mold with a melt or solution comprising the microstructure material to form the microstructure product, or (iii) etching a microstructure master, using the master to make a mold, and then filling the mold to form the microstructure replica (of the master). In some particular embodiments, the microstructures are manufactured according to the technique outlined in FIGS. 1a to 1f and described in Example 1. Briefly, a master of the desired dimensions is made with a metal, silicon, or a polymer via micromachining, microlithography, etching, laser cutting, or a combination thereof. The master is replicated using a polymeric material—e.g., silicone. The silicone is then lifted out of the master and is filled with a solution or a melt of the microneedle material, the filling may occur by e.g., drop casting or spraying. After curing or drying of the solution or melt the microneedles are lifted out from the mold.

Backing

Embodiments of the present invention relate to wound closure devices comprising one or more of a variety of microstructures, said microstructures optionally being affixed to a backing. Accordingly, in some embodiments, one or more microstructure arrays are affixed to a backing, said microstructures optionally comprising a variety of sizes, dimensions, and geometries. Any suitably backing may be used in the fabrication of the present devices, and in some embodiments the backing is optionally flexible and/or stretchable. The backing is a separate component, upon which the microstructures are affixed, e.g., via attachment of a base that comprises one or more microstructures, or via direct attachment of one or more individual microstructures onto the backing Such a base typically comprises two substantially planar surfaces, i.e., an upper surface and a lower surface; wherein one or more microstructures protrude perpendicularly or at an angle from the upper of said surfaces, and the lower of said surfaces is substantially flat. In such an instance, the backing may be affixed to the lower surface by any suitable means, e.g., by gluing.

Accordingly, the wound closure devices of the present invention may be provided with or without a backing attached. For example, the devices of the present invention may be provided in a ready to use form, wherein one or more microstructure arrays are affixed to a backing according to the present disclosure. Furthermore, some of the wound closure devices of the present invention do not comprise a backing, but instead comprise one or more microstructures or microstructure arrays on a suitable base, e.g., a base comprising flexibility, stretchability, or flexibility and stretchability, such that the device can perform its intended function on its own. Alternatively, it is also contemplated that a wound closure device according to the present invention may be packaged for commercial use with one or more suitable unattached backings, said backings optionally comprising different shapes, sizes, or compositions, such that one or more appropriately sized backings may be selected specifically to treat a certain type of wound. One or more microstructure arrays, provided in such a package, may then be attached to the backing as needed, to generate a wound specific device. Accordingly, such a device may optionally come with one or more attachment means, such as, e.g., an adhesive; wherein the attachment means may optionally be comprised on one or more components of the device, or it may be provided separately, e.g., in a package or container.

Suitable backing for use in the present devices include those which are transparent, or substantially transparent, thus allowing for non-invasive monitoring of wound healing, as well as backings that are not transparent. In some embodiments, backings are in the form of sheets; bandages; rolls; films; cloths; woven materials; or other permeable, semi-permeable, or impermeable coverings. The backings may be made from natural, synthetic, and/or artificial materials; and in some particular embodiments, they comprise a polymeric substance (e.g., a silicone, a polyurethane, or a polyethylene). The backing may comprised of materials that are nontoxic, biodegradable, bioresorbable, or biocompatible. In some embodiments, the backing comprises inert materials, and in other embodiments, the backing comprises activated materials, (e.g., activated carbon cloth to remove microbes, as disclosed in WO2013028966A2).

In some embodiments, the backing further comprises elastic properties, wherein the elasticity may optionally be similar throughout the device, or it may be varied along or across the device. Accordingly, in some embodiments, the backing comprises a material singularly, or in combination, selected from the group consisting of medical tape, white cloth tape, surgical tape, tan cloth medical tape, silk surgical tape, clear tape, hypoallergenic tape, silicone, elastic silicone, polyurethane, elastic polyurethane, polyethylene, elastic polyethylene, rubber, latex, Gore-Tex, plastic and plastic components, polymers, biopolymers, and natural materials.

In some certain embodiments, the present invention comprises a wound closure device, as disclosed herein, comprising one or more microstructures affixed to a commercially available backing selected from the group consisting of 3M Transpore Surgical Tape, 3M Blenderm Surgical Tape, Coverlet Fabric, Dynarex Silk Surgical Tape, Kendall™ Hypoallergenic Clear Tape, Tenderfix™ Hypoallergenic Cloth Tape, Curasilk™ Cloth Tape, Curapont, Leukosan Skinlink, Leukosan Strip, Leukostrip, Steri-Strip, Steri-Strip S, Urgo strip, and combinations thereof.

Devices

The wound closure devices of the present invention comprise one or more microstructures as described herein. The devices may have any suitable or desirable shape, size, or configuration. For example, devices of the present invention may in some embodiments have singularly, or in combination, a square, rectangular, round, oval, butterflied, or other shape; and in some embodiments, they may include sheets, tapes, rolls, or covers that can be cut or wrapped around, for example, a portion of a limb, to cover a wound on the limb.

In some instances the devices comprise generic features, according to the present specification, that enable the closure of a wide variety of wounds.

In certain embodiments, the devices comprise microstructures 700 microns to 1 mm in length.

In certain embodiments, the devices comprise microstructures that are 200 microns to 400 microns in width.

In certain embodiments, the devices comprise microstructures at angles of 40 degrees to 60 degrees.

In certain embodiments, the devices comprise arrays with a density of 10 to 100 microstructures per $cm^2$.

In some instances, components of the various devices are designed, accordingly to the specifications disclosed herein, to specifically optimize a device for treating a particular wound, tissue type, or location of the body. Accordingly, various specifications, e.g., the microstructure type, geometry, size, specifications, spacing within an array, array structure, number of arrays, location of arrays, dimension of arrays, isthmus, materials of the various components, etc., may in some instances be carefully chosen to design a wound closure device e.g., to treat a specific type of wound, or for treatment of any wound located on a particular type of tissue or location on the patient. For example, but not to be limited in any way, treatment of wounds on the palm or back may need longer needles than would be required to treat a wound on the face, due to the inherent variety of skin thickness that exists in these (and other) different sites of the body. In addition, the treatment of wounds may require shorter needles in patients, who are elderly or have chronic medical conditions or skin conditions, or patients treated with drugs, such as steroids, that are known to result in thinning of the skin. As such, the wound closure devices may comprise any suitable shape and size to adequately cover a variety of wounds. Additionally, the devices may be of any length or width suitable to cover a single wound, or optionally a plurality of wounds (such as, e.g., a tape bandage).

The devices have an aspect ratio defined in relation to the position on the device to be positioned above a wound (e.g., the isthmus). The length is defined as the dimension of the device extending perpendicularly away from the wound. The width is defined as the dimension of the device extending parallel to the wound. In one embodiment the aspect ratio of the device is from 0.1 to 10. In one embodiment the aspect ratio of the device is from 0.4 to 3. In one embodiment the aspect ratio of the device is from 1 to 5. In one embodiment the aspect ratio of the device is from 2 to 3.

Wound closure devices are removed when the wound is closed and shows sufficient healing. This varies for different body sites, such that sutures and other devices are removed 3-5 days, 6-10, and 11-14 days on the head (including face and neck), extremities, and trunk, respectively. Unexpectedly, it has been determined that the wound closure microneedle prototype devices led to accelerated healing of wounds compared to closure of wounds with sutures. See Example 5. More rapid closure of healing is beneficial to patients because it decreases the risks of infection, wound dehiscence, and other adverse events, and also enables patients to return to activities of daily living at an earlier time. In addition, accelerated healing is of benefit to patients with chronic medical conditions or skin conditions, or patients treated with drugs, such as steroids, that are associated with delayed healing of wounds.

To avoid infection, it is beneficial that the wound closure devices of the present invention be sterile prior to application to the skin or tissue. Accordingly, in one embodiment, the wound closure devices are sterile when packaged. In another embodiment, the wound closure devices are sterilized immediately prior to use. Many suitable means of sterilization are known and common in the art, and any such means is suitable for sterilizing the wound closure devices, provided said sterilization does not destroy the device. Such means may include, but are not limited to sterilization by heat, radiation, or chemical agents.

Furthermore, a plurality of wound closure devices, as described herein, may be connected to one another such that more than one of the devices can be applied to a wound at the same time. Such a connection may be at any suitable location on the device, and will of course vary depending on shape and intended use of the particular device. A non-limiting example of such an arrangement includes, e.g., a plurality of rectangular-shaped devices connected together via one or both sides that run perpendicular to the wound; such that a plurality of connected wound closure devices may be applied simultaneously in parallel, wherein each device is situated perpendicular to the wound, and the plurality of devices extends along the longitudinal axis of the wound like railroad ties along a track.

The devices of the present invention may optionally comprise adhesives to assist in the application of the device, and/or to help maintain the device in the position that it is applied to. Furthermore, the devices may comprise adhesive which binds a microstructure array to a backing e.g., via the direct binding of a base portion to a backing, as is described more thoroughly in the "backing" section. These various adhesives may be the same throughout the device, or more than one adhesive may be comprised in the device, e.g., one adhesive may be used to bind an array to the backing, and another adhesive may be used to bind the device to the skin or tissue of a patient. Furthermore, adhesive covers may be used, wherein the adhesive may again be the same as the adhesive that is optionally comprised on the other various components of the device, or wherein the covers comprise a different adhesive than the other various components of the device. Accordingly, the devices may comprise one or more types of adhesives.

In some instances, the device is a single base comprising a plurality, of microstructures fashioned into one or more arrays. In such an embodiment, the microstructures may be evenly spaced throughout an array, or they may be unevenly spaced, e.g., one non-limiting embodiment comprises a single base comprising at least two arrays, wherein the arrays are separated by an isthmus. Alternatively, the device may comprise one or more bases; each base comprising a plurality of microstructures fashioned into one or more arrays; wherein the bases are attached to a backing according to the present disclosure. In even other instances the microstructures are affixed to a backing or base, e.g., via attachment of the individual microstructures.

Microstructure Arrays on the Devices

In some embodiments, the wound closure devices of the present invention comprise only one microstructure array. In one embodiment, the wound closure devices comprise two microstructure arrays (e.g., separated by an isthmus). In certain embodiment, the wound closure devices comprise a plurality of microstructure arrays. In particular embodiments, the wound closure devices comprise from two to 100 microstructure arrays.

Pluralities of arrays may be separated from one another by any appropriate spacing, which may or may not be the same throughout the device. In some embodiments, array spacing ranges from approximately 30 μm to 1 cm. Accordingly, array spacing may be approximately 30 μm, 50 μm, 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1 mm, 1.5 mm, 2 mm, 3 mm, 5 mm, 7 mm, 10 mm, or higher, including all integers (e.g., 31 μm, 32 μm, 33 μm, etc.) and ranges (e.g., 100-1000 μm, 500 μm-10 mm, 700 μm-1 mm, etc.) in between, of the microstructure heights set forth herein. In one embodiment, the array spacing is from 2 to 10 mm. In another embodiment, the array spacing is from 4 to 10 mm.

The arrays may be evenly, or unevenly spaced apart, e.g., directionally varied. In particular embodiments, at least two arrays are comprised on the device, said arrays optionally being separated by an isthmus; while in other embodiments no such isthmus separates the arrays. In further embodiments, the device may comprise a plurality of arrays on one or either side of an isthmus, said plurality of arrays being optionally evenly spaced apart from one another on each side of the isthmus, or not evenly spaced. In some embodiments, an equal number of arrays are on either side of the isthmus, and in other embodiments an unequal number of arrays are on either side of the isthmus.

In some embodiments, the wound closure devices of the present invention comprise two or more arrays comprised on a base, and/or optionally affixed to a backing, wherein the arrays are separated by an isthmus. In certain embodiments the isthmus is not stretchable, while in other embodiments it is stretchable. As a non-limiting example, one such device comprises two arrays affixed to a backing, said arrays being separated by a non-stretchable isthmus; wherein the space comprising the arrays is not stretchable (e.g., FIGS. 13a to 13e). Another non-limiting example of such a device in shown in FIGS. 15a to 15e, wherein the device comprises two arrays affixed to a backing, and separated by an isthmus that is not stretchable. Furthermore, examples of such embodiments are shown in FIGS. 18a to 20, as applied to human and synthetic skin.

In some embodiments, the device comprises two or more arrays that are not separated by an isthmus. Accordingly, two or more arrays may optionally be immediately adjacent to one another, thus having no space or substantially no space separating the arrays. A non-limiting example of such a device may comprise two separate microstructure arrays, each array having its own base, and each array being separated from one another by a distance that is equal to, or less than, the pitch of their microstructures. Accordingly, such wound closure devices may be used to close or secure a wound, wherein the microstructures comprised on the two or more arrays are located all the way up to the wound's edge.

Similarly, the present invention provides for devices comprising only one microstructure array, wherein a wound is closed or secured via application of the device directly over the wound, such that some of the microstructures comprised in the single array are secured on one side of the wound, and some of the microstructures comprised on the same array are secured on the other side of the wound. Furthermore, the wound may be closed with a device comprising only one microstructure array, said array being longer and wider than the wound such that the microstructure array completely covers the wound, so that microstructures are present on substantially all sides of the wound, and are also optionally also penetrating into the wound.

In particular embodiments, the wound closure devices of the present invention comprise a plurality of microstructure arrays comprised on a base, and/or optionally affixed to a backing, such that at least one microstructure array is capable of penetrating into or grasping skin or tissue on one side of a wound, and at least one other microstructure array, which is optionally separated from the first array by an isthmus, is capable of penetrating into or grasping skin or tissue on another side of the wound. In some embodiments, the device comprises a flexible and stretchable backing Such a device may be stretched across a wound site by using fraction and the grip of the microstructures onto the skin of a subject. Embodiments such as this may optionally comprise a backing or isthmus that comprises elasticity, such that the retractile force of the device helps to secure the device in place, and/or assists in the closing the wound. In this way, in certain embodiments, the wound closure devices of the present invention are able to pull together the skin directly adjacent to a wound, such that the wound is closed or substantially closed, or optionally everted. In other embodiments, the device is not substantially stretchable, and thus it is applied to a wound that is closed by other means (e.g., suturing or with forceps) so as to secure the wound in its already closed position.

The arrays may be any appropriate shape, and in particular embodiments they comprise rounded edges, so as to reduce the induction of irritation and to limit accidental removal, as described above with regard to the shapes of the backings.

Device Areas and Densities

The wound closure devices can be any area suitable for a particular application. Large device areas are used for large wounds and small devices are used for small wounds.

In one embodiment, the device is less than 0.5 $cm^2$ in area. In one embodiment, the device is less than 1 $cm^2$ in area. In one embodiment, the device is less than 1.5 $cm^2$ in area. In one embodiment, the device is less than 2 $cm^2$ in area. In one embodiment, the device is less than 3 $cm^2$ in area.

The devices contain a density of microstructures per unit area. In certain embodiments, the microstructure density is uniform throughout an array or device. In another embodiment, the microstructure density is not uniform.

In one embodiment, the device is less than 0.5 $cm^2$ in area and contains 2-20 microstructures. In one embodiment, the device is less than 1 $cm^2$ in area and contains 6-50 microstructures. In one embodiment, the device is less than 1.5 $cm^2$ in area and contains 10-100 microstructures. In one embodiment, the device is less than 2 $cm^2$ in area and contains 20-200 microstructures. In one embodiment, the device is less than 3 $cm^2$ in area and contains 50-300 microstructures.

Head and Neck Devices

Given that the largest fraction of skin biopsies and lacerations occur on the head, neck, and face, and the superior wound closure capabilities of the disclosed devices, in certain embodiments the devices are configured for relatively small-scale wound closure. In certain such "head and neck" devices, relatively short microstructures (e.g., microneedles) are used to minimize inflammation and be able to penetrate the thin skin of the head, face, and neck compared to other skin sites such as the back and extremities. Examples of head and neck devices have lengths and widths of between 0.5 and 2 cm. Such a compact form comes from relatively small arrays and a short, or no, isthmus.

In one embodiment, the microstructure spacing is from 1-3 mm.

In one exemplary embodiment, the head and neck device has the following characteristics: 1 cm×0.6 cm device: two arrays each being 3-4 mm in length and 0.6 cm in width with 2-6 microstructures (e.g., microneedles) on each array, and an isthmus of 2-3 mm in length.

In one exemplary embodiment, the head and neck device has the following characteristics: 1 cm×1 cm device: two arrays each being 3-4 mm in length and 1 cm in width with 6-40 microstructures (e.g., microneedles) on each array and an isthmus of 2-3 mm in length.

In one exemplary embodiment, the head and neck device has the following characteristics: 1.5 cm×1 cm device: two arrays each about 5-6 mm in length and 1 cm in width with 10-60 microstructures (e.g., microneedles) on each array and an isthmus of about 5 mm in length.

In one exemplary embodiment, the head and neck device has the following characteristics: 2 cm×1 cm device: two arrays each about 6-8 mm in length and 1 cm in width with 15-100 microstructures (e.g., microneedles) on each array and an isthmus is 6-8 mm in length.

It will be appreciated that additional head and neck devices are contemplated that include any device size, microstructure type, array type, and related characteristics.

Roll Bandage

In some embodiments, the wound closure device of the present invention is in the form of a roll. Roll wound closure devices according to the present invention are in some embodiments akin to a roll bandage, with the important addition of the wound closing microstructure arrays. Such microstructure array roll bandages comprise a slender, elongated shape, and are formed into a roll. They comprise various lengths and widths, a longitudinal axis, and a wound-facing isthmus extending along the longitudinal axis (typically in the midline of the longitudinal axis), that is over the wound when the microstructure array roll bandage is being applied.

In certain embodiments, the microstructure array roll bandages each comprise three parallel longitudinal portions that are slender and elongated and include a middle portion (the wound facing isthmus) that extends along the longitudinal axis of a backing upon which the microstructure arrays are affixed. Such bandages further comprise two exterior portions that extend along the longitudinal axis of the backing, each of said two exterior portions comprising one or more microstructure arrays extending along the length of the bandage. In some embodiments, the bandage comprises one long array of microstructures extending along the longitudinal axis, and in other embodiments a plurality of microstructure arrays are comprised upon this axis.

In another similar embodiment, the microstructure array roll bandages do not comprise a backing, but instead are comprised of microstructures on a base. Such a bandage may comprise three parallel longitudinal portions that are slender and elongated and include a middle portion (the wound facing isthmus) that extends along the longitudinal axis of a base upon which the microstructure arrays are affixed. Such bandages further comprise two exterior portions that extend along the longitudinal axis of the base, each of said two exterior portions comprising one or more microstructure arrays extending along the length of the base. In some embodiments, the bandage comprises one long array of microstructures extending along the longitudinal axis, and in other embodiments a plurality of microstructure arrays are comprised upon this axis.

As is the case with all of the devices of the present invention, roll bandages may optionally comprise other drugs or therapeutics, e.g., upon or along the isthmus; and likewise they may also optionally comprise adhesive, e.g., directly comprised on the backing or base, or optionally comprised on tabs or strips protruding along the external portion of the backing or base, said tabs or strips optionally being removable, e.g., easily tearable due to perforations.

Targeted at, for instance, over-the-counter (OTC) users of bandages such as, e.g., BAND-AIDs®, further embodiments may include a glueless wound closure device, which is based on the present microstructure technology. Such embodiments may be used as alternatives to traditionally available bandages attached to the skin with adhesive. Such embodiments may take the form and shape of typical adhesive attached bandages. These products can serve the needs of patients, who suffer minor cuts and burns in which bandages are used today. Further embodiments provide for devices such as these, comprising other components to aid in the attachment of the devices, e.g., nanostructures such as nanofibers. One such non-limiting example comprises the addition of a chitin nanofiber coat to the backing or to the microstructures. Due to their small size, these nanostructures add surface area to the device, increasing the overall contact with the wound or the surrounding tissue or skin. Accordingly, the added surface area induces a glueless adhesion, assisting in the proper placement and adherence of the device.

The devices of the present invention may further comprise a variety of ornamental designs. In some embodiments, the devices are substantially transparent, while in other embodiments they are not. Particular embodiments provide for devices as disclosed herein that comprise a color or pattern, e.g., an animal print or themed design.

Optional Components

In particular embodiments, in addition to the microstructure arrays described above, the wound closure devices of the present invention may further comprise nanostructure arrays and/or nanofiber coatings upon the microstructures. In such embodiments, the nanofiber coated microstructure surfaces, or the nanostructure arrays, can increase the surface area of the devices, thus in turn leading to increased contact of the device with the skin or tissue to which it is applied. As a result, the devices may stick more efficiently, further promoting glueless adhesion, thus obviating the need for adhesive components. Accordingly, in some particular embodiments, the microstructures of the present invention are comprised of, or coated with, chitin nanofiber ink, as disclosed in the co-owned PCT application (PCT/US2012/040565, herein incorporated by reference in its entirety).

In some embodiments the wound closure devices of the present invention comprise a visual stress indicator on the base or flexible backing. In certain embodiments, the stress indicator is a painted strip or several painted strips that change color upon extension of the device.

In still further embodiments, the devices disclosed herein may include one or more additional components that are provided to, for example, reduce pain, improve healing, reduce adhesion to the wound, prevent infection, reduce itching, or otherwise aid in improving patient comfort. Such additional components are described below and can be incorporated into the wound closure devices of the present invention in any suitable location (e.g., on an isthmus or on one or more arrays), or they can alternatively be provided and/or used to treat a wound prior to the application of the present wound closure devices.

In some embodiments the wound closure devices of the present invention further comprise a hydrogel. The hydrogel may be comprised of any substance. Some embodiments provide for hydrogels comprising, consisting essentially of, or consisting of an inert substance, or mixtures of inert substances. In some embodiments, the hydrogel comprises a biopolymer. In certain embodiments, the hydrogel comprises a biologically active substance, and some particular embodiments, the hydrogel comprises a biologically active substance that is able to induce or promote wound healing. In one embodiment, the hydrogel comprises chitin, chitosan, or a mixture of chitin and chitosan. In certain embodiments, the wound closure devices of the present invention comprise hydrogels as described herein, wherein the hydrogel is connected to the flexible backing Hydrogels may be connected to the backing in any suitable location. In some particular embodiments, the hydrogel is connected to an isthmus. In some particular embodiments, the hydrogel is connected to a flexible backing in a space within a microstructure array, e.g., between at least two microstructures. In some particular embodiments the hydrogel is directly connected to one or more microstructures, e.g., as a coating.

In some embodiments, other healing agents are optionally comprised on, or used with the wound closure devices, such as, e.g., chitosan, chitin, alginates, silver, silicone, iodine, antimicrobials, cytokines, growth factors, honey, leptospermum honey, polyhexamethylene biguanide, methylene blue, gentian violet, and combinations thereof. Accordingly, in such embodiments, these other agents may be optionally applied to the wound or the device by the user, prior to the application of the device. Alternatively, in some embodiments these other agents may be comprised on the device as packaged (e.g., on an isthmus or on an array). The agents may be applied in the form of a powder, cream, gel, ointment, or other formulation know to those of skill in the art.

Covers

Some embodiments of the present invention provide for the optional application of one or more protective covers over the top of the wound or wound closure device; e.g., to provide additional protection to the wound from the surrounding environment, and to help maintain the device securely in its intended position. Indeed, we have found that in some embodiments the devices are much more strongly secured in their intended position when covered in this manner. In principle, any cover will suffice. In some embodiments, optimal covers will be such that they are able to apply additional downward force upon the device to ensure the microstructures remain in place and to prevent unintentional removal of any of the microstructures. The covers may be any appropriate shape, and in particular embodiments they comprise rounded edges, so as to reduce the induction of irritation and to limit accidental removal, as described above with regard to the shapes of the backings.

In some embodiments, the cover comprises adhesive, while in other embodiments it does not. The adhesive may optionally be such that it sticks permanently to the device, but temporarily to the skin or tissue, such that any attempt to remove the cover will result in a simultaneous removal of the device. In such an instance, the device and/or cover may optionally be replaced with a new device and/or cover if necessary. In some embodiments, the cover may be designed such that it does not permanently adhere to the device, but it can instead be removed and optionally replaced with another cover without disturbing the placement of the device on the wound. Alternatively, one can remove such a temporary cover so as to replace one or more of the devices. Of course, a new cover can then optionally be applied such as needed. In other embodiments, only a portion of the cover contains adhesive, such as described herein.

In some embodiments the cover may be optionally flexible and/or stretchable. In some embodiments, the cover is transparent, or substantially transparent, thus allowing for non-invasive monitoring of wound healing; while in other embodiments the cover is not transparent. In some embodiments, the covers are in the form of sheets; bandages; films; or other permeable, semi-permeable, or impermeable coverings. The covers may be made from natural, synthetic, and/or artificial materials; and in some particular embodiments, they comprise a polymeric substance (e.g., a silicone, a polyurethane, or a polyethylene). In some embodiments, the cover is comprised of materials that are nontoxic, biodegradable, bioresorbable, or biocompatible. In some embodiments, the cover comprises inert materials, and in other embodiments, the cover comprises activated materials. In some embodiments, the cover further comprises elastic properties, wherein the elasticity may optionally be similar throughout the cover, or it may be varied along or across the cover. Furthermore, in some embodiments, the covers comprise adhesive; while in other embodiments they do not. Accordingly, in some embodiments, the cover comprises a material singularly, or in combination, selected from the group consisting of tape (e.g., medical tape, white cloth tape, surgical tape, tan cloth medical tape, silk surgical tape, clear tape, hypoallergenic tape), silicone, elastic silicone, polyurethane, elastic polyurethane, polyethylene, elastic polyethylene, gauze, gel, hydrogel, silk, chitin, chitosan, cellulose, alginate, foam, shrink wrap, sheets, and hydrocolloids.

In particular embodiments, the cover is a commercially available cover selected from the group consisting of Brown Medical—Sealtight Shower Dressing Protection Patch; Smith & Nephew Coversite Composite Cover Dressing; Coloplast Comfeel Plus Hydrocolloid Clear Thin Dressing; Systagenix Nu-Derm Bordered Hydrocolloid Wound Dressing; 3M Tegaderm Hydrocolloid Dressing; Smith & Nephew Replicare Thin Hydrocolloid Dressing; Smith & Nephew Replicare Hydrocolloid Wound Dressing; Hollister Restore Sterile Hydrocolloid Dressing; Hollister Restore Hydrocolloid Dressing with Foam; Backing; Hollister Restore Plus Hydrocolloid Dressing with Tapered Edge; Kendall Polyskin II Transparent Dressing; Smith & Nephew AlgiSite M Calcium Alginate Dressing; Kendall Curasorb Calcium Alginate Dressing; Deroyal Kalginate Calcium Alginate Dressing; Smith & Nephew Cica-Care Silicone Gel Sheeting; Molnlycke Mepiform Safetac Self Adherent Dressing with Soft Silicone for Scar Reduction; Molnlycke Mepitel Safetac Transparent Wound Contact Layer; Smith & Nephew OpSite Flexifix Transparent Film Roll; Systagenix Select Bioclusive Transparent Wound Dressing; Systagenix Select Bioclusive Transparent Wound Dressing; 3M Tegaderm Transparent Dressing First Aid Style; 3M Tegaderm Clear Absorbent Acrylic Dressing; Hartmann Cosmopore Adhesive Wound Dressing; 3M Tegaderm Transparent Film Dressing with Border; Kendall Telfa Sterile Clear Wound Dressing; Smith & Nephew Allevyn Thin Gentle-Adhesive Polyurethane Dressing; and combinations thereof.

In some embodiments the cover is comprised in a roll, optionally comprising adhesive. In some embodiments the roll bandages may be covered by an adhesive cover, e.g., an adhesive roll cover. In other embodiments, the roll bandages are covered by a plurality of adhesive covers, e.g., a plurality of sheet covers.

In some embodiments, the wound closure devices are disposable. Accordingly, disposable devices may contain components that make it not possible to apply more than once. For example, but not to be limited in any way, disposable devices may comprise a backing or wound cover that contains adhesive material that is not adherent once removed from the skin. In another non-limiting example, an adhesive cover may be used, wherein following application, the cover is designed to adhere to the wound closure device in such a way that they cannot be separated from one another without destroying the device. In another non-limiting example, the microstructures may be made of biodegradable material. Such disposable designs may prevents the risk the device being used on more than one patient, which can result in transmission of infectious agents; and will also reduce the risk of reapplication on the same patient, which may increase the risk of infection.

Packaging

The wound closure devices of the present invention may be packaged individually, e.g., in a single use stand alone package, or alternatively, a plurality of the devices may be packaged together in any way, e.g., in a receptacle containing a plurality of individually packaged single use wound closure devices, or e.g., in a roll comprising a plurality of devices (optionally individually packaged) and separated by a cuttable or tearable connecting portion. Accordingly, some embodiments provide for a roll comprising a plurality of individually packaged wound closure devices, as described herein, wherein each of the individually packaged devices are connected to at least one other individually packaged device via a perforated connecting portion, thus enabling the easy separation of one of said individually packaged bandages.

In some embodiments, a plurality of the wound closure devices of the present invention may be packaged together in the form of a roll; or alternatively the wound closure device may be a microstructure array bandage, as described herein. Accordingly, the present disclosure also provides for a roll-on, handheld dispenser to assist in the easy application of the present wound closure devices. Although applicable in the at-home setting, this embodiment is specifically designed with the surgical market in mind (e.g., specifically urgent care settings, such as emergency rooms and operating rooms where time is of the utmost importance). With rapid single hand operation, such an embodiment offers significant advantages over sutures, which require precious time to use, or Steri-Strips, which are difficult to handle and are only able to close minor wounds.

The design of such embodiments may be compared to white tape dispensers used to correct errors on paper. This embodiment may contain a roll kept in a sealed enclosure to ensure its sterility. Tapes or bandages can have various widths tailored to the needs of various medical and other uses. For instance, such tapes or bandages may have widths of 0.5 cm, 1 cm, or more. By applying the device with the dispenser to the wounded area, the provider of medical care will be able to rapidly use this embodiment with its strong mechanical and adhesive properties to secure wound closure without painful sutures. The microstructure technology will ensure that, upon contact with the patient skin, the microstructures will adhere and allow for dispending further material. The microstructures will be designed to minimize adhesion to the back (the surface that is away from the skin) of the microstructure roll to ensure rapid and convenient delivery. A microstructure dispenser according to the present invention may include a means for cutting specifically designed to cut the microstructure tape or roll without damaging the patient skin. In some embodiments, the blade can be placed at an angle that allows for microstructure tape cutting upon an upward rotation of the medical care provider's hand. This single hand operation will afford speed and accuracy of the closure of wounds. The medical care provider will be able to use the other hand to ensure skin planarization during wound closure. Not only is this more convenient for the medical care provider, but it also eliminates the need for other medical personnel to assist the surgeon in carrying out wound closure.

Wound Closure System Kit

In some embodiments the devices of the present invention are provided as a wound closure system, which is a kit comprising at least one wound closure device, as described herein, and at least one other component that can optionally be used with the device, e.g., to improve wound healing capabilities. Kits such as these may comprise one or more of the wound closure devices disclosed herein, as well as one or more other optional components such as, e.g., one or more covers (optionally comprising adhesive) to be applied over the wound closure device; one or more containers (e.g., bottles, pouches, packets, tubes) comprising a drug or therapeutic, cleansing and/or sterilization means (e.g., antiseptics, antibiotics, sterile saline), analgesics (e.g., Benzocaine or Lidocaine), which can optionally be applied to the wound prior to the application of the device; and instructions for using the wound closure devices.

In such embodiment, a wound closure system comprising one or more of the presently disclosed wound closure devices, and optionally comprising one or more of the aforementioned optional components, further comprises chitin and/or chitosan. Chitin and chitosan alike: 1) promote healing, 2) are anti-bacterial, 3) prevent bleeding (hemostasis), 4) decrease inflammation, 5) reduce scarring, 6) absorb fluids such as exudate, and 7) are breathable; thus their addition to a wound prior to closure can significantly improve the healing process. The chitin or chitosan may be in any suitable form, and in some embodiments they are in the form of a powder, a gel, a cream, or an ointment. The chitin or chitosan may be applied to the wound or device prior to the application of a wound closure device, such that the natural healing properties of these products may promote healing. Alternatively, the device may come packaged with the chitin or chitosan already on the device at any suitable location, e.g. on or around the microstructures or on an isthmus.

In one particular embodiment, the kit may comprise one or more microstructure arrays (separate from a backing); one or more backings (e.g., optionally different kinds of backings upon which the arrays can be affixed), thus enabling the user flexibility to tailor the exact design of the device to the specifications of a particular wound); a means for attaching one or more of the arrays to one or more of the backings (e.g., a glue); a cover; and chitin or chitosan (e.g., in the form of an ointment, gel, cream, or powder).

In another particular embodiment, the kit may comprise one or more microstructure arrays affixed to a backing; a cover; and chitin or chitosan (e.g., in the form of an ointment, gel, cream, or powder).

In another embodiment, the kit comprises a cutting instrument (e.g., disposable scissors) configured to cut the devices, arrays, and/or backings, such that is possible for a user to individually fabricate an array to the desired dimensions. This enables the user to tailor the wound closure device to the specific dimensions and other characteristic of an individual wound.

Additionally, all kits optionally further comprise instructions for use of the present devices.

Use of the Devices

The wound closure devices of various embodiments can be used to treat any kind of wound including acute and chronic wounds, such as, e.g., lacerations, cuts, scrapes, abrasions, post-operative wounds (e.g., caused by minimally invasive surgery, laparoscopic surgery, robotic surgery, incisional biopsies, general surgery, and cosmetic surgery), denuded skin, burns, ulcers (e.g., diabetic ulcers, ulcers from vascular insufficiency, pressure sores), or other skin problems (e.g., allergies, eczema, dermatitis, and psoriasis). Accordingly, wound closure devices of various sizes can be prepared such that minor wounds as well as larger wounds can be treated using the devices of embodiments. In particular embodiments, the wounds treated with the devices of the present invention range from approximately 0.1 mm in length, to approximately 50 cm in length. Accordingly, in particular embodiments, the wound length is approximately 0.1 mm, 0.2 mm, 0.3 mm, 0.4 mm, 0.5 mm, 0.6 mm, 0.7 mm, 0.8 mm, 0.9 mm, 1 mm, 5 mm, 6 mm, 7 mm, 8 mm, 9 mm, 1 cm, 2 cm, 3 cm, 4 cm, 5 cm, 10 cm, 20 cm, 30 cm, 40 cm, 50 cm, or longer, including all integers and decimals (e.g., 9.1 mm, 9.2 mm, 9.3 mm, etc.) and ranges (e.g., 0.1 mm-50 cm, 0.5 mm-10 cm, 0.5 mm-5 cm, etc.) in between, of the wound lengths set forth.

The wound closure devices can be used to close an entire wound or a portion of a wound. Multiple wound closure devices of the same or different design may be used together to close a given wound. When a plurality of the wound closure devices are used to close a single wound, they may be placed immediately adjacent to one another (either running parallel or perpendicular to the wound), or they may be separated from each other at any suitable distance. Accordingly, the devices may be applied with no space between the arrays of two different devices, or they may be applied approximately 2 cm apart, or more. In particular embodiments, pluralities of wound closure devices are affixed to a wound according to the present disclosure with a spacing that ranges from about 2 mm to about 10 mm.

The wound closure devices can also be used in combination with other wound closure devices, such as sutures, staples, tissue adhesives, and bandages. The wound closure devices can also be used for temporary wound closure prior to closure with other devices, such as staples, sutures, or tissue adhesives. The wound closure devices can also be used after closure with sutures or staples. For example, this could enable earlier removal of sutures and staples, and thus reduce the risk of scarring related to these devices.

The wound closure devices can be used alone or with wound dressings, including transparent films, gauzes, hydrofibers, hydrogels, hydrocolloids, exudative absorbers, collagens, and alginates. The devices can also be used with impregnated dressings containing bismuth, petroleum, silver, and carboxymethylcellulose.

The wound closure devices disclosed herein may be applied in any suitable manner. For example, but not to be limited in any way, in some embodiments, wherein a wound comprises a length to width aspect ratio other than 1 (e.g., a laceration), the wound closure device may in one embodiment be applied perpendicularly, with respect to the longer portion of such a wound, thus bridging the slit of the wound, or alternatively, the devices may be applied parallel to the slit of the wound, e.g., wherein a microstructure array wound bandage roll is rolled over the wound. In still further embodiments, the devices of the present invention may be applied to such a wound at a diagonal, with respect to the slit of the wound. Additionally, as needed, some embodiments provide for the utilization of a plurality of the wound closure devices to treat a particular wound. In such embodiments, the devices may be applied to a wound in any appropriate manner, so as to achieve the desired wound closure effect. Non-limiting examples include, e.g., the application of two or more of the wound closure devices in parallel to one another, perpendicular to one another, or even criss-crossed over one another. In some embodiments the device is stretched across a wound, and in other embodiments the device is applied without stretching. In some embodiments the device is applied by hand, and in some embodiments the device is applied using an applicator or instrument, as described more thoroughly below. In some embodiments, multiple wound closure devices may be used to close an individual wound. Any number of devices may be used to close a given wound, in any orientation, and said devices may be spaced apart from one another at any appropriate distance, so as to achieve the desired wound closing effect.

Figure 16:
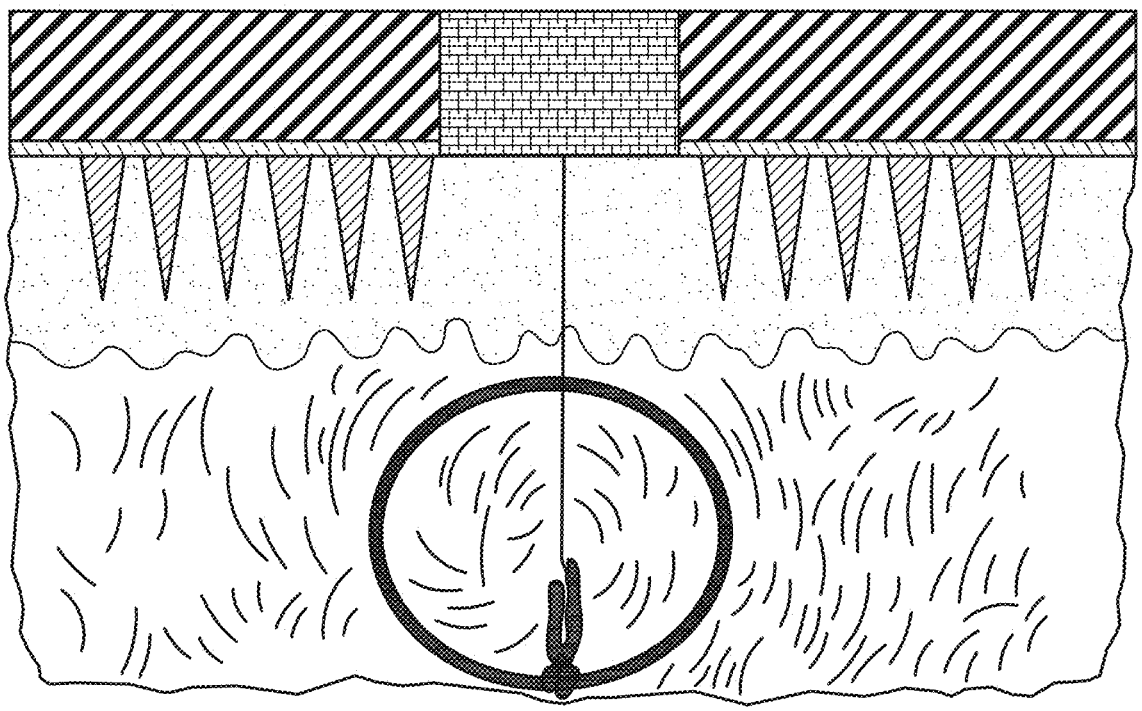
FIG. 16 shows a schematic representation of a wound closure device of the present invention applied to a wound (cross sectional view). In this embodiment, the microneedles penetrate through the epidermis and into the dermis keeping the wound closed. This is essentially the same action as a suture or a staple, but significantly less injurious to tissues. The deep tissue suture may or may not be required depending on the conditions of the wound.

In general, the wound closure devices of the present invention are capable of closing or protecting a wound, while optionally also enabling efficient and versatile delivery of drugs or therapeutic agents. FIG. 16 shows a schematic representation of a cross sectional view of a wound closure device applied to a wound. In this embodiment, relatively long microstructures are shown penetrating the epidermis and into the dermis of the adjacent skin on either side of the wound. In this way the wound is secured closed. Depending on the desired application, microstructures length can be varied e.g., using shorter microstructures to induce topical drug delivery to the epidermis, systemic delivery via microstructures long enough to penetrate the dermis, or various intermediate lengths to target drug or therapeutic delivery to particular dermal and epidermal sublayers. One skilled in the art is easily able to determine the necessary length of the microstructures to target a specific layer, a property that will vary depending on the location to which the device is intended to be used. For example, if targeting the dermal layer of the eyelid, one must account for microstructure lengths in the range of 0.3 mm. If however, one needs to target the dermal layer of the back, microstructures lengths must be an order of magnitude longer, e.g. 3 mm.

Accordingly, in some embodiments, the wound closure devices of the present invention provide their desired function in the absence of other known drugs or therapeutic agents, and in other embodiments, the devices provide their desired function in combination with other drugs or therapeutic agents. In some particular embodiments, the present invention provides for wound closure devices comprising e.g., hollow microstructures in which drugs or therapeutics can be incorporated e.g., as are described in U.S. Pat. No. 3,964,482, incorporated by reference herein in its entirety; porous microstructures; drug or therapeutic coated microstructures; and microstructures comprising slow release mechanisms for controlled drug or therapeutic delivery.

The wound closure devices described herein can be used to treat wounds on humans or any other animal including, but not limited to, mammals, fish, reptiles, birds, and other creatures. Thus, medical and veterinary uses for the wound closure devices described herein are encompassed by the invention, and such uses can be carried out by trained medical professionals, physicians, veterinarians, nurses, emergency medical technicians, and the like, or by consumers who purchase the devices described herein over the counter.

EXAMPLES

Example 1

Microstructure Fabrication

The following example outlines one of many suitable methods for producing microstructures and microstructure arrays according to the present specification. In this particular example, microstructures were produced using a replica molding technique that is commonly used within the art, and can be easily reproduced by the skilled artisan.

Figure 2A:
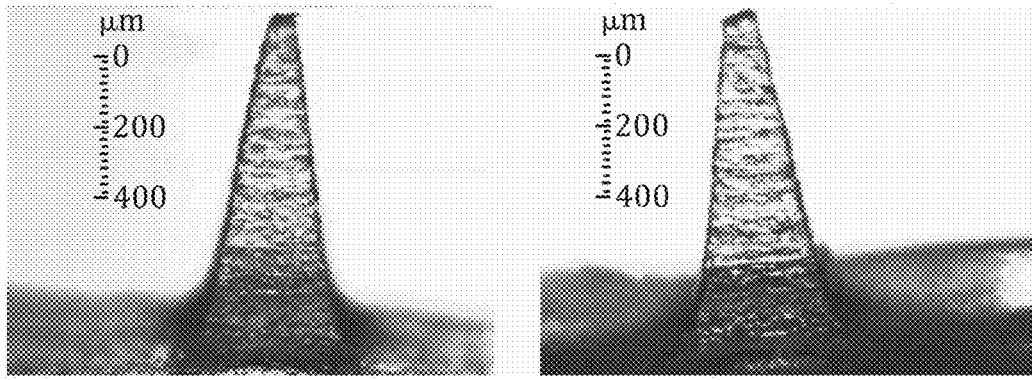
FIGS. 2a to 2c illustrate examples of microneedles made from a polymethylmethacrylate (PMMA) solution in acetone with replica molding of an aluminum master and a silicone mold. Microneedle dimensions are provided.
Figure 2B:
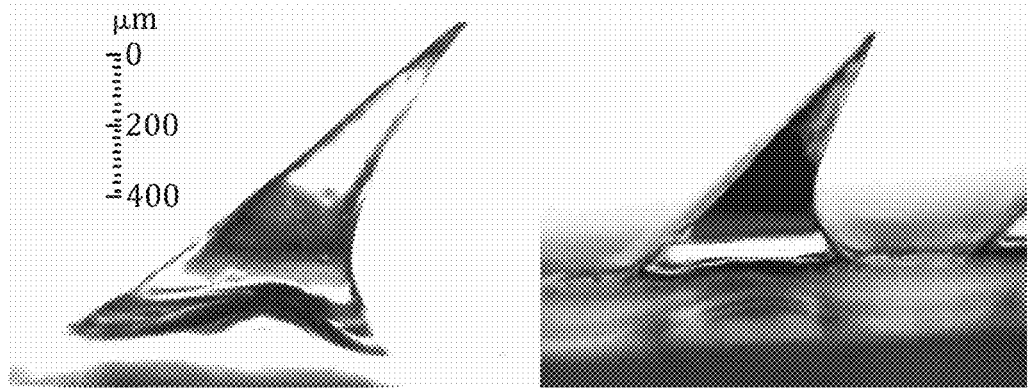
Figure 2C:
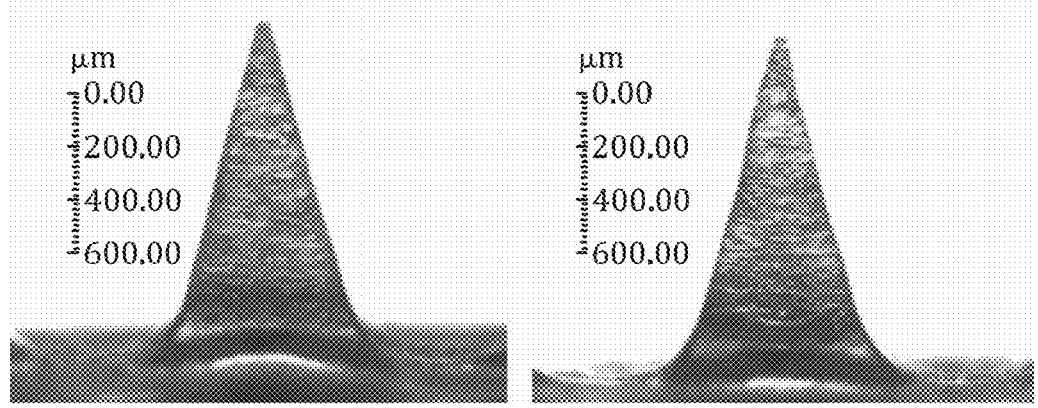

FIGS. 1a to 1f show a schematic demonstrating the main steps in this procedure. To begin, a master mold of the desired dimensions was made out of aluminum via micromachining and wet chemical etching. A polydimethylsiloxane (PDMS) mold (Sylgard 184 Silicone Elastomer Kit, Dow Corning Corporation, 3097358-1004) was prepared from the master by pouring the recently mixed components of the PDMS on top of the master inside of an aluminum foil box, desiccating for 15 minutes, and then allowing the components to cure on a hot plate at 110 C for 1 hour. PMMA (Sigma Aldrich 445746-500G) was dissolved in acetone to form a 10 wt. % solution and then poured over the mold with a 3 mm solution height. After drying for approximately 3 days, all of the acetone had vaporized and the microstructures were peeled from the mold and then stored in a cell culture dish until needed. Finally, microstructures were affixed to a Steri-Strip S piece by gluing with Loctite 4011 medical adhesive. FIGS. 2a to 2c are photographs of several different microstructures that were produced via this technique, with A and C being straight microneedles and B being angled microblades. FIGS. 7a, 7b, 12a, and 12b are images of non-limiting examples straight microneedle arrays and angled microblade arrays, respectively, each patterned in low density (FIGS. 7a and 12a) and in high density (FIGS. 7b and 12b); thus demonstrating some of the microstructure variety that can be produced via this method. FIGS. 14a to 14c and 17a to 17c show non-limiting prototype examples of wound closure devices comprising microstructure arrays produced via this method.

Example 2

Wound Closure Devices

The following example demonstrates a non-limiting selection of several wound closure devices we have made. In principle, microstructures can be easily fashioned into any conceivable shape using microfabrication techniques common to the art, e.g., via the replica molding method described in Example 1. Furthermore, although PMMA was used for all of the devices shown in this Example, a variety of microstructures and microstructure arrays were formed out of other material, (e.g., chitin), and one skilled in the art can easily fashion similar microstructures from a myriad of other materials such as, e.g., the various materials described in this specification, and hundreds of other materials known to the skilled artisan to be suitable for such microfabrication. Accordingly, it is without limitation that we present these particular embodiments, as an example of the specific versatility of this technique.

Prototype A.

Figure 17A:
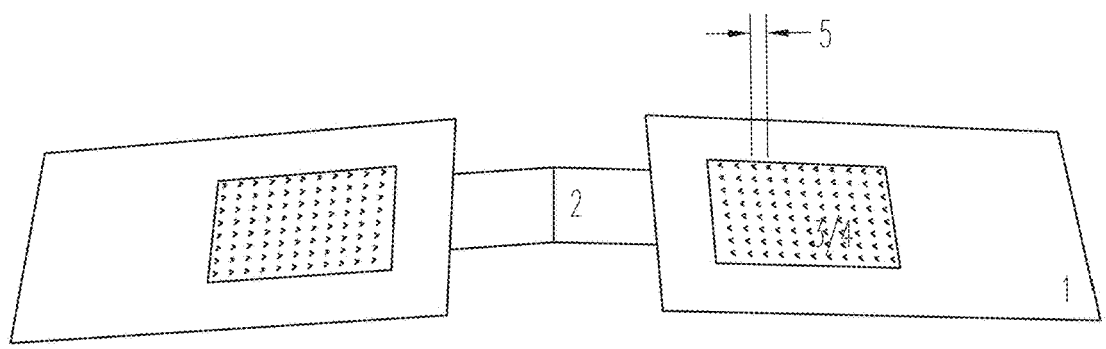
FIGS. 17a to 17c are photographs of three non-limiting examples of the present wound closure devices. Note the different sizes, shapes, and dimensions of the backings (1), isthmuses (2), bases (3), arrays (4), array spacing (5), etc.

These devices all comprised two microstructure arrays which were manufactured according to the method described in Example 1; wherein two bases, each comprising a single microstructure array were affixed to a polyurethane backing derived from Steri-Strip S material. The backings comprising the arrays were separated by a polyester filament isthmus. FIG. 17a shows a picture of one of these prototypes. In this picture, the backing materials are 1.5 cm wide×3 cm long. Arrays are 8 mm wide×12 mm long, comprising straight microneedles made of PMMA, which are 550 μm long, and uniformly distributed in the arrays. The isthmus is 15 mm long, with a 22 mm separation between the two microstructure arrays. During production of this prototype, many other models were made, varying different components such as, e.g., the isthmus length/distance between needle arrays; the placement of the needle arrays within the backing; the length of tabs on opposing sides behind the needle arrays; the presence or absence of adhesive on the tabs and/or on the isthmus areas; types of microstructures, size of microstructure arrays used, and density of microstructures.

Prototype B.

Figure 17B:
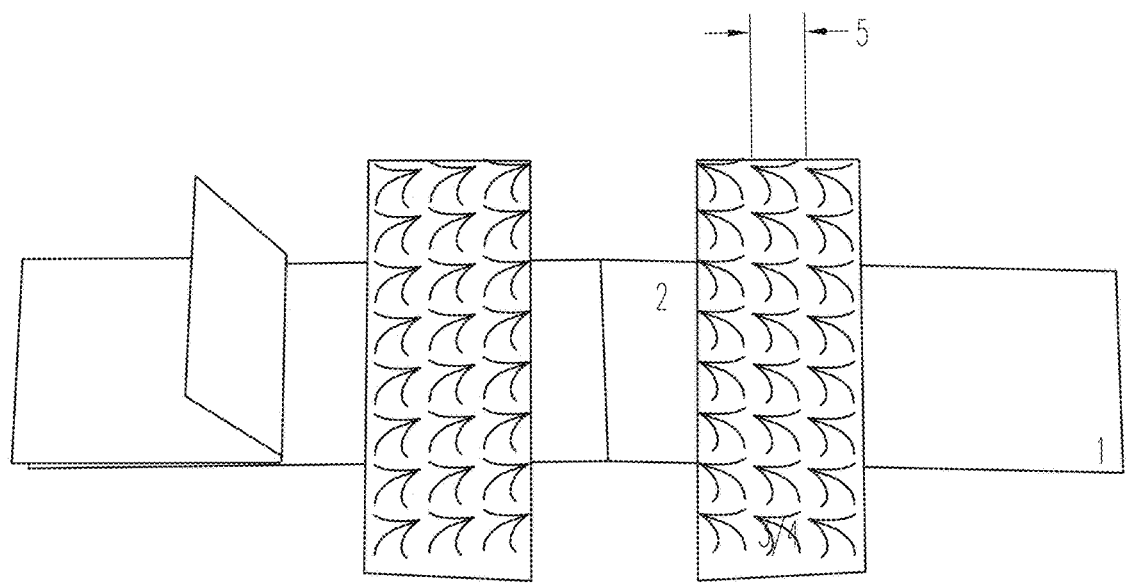

These devices all comprised two microstructure arrays which were manufactured according to the method described in Example 1; wherein two bases, each comprising a single microstructure array were affixed to single polyester filament backing derived from a single Steri-Strip S material. The bases are positioned with varying lengths of separation to create a variety of isthmus lengths. FIG. 17b shows a picture of one of these prototypes. In this picture, two microblade arrays were affixed on a polyester filament that is 22 mm in length with a 5 mm isthmus separation.

Each arrays is 11 mm wide×4.5 mm long, comprising 900 µm long PMMA microblades in a configuration of 8 angled microblades×3 angled microblades that were uniformly distributed throughout the array. The two arrays are separated by 5 mm. The tabs on either end of the device comprise an acrylate adhesive (present on the Steri-Strip S). During production of this prototype, many other models were made, varying different components such as, e.g., the isthmus length (i.e., distance between microstructure arrays); the length of tabs on opposing sides behind the arrays; the presence or absence of adhesive on the tabs and/or on the isthmus areas; types of microstructures, size of microstructure arrays used, and density of microstructures.

Prototype C.

Figure 17C:
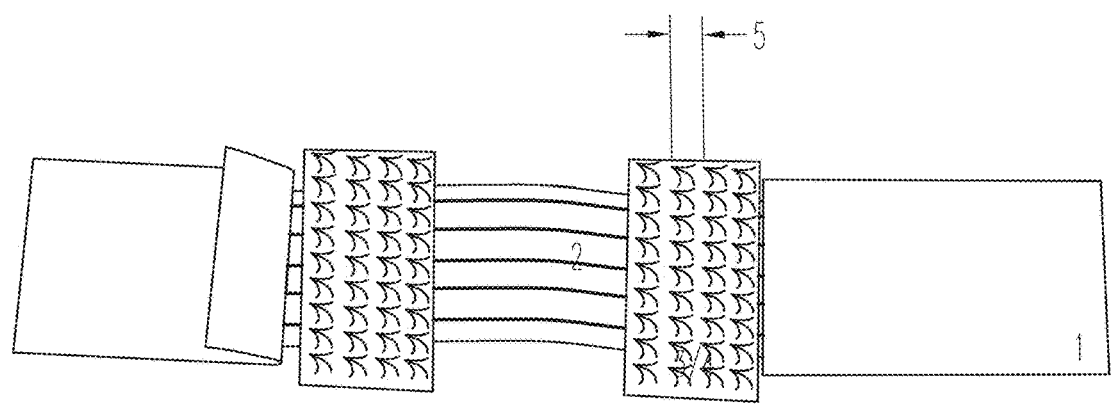
Figure 18A:
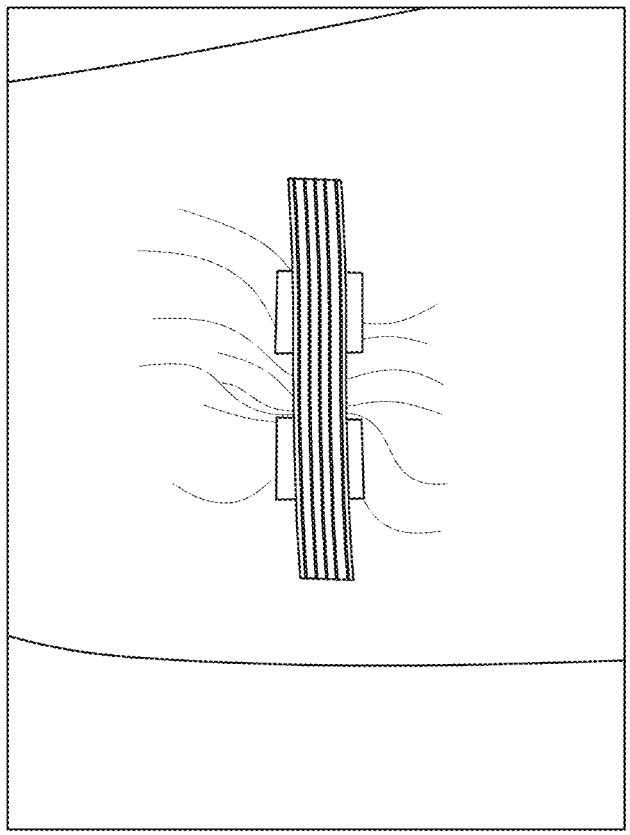
FIGS. 18a and 18b are photographs of the devices shown in FIG. 17c, when applied on a human volunteer, both with and without a protective cover. These devices comprise PMMA microneedles affixed to a Steri-Strip adhesive tape. Note the wrinkling of the skin in the middle of the device demonstrating the ability of the device to successfully stretch the skin documenting the device's ability to apply lateral tension on the skin, which is important for closing a wound. This indicates the device is capable of closing a wound.
Figure 18B:
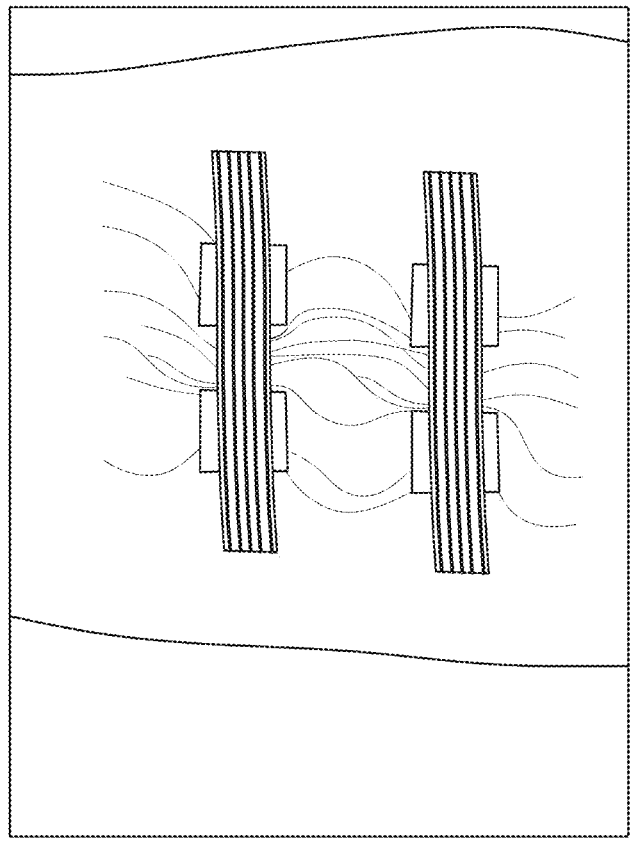
Figure 19:
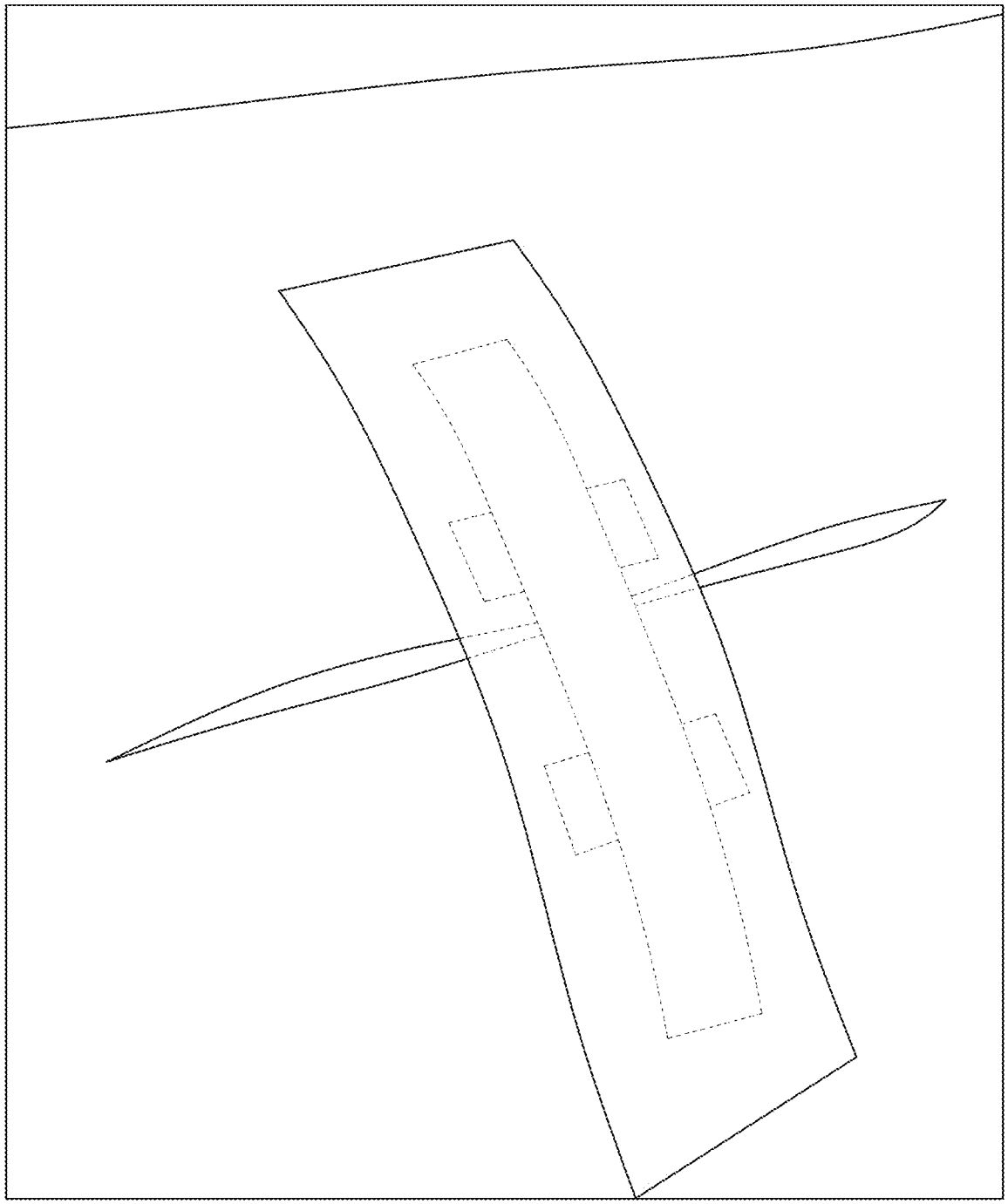
FIG. 19 is a photograph of one non-limiting example of the present wound closure devices. In this embodiment, the device comprised two PMMA microneedle arrays on PMMA bases that were glued onto an inelastic backing of polyethylene derived from Steri-Strip S. The photograph shows the device as applied on a silicone skin simulator with an incision made in it, and placed under tension, additionally with an adhesive cover.
Figure 20:
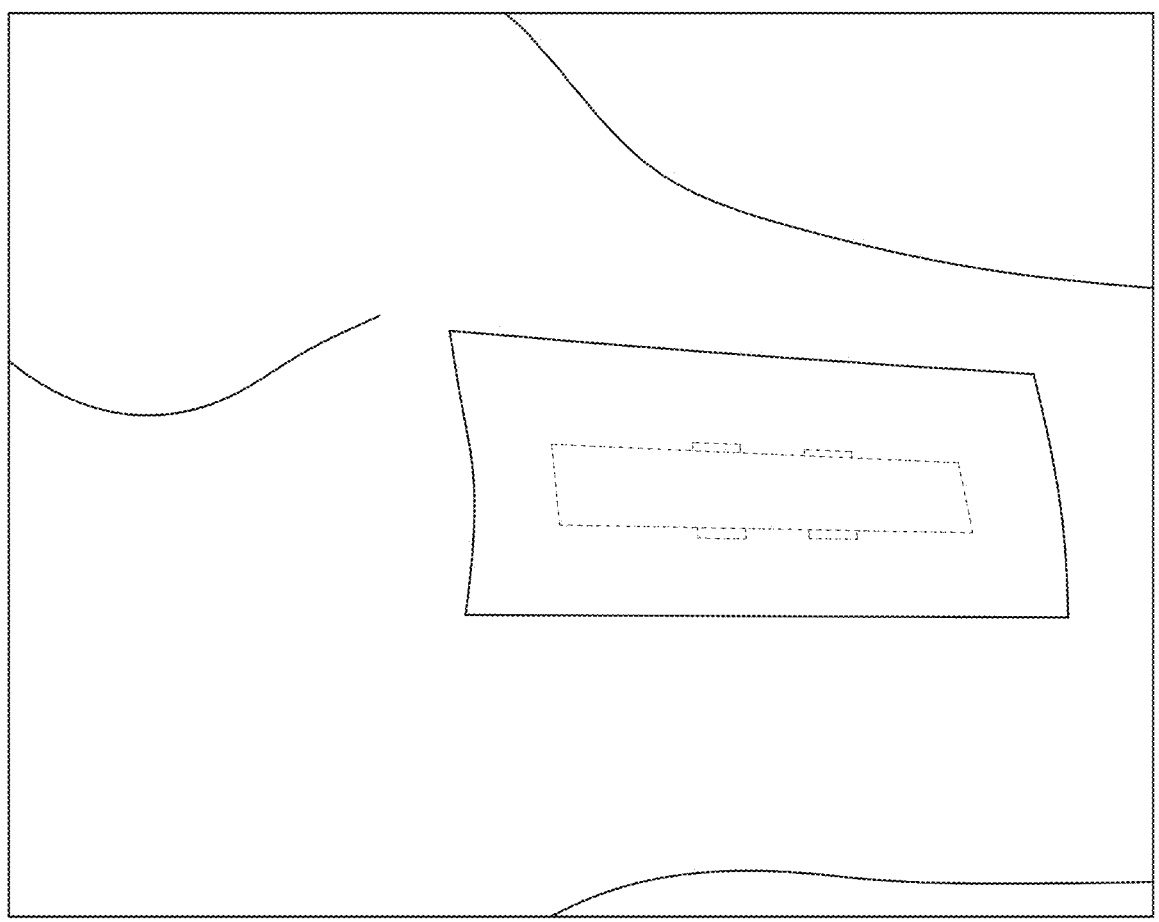
FIG. 20 is a photograph of a device, as described in FIG. 19, placed on the wrist of a human volunteer and protected by an adhesive cover.

These devices all comprised two microstructure arrays which were manufactured according to the method described in Example 1; wherein two bases, each comprising a single microstructure array were affixed to single backing made of paper/fiber mixture with added polyester filament supports for strength (This backing has some flexibility to allow it to conform to the skin, while still allowing the wound to be closed) which was derived from Steri-Strip (Note: Not Steri-Strip S) material. The bases are positioned with varying lengths of separation to create a variety of isthmus lengths. FIG. 17c shows a picture of one of these prototypes. In this picture, two microneedle arrays were affixed on a 45 mm polyester filament with a 8 mm isthmus separation. Each array is 10 mm wide×6 mm long, comprising 1 mm long PMMA needles in a configuration of 7 straight needles×4 straight needles that were uniformly distributed throughout the array. The tabs on either end of the device comprise an acrylate adhesive (contained on the Steri-Strips). The two microneedle arrays are separated by 8 mm. During production of this prototype, many other models were made, varying different components such as, e.g., the isthmus length (i.e., distance between needle arrays); the length of tabs on opposing sides behind the needle arrays; the presence or absence of adhesive on the tabs and/or on the isthmus areas; types of microstructures, size of microstructure arrays used, and density of microstructures.

Summary

In this example, the versatility of the present wound closure devices was demonstrated. As shown, it is possible to vary the dimensions (e.g., size, shape, width, and length) of the microstructures and arrays; type (see FIGS. 7a and 7b, and FIGS. 12a, and 12b, which show microneedle and microblade arrays, respectively); and angles of the microstructures which are provided upon bases of various lengths and widths. It is also possible to fashion microstructure arrays of variant size; shape; and microstructure density. It is also possible to fashion wound closure devices comprising a variety of backings/isthmus sizes; materials; array configurations, etc. Accordingly, the present wound closure devices of the present invention provide a highly versatile wound closure system which can provide a myriad of wound closure devices capable of being fine tuned to the specific requirements necessary for closing a broad spectrum of different types of wounds in a variety of different tissues and skin.

Example 3

Microstructure Array Traction Analysis

The following example outlines a preliminary analysis we performed to determine if the microstructure arrays were capable of gripping and holding skin. The aim of this study was to:

To assess whether wound closure devices comprising angled microblades could adhere to skin.

A 15 mm×28 mm segment of Steri-Strip S with 8 mm×12 mm array of C2 microblades (8×4 microblades uniformly distributed, See FIG. 2b) was attached to a 2.5×2.5 cm piece of fresh porcine skin (2-3 mm thick). The porcine skin was previously glued onto a Plexiglass slide, rinsed with 0.9 wt % saline solution, and patted dry with gauze prior to testing. Traction was measured with a tensile tester by mounting the needle on one side of the tester (Shimadzu AGS-X) and the skin on the other and then applying a pulling force.

Results

Figure 21:
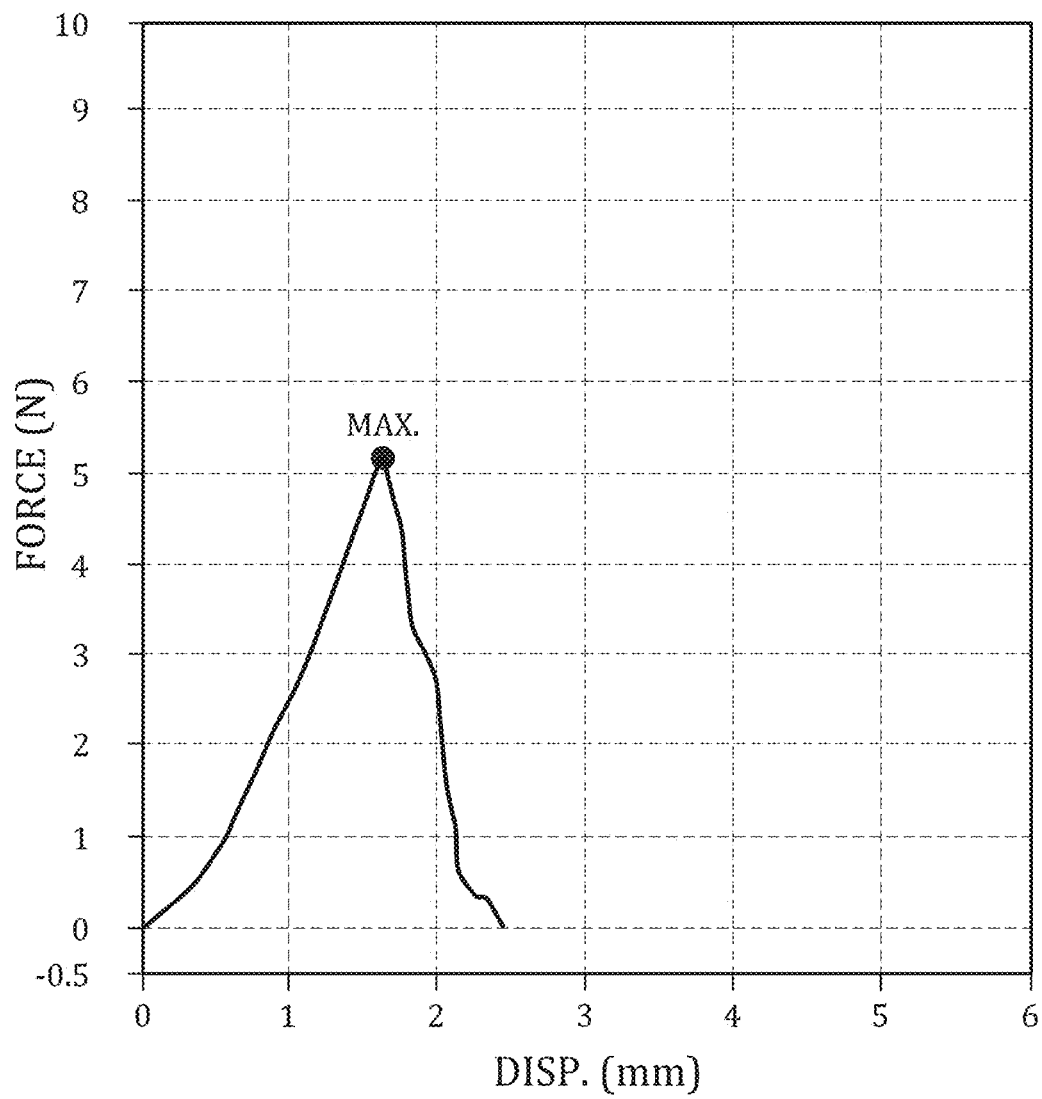
FIG. 21 shows data from an experiment testing the traction of angled needles applied on fresh porcine skin. A 15 mm×28 mm segment of Steri-Strip S with 8 mm×12 mm array of C2 needles (8×4 needles of the type illustrated in FIG. 2b) was pulled against a 2.5×2.5 cm piece of porcine skin glued onto a Plexiglass slide. Porcine skin was rinsed with 0.9 wt % saline solution, cut to 2-3 mm thick, and then glued to a microscopic slide. Porcine skin was rinsed again with saline solution and patted dry with gauze prior to testing. Traction was measured with a tensile tester by mounting the needle array on one side of the tester and the skin on the other. The Y axis of the graph is force measured in Newtons, and the X axis is displacement measured in millimeters.

The results of this experiment are shown in FIG. 21. The Y axis of the graph is force measured in Newton, and the X axis is displacement measured in millimeters. The angled needles were able to efficiently grip the porcine skin, indicating such a device will be able to close a wound, as intended.

Example 4

Preliminary Human Study

The following example outlines a preliminary human study that was performed to compare three different wound closure devices of the present invention. The aims of this study were as follows:

To assess whether application of the devices induces pain

To test adherence of the devices to human skin

To monitor inflammatory responses induced by the devices

The wound closure devices were placed on the volar surfaces of the forearms of 3 healthy human volunteers, and discomfort/pain, inflammatory responses and the stability of the device placement were observed on a daily basis for up to 8 days. The devices were affixed to the skin (with no wound) by pressing down on one of the arrays and then pulling in a lateral direction to stretch the skin and then affixing the other array to the skin so that the skin in between the two arrays is compressed together to simulate the procedure that would be used to close a wound.

Wound Closure Devices

The wound closure devices used in this study all comprised microneedles and bases that were made out of PMMA. Base thickness was approximately 140 µm. Each wound closure device contained two microstructure arrays, which were approximately 1 cm×1 cm in dimensions. Devices A and B comprised microneedles, while Device C comprised microblades. The devices each comprised a backing made out of Steri-Strip S® material, which was attached to the arrays with an 8 mm long isthmus separating the two arrays. Additionally, the Steri-Strip-S® material extended 6 mm beyond the distal end of each array. The Steri Strip-S® material normally contains adhesive; however, the adhesive was covered up prior to application onto the skin of the volunteers so that the devices could be tested for adherence without adhesive. Also, after application to the skin, the devices and adjacent skin were covered with an adhesive polyurethane tape cover (3M 9833) that was approximately 4 cm×4 cm. The following devices were tested.

Device A

Each microneedle in the array was in the shape of a pyramid and was at a 90 degree angle to the base of the array.

Each microneedle had the following dimensions: 1 mm length, 420 microns width at the foundation, and 60 micron tip diameter.

The microneedles were uniformly distributed at a pitch of 1.5 mm, and there were a total of approximately 50 microneedles in each array.

Device B

Each microneedle in the array was in the shape of a pyramid and was at a 90 degree angle to the base of the array.

Each microneedle had the following dimensions: 1 mm length, 420 microns width at the foundation, 60 micron tip diameter.

Arrays on opposing sides of the wound were positioned such that the angled microneedles were angled towards the wound.

The microneedles were uniformly distributed at a pitch of 3 mm, and there were a total of 16 microneedles in each array.

Device C

Each microblade in the array was in the shape of a pyramid and was at a 51 degree angle to the base of the array.

Each microblade had the following dimensions: 900 micron length, 1050 micron width at the foundation, approximately 130 micron tip width, approximately 20-30 micron tip thickness.

Arrays on opposing sides of the wound were positioned such that the angled microblades were angled towards the wound.

The microblades were uniformly distributed at a pitch of 4.5 mm, and there were a total of 9 microblades in each array.

Device Application

The wound closure devices were placed on the skin using the following procedure: The adhesive strip attached to the distal end of one of the arrays was pressed down upon by hand, to enable attachment to the skin. Pressure was then applied over the closest array using the thumb. While the thumb remained press down on the first array, the distal end of the other array was pinched between 2 fingers and gently stretched laterally to simulate closure and eversion of the wound. After placement of the device, the device was covered with a medical adhesive cover (catalog no. 9833, 3M).

Results

Volunteers reported mild pain upon application of the devices (approximately 1-2 on a visual analog score (VAS) of pain ranging from 0 to 10). Pain disappeared within an hour and then the devices were painless for the duration of their application to the skin (2-8 days).

The wound closure devices remained on the skin for a range of 2 to 8 days. Observations were made on a daily basis. All devices remained in place and appeared to be firmly attached to the skin for the entire period of application. For Device A, erythema appeared in the skin in contact with the array approximately 3 days after placement of the device. When the array was removed swelling (edema) was also observed. The skin returned to normal appearance after approximately 2-4 weeks. For the other devices, there was no evidence of erythema, edema or inflammation at the skin sites where these devices remained in place for up to 8 days. Small puncture wounds were noted where the needles entered the skin which disappeared after 24-48 hours at which point the skin returned to normal appearance for Devices B and C.

Summary

In summary, the results of the present study showed that the devices can be applied with little induction of pain. All of the devices remained firmly attached to the skin for several days. Devices with more pitch (3 mm or more) did not result in skin inflammation (erythema and edema), while the device with a pitch of 1.5 mm did show evidence of inflammation. Therefore, without being limited by theory, it appears from this preliminary study, that reducing the density and number of the microstructures in the array may result in less inflammation, without compromising the ability of the device to remain attached to the skin. These and other data (e.g., Example 5) strongly support that the present wound closure devices provide an attractive alternative to the prior art methods of wound closure.

Example 5

Porcine Wound Closure Study

Figure 22A:
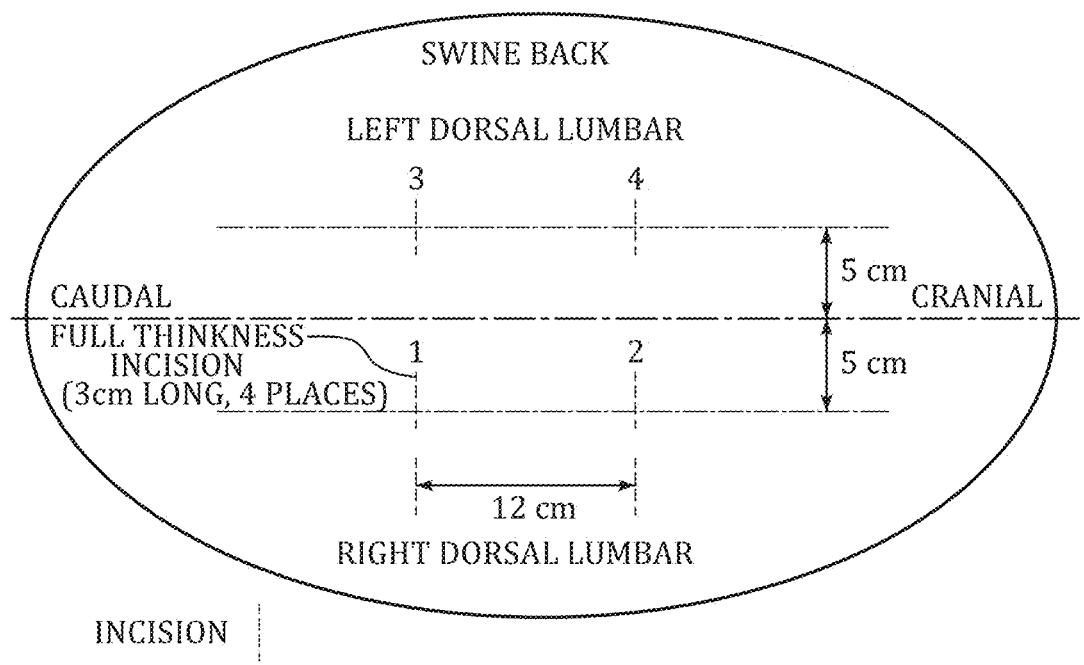
FIGS. 22a to 22c illustrate the location of wounds, which were created on a neonatal porcine for use in a pre-clinical study of the wound closing efficiency of the devices of the present invention. This study is fully described in Example 4.
Figure 22H:
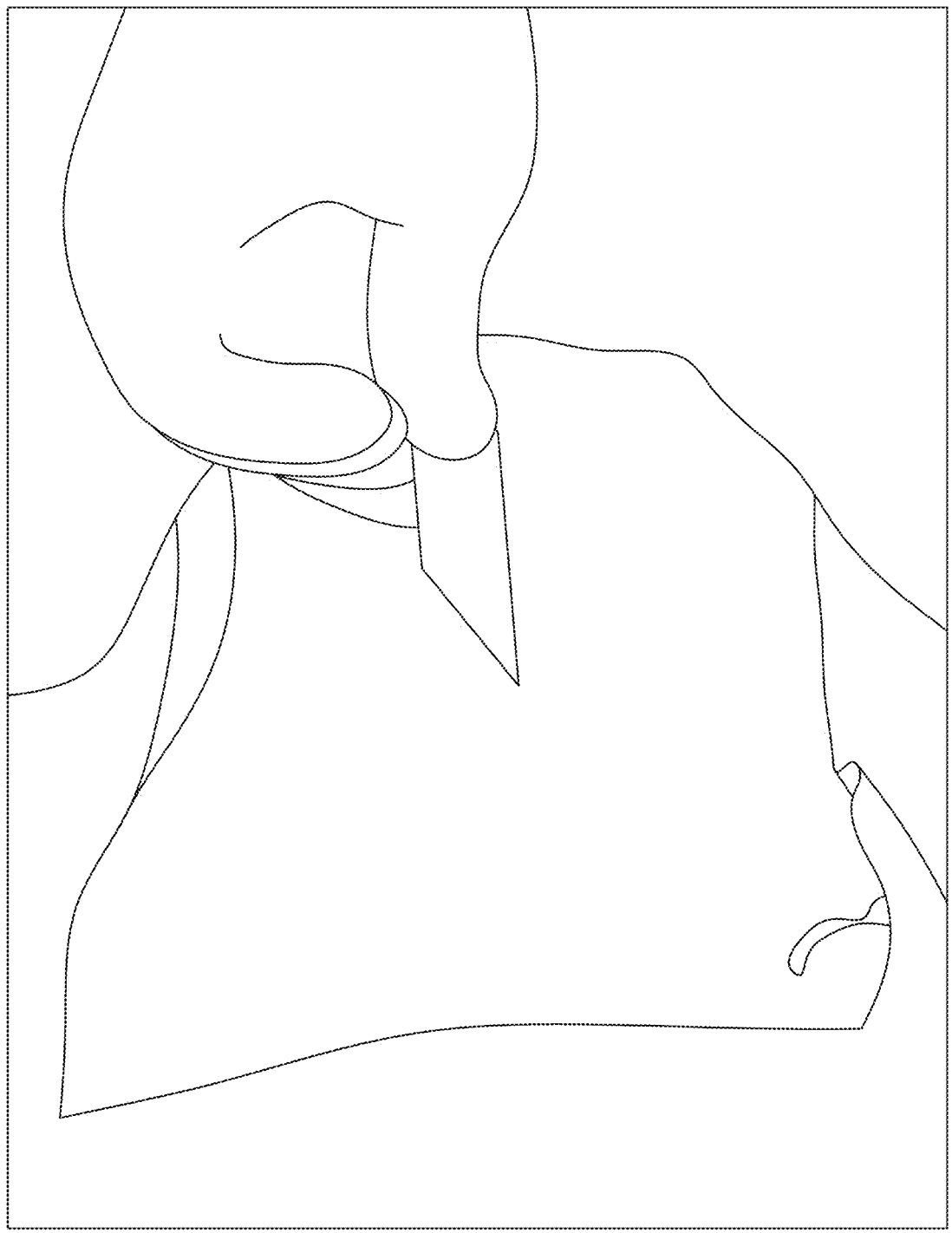
Figure 22A:
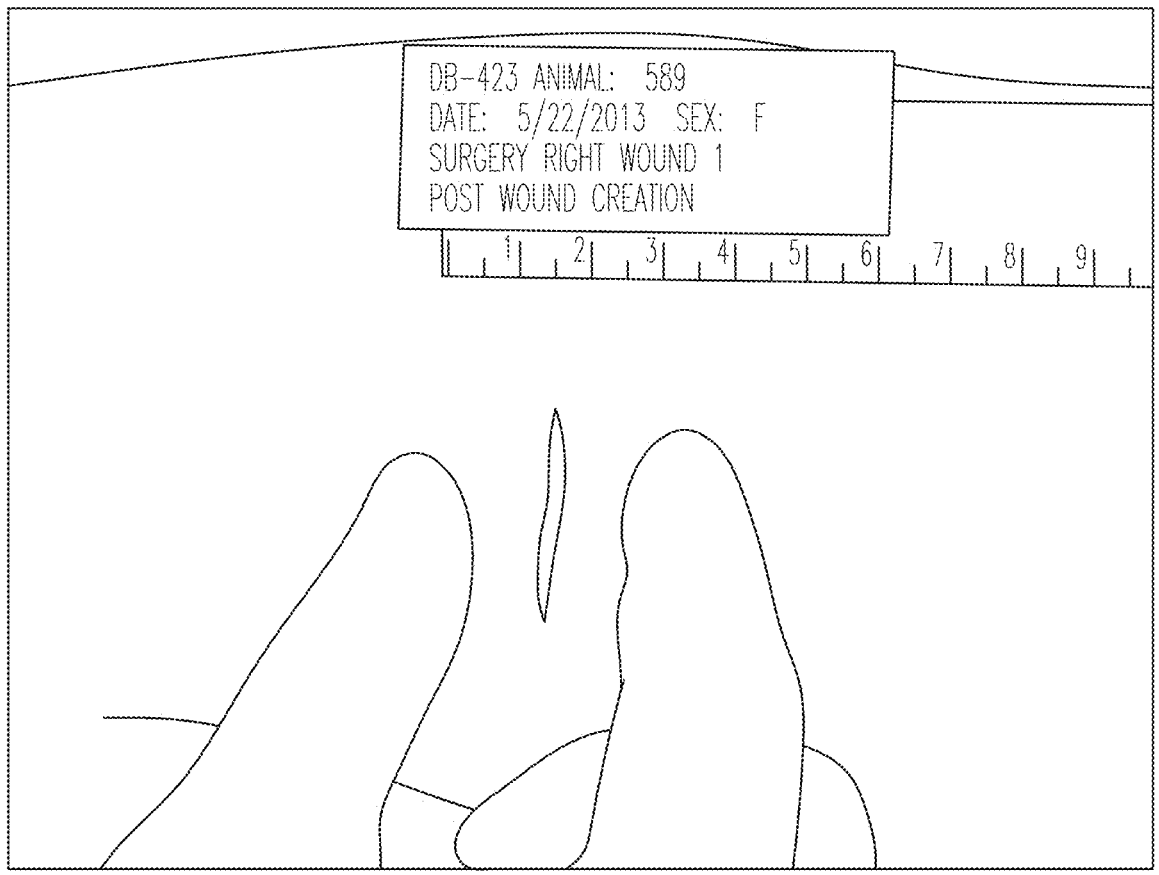
Figure 24:
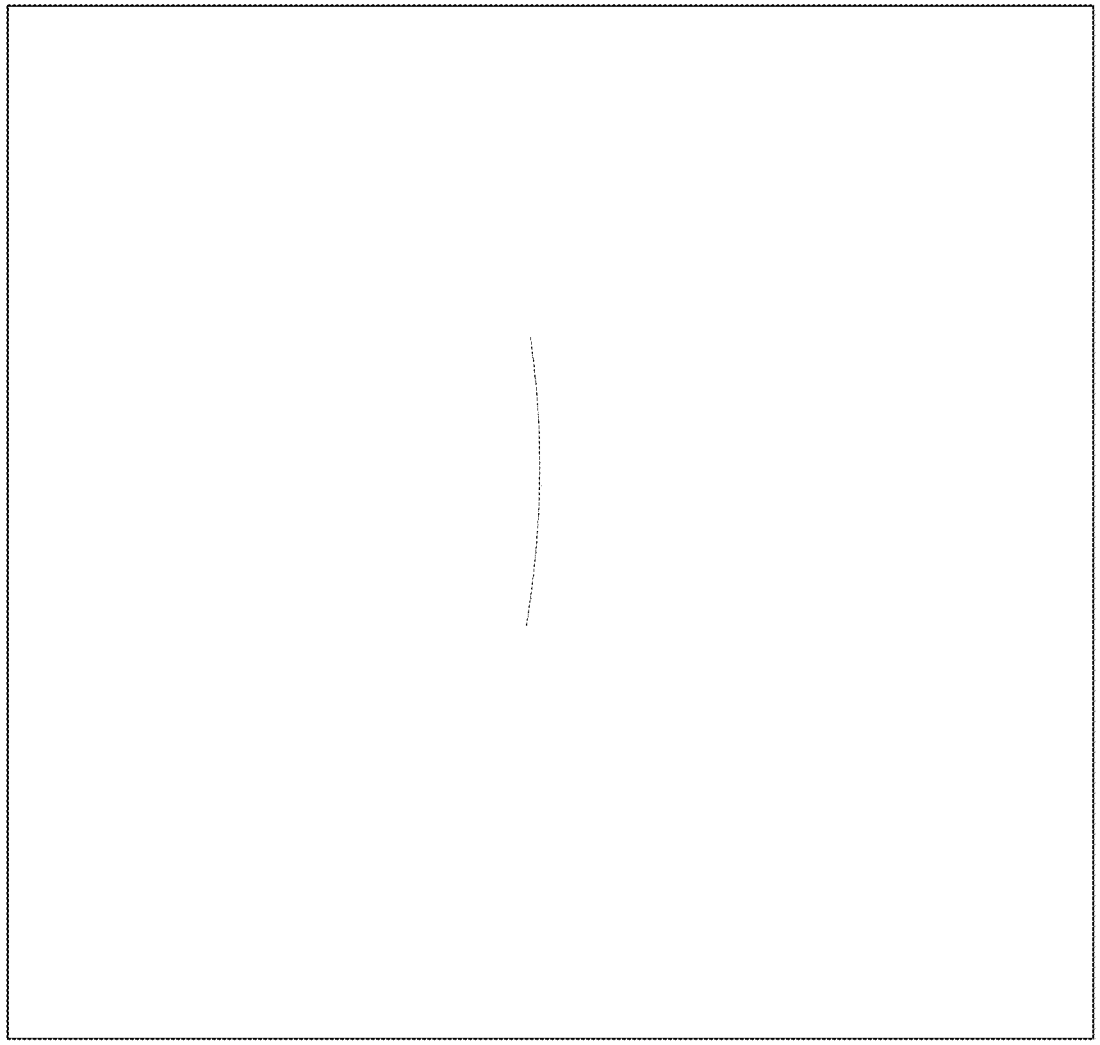
FIG. 24 is an image from Day 9 of the undressed (device and cover removed) wound that was treated with Device A, which comprised two straight-needle microstructure arrays.
Figure 25:
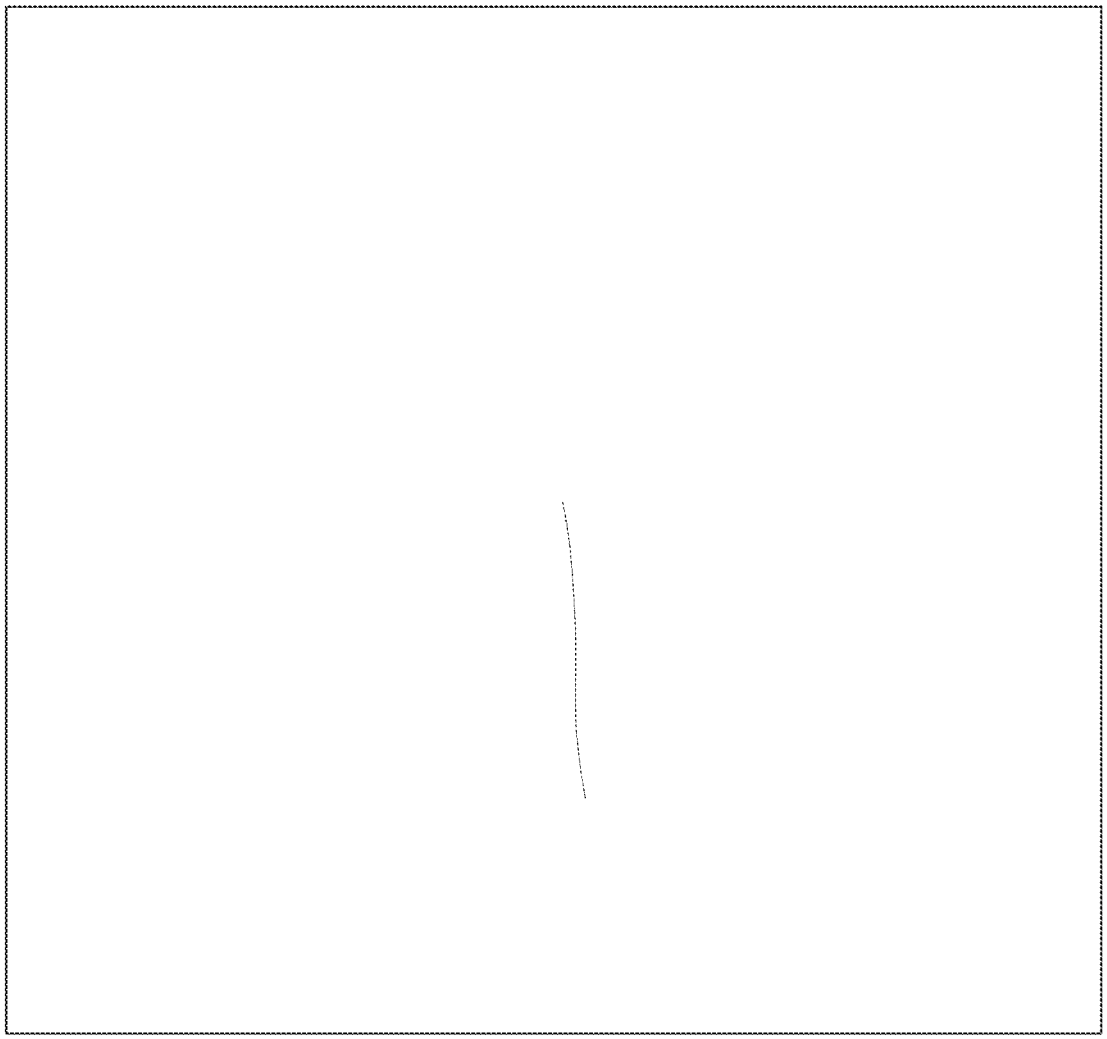
FIG. 25 is an image from Day 9 of the undressed wound that was treated with Device C, which comprised two angled needle microstructure arrays.
Figure 26:
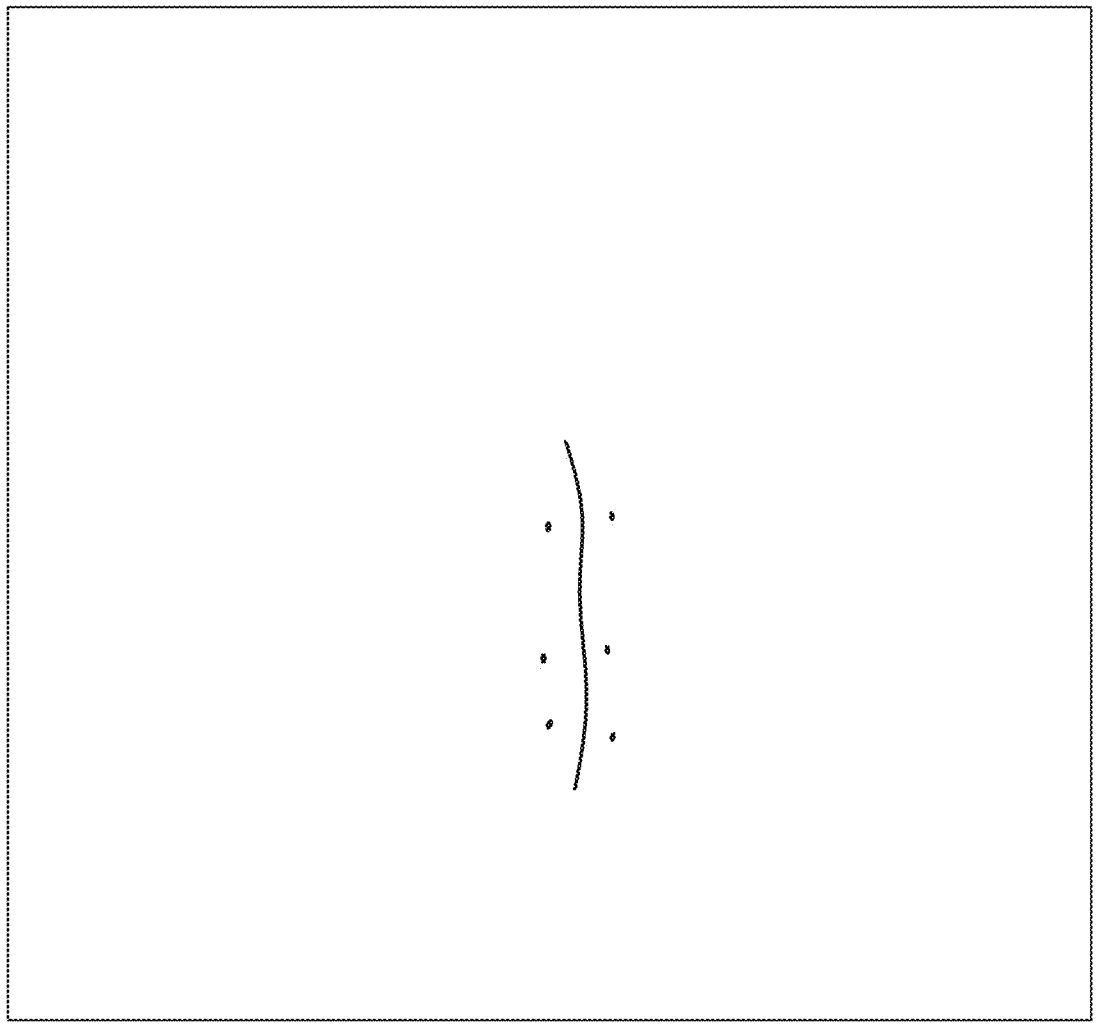
FIG. 26 is an image from Day 9 of the undressed wound that was treated by suturing.

The following example outlines a preliminary animal study that was performed to assess the wound closing efficiency of three different wound closure devices of the present invention; and to compare these efficiencies with wound closing efficiency of sutures. The aims of this study were as follows:

To test adherence of the devices to wounded skin
To assess the devices ability to close a wound
To monitor inflammatory responses induced by the devices
To assess the ability of the devices to promote healing
To compare the results above between the devices and sutures used to close wounds Procedure of the Study A neonatal porcine was used for the present study (note: neonatal porcine skin closely approximates the biomechanical properties of human skin), and is a standard animal model for testing wound closure devices. Using a scalpel, full thickness wounds, each of 3 cm in length, were made in the skin on the dorsum of the thoracic area of the animal under general anesthesia. Wounds were made on each side of the center of the posterior of the animal; and wounds on the same side were approximately 5 cm from one another (FIGS. 22a and 22b).

The wound area was shaved, and then cleaned with a standard antiseptic solution. Using aseptic technique, a 3 cm full thickness incision was made with the scalpel (FIG. 22c). The wound was blotted dry with sterile gauze and then the wound was closed with the wound closure devices (FIG. 23). Each wound was then closed with a different type of wound closure device, with two identical devices being applied to each wound. Additionally, as a control, one of the wounds was closed with sutures in a similar manner, wherein three sutures were applied to the wound (FIG. 23).

Wound Closure Devices

The wound closure devices used in this study all comprised microstructures and bases that were made out of PMMA according to the method described in Example 1. Base thickness was approximately 140 µm. Each wound closure device contained two microstructure arrays, which were approximately 6 mm×10 mm in dimensions. The devices each comprised a backing made out of Steri-Strip® material, which was attached to the arrays with an 8 mm long isthmus separating the two arrays. Additionally, the Steri-Strip® material extended 6 mm beyond the distal end of each array. The following devices were tested.

Device A: Straight Microneedles (i.e., 90° Angle)

Each microneedle in the array was in the shape of a pyramid and was at a 90 degree angle to the base of the array.

Each microneedle had the following dimensions: 1 mm length, 420 microns width at the foundation, and an approximate 60 micron tip diameter The microneedles were uniformly distributed at a pitch of 3 mm, and there were a total of 12 microneedles in each array.

Figure 7A:
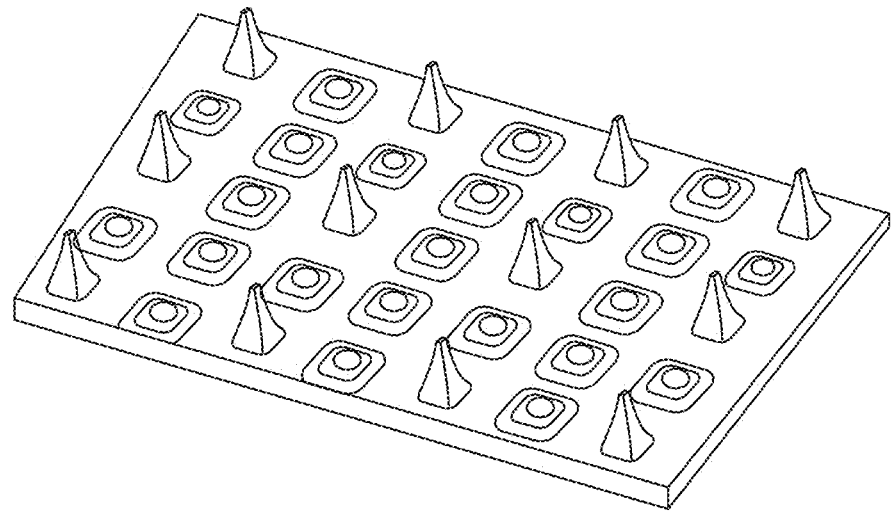
FIGS. 7a and 7b show a comparison of (FIG. 7a) a low density straight microneedle array comprising 12 needles of 1 mm height in a 3 mm pitch formation in a 7 mm×10 mm array and (FIG. 7b) a high density straight microneedle array comprising 28 needles of a 1 mm height with a uniform pitch of 1.5 mm in a 6 mm×10 mm array.
Figure 7B:
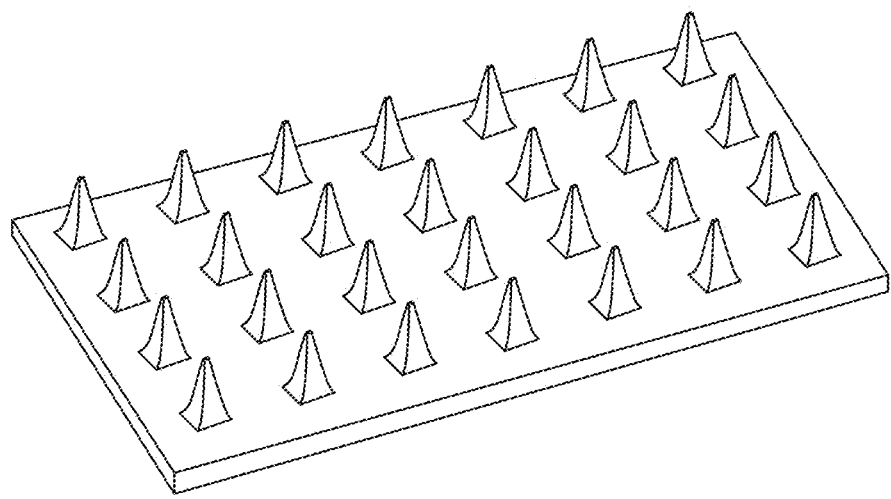
Figure 9A:
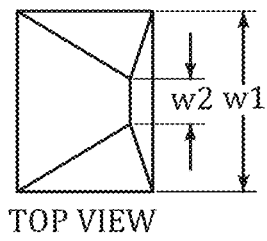
FIGS. 9a to 9d schematically illustrate a microblade of type 1 MB (one of the examples from FIG. 8b).
Figure 9B:
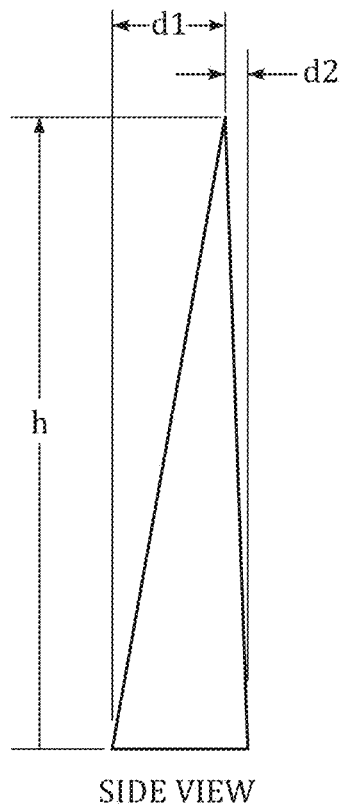
Figure 9C:
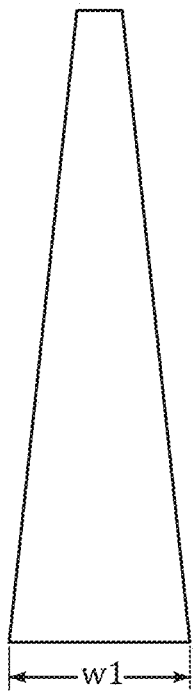
Figure 9D:
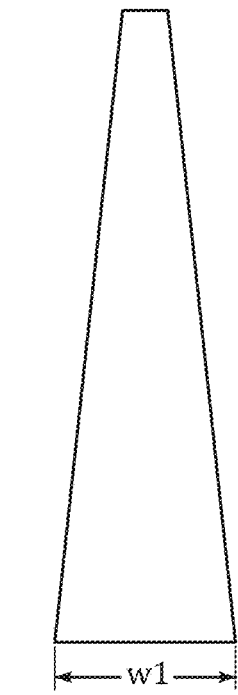
Figure 11A:
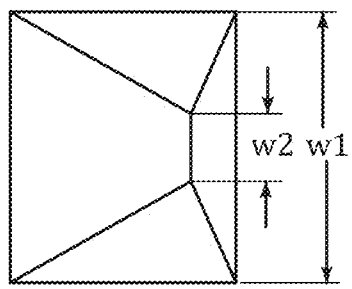
FIGS. 11a to 11d schematically illustrate a microblade of type 3 MB (one of the examples from FIG. 8b).
Figure 11B:
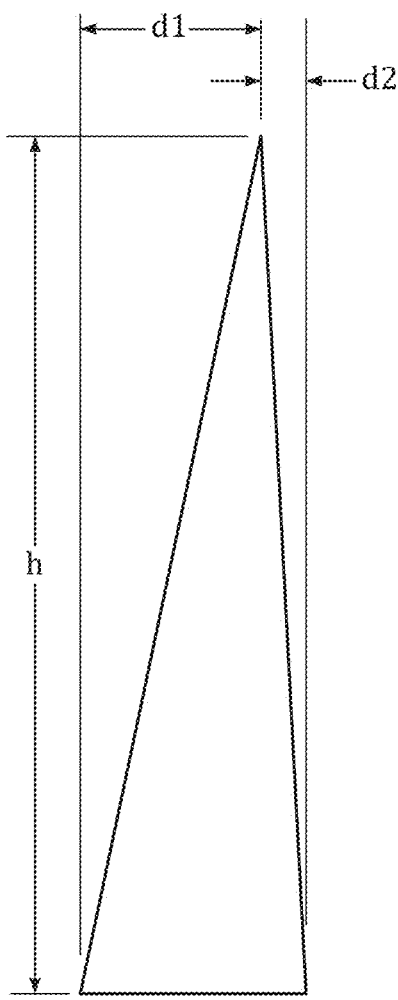
Figure 11C:
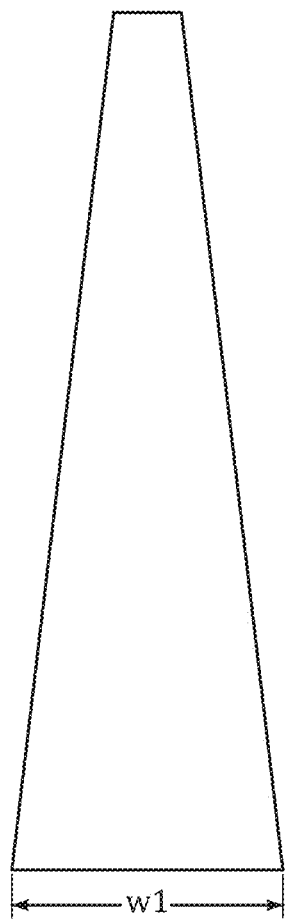
Figure 11D:
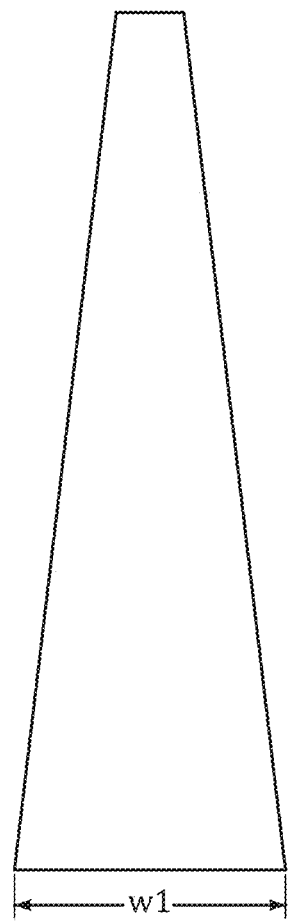

FIG. 7a shows a photograph of one of these arrays.

Device B: Angled Microblades (i.e., 51° Angle)

Each microblade in the array was in the shape of a pyramid and was at a 51 degree angle to the base of the array.

Each microblade had the following dimensions: 900 micron length, 900 micron width where the microblade meets the foundation, approximately a 130 micron tip width, and approximately 20-30 micron tip thickness.

The microblades were uniformly distributed at a pitch of 4.5 mm, and there were a total of 6 microblades in each array.

Arrays on opposing sides of the wound were positioned such that the angled microblades were angled towards the wound.

Figure 12A:
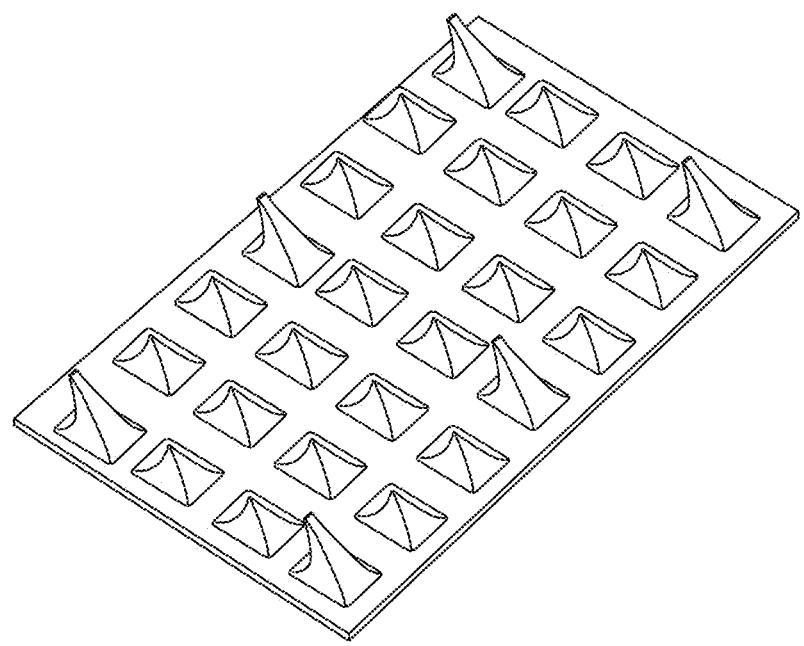
FIGS. 12a and 12b show a comparison of (FIG. 12a) a low density angled microblade array comprising 6 needles that are 900 µm in height in a 4.5 mm pitch formation in a 6 mm×10 mm array and (FIG. 12b) a high density angled microblade array 900 µm in height with a uniform pitch of 1.5 mm.
Figure 12B:
Figure 13B:
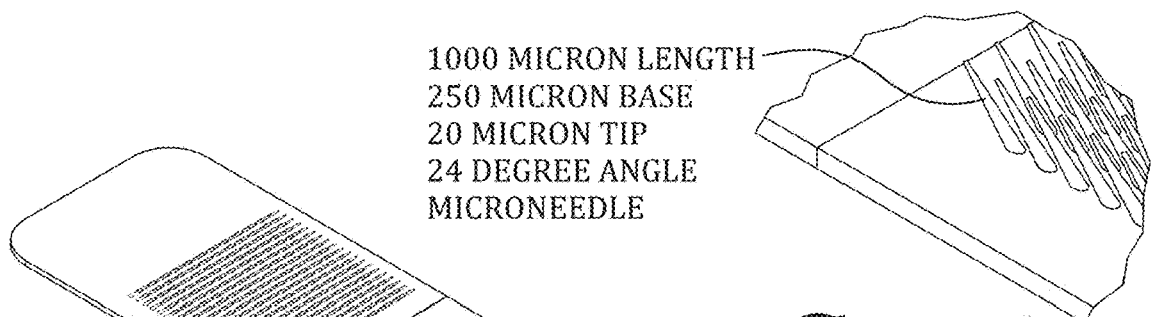
FIGS. 13a to 13e show schematic drawings of an exemplary wound closure device with angled needles made with a silicone backing and high-density needle arrays. Note the optional addition of a microstructure coating (e.g., a coating with a wound healing agent).
Figure 13A:
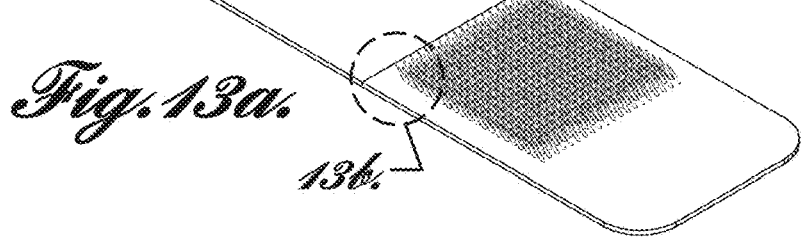
Figure 13C:
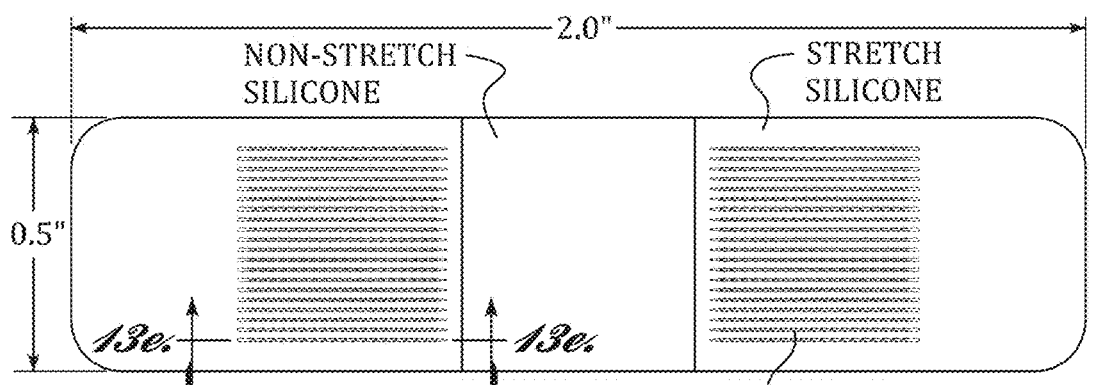
Figure 13D:
Figure 13E:
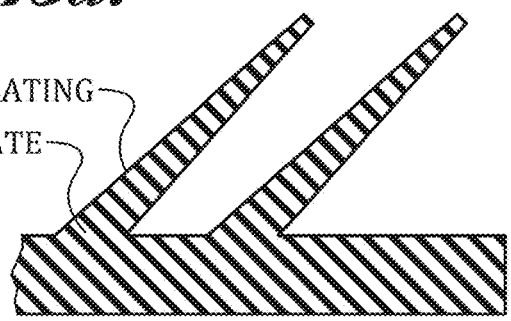
Figure 14A:
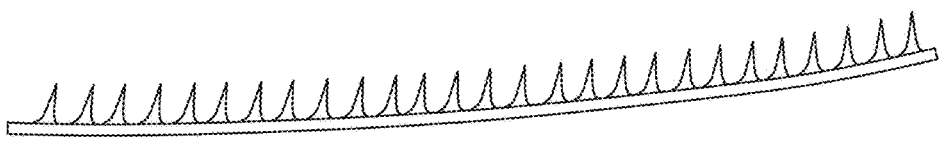
FIGS. 14a to 14c are images of an exemplary wound closure device comprising a PMMA microstructure array of straight microneedles mounted on a silicone backing.
Figure 14B:
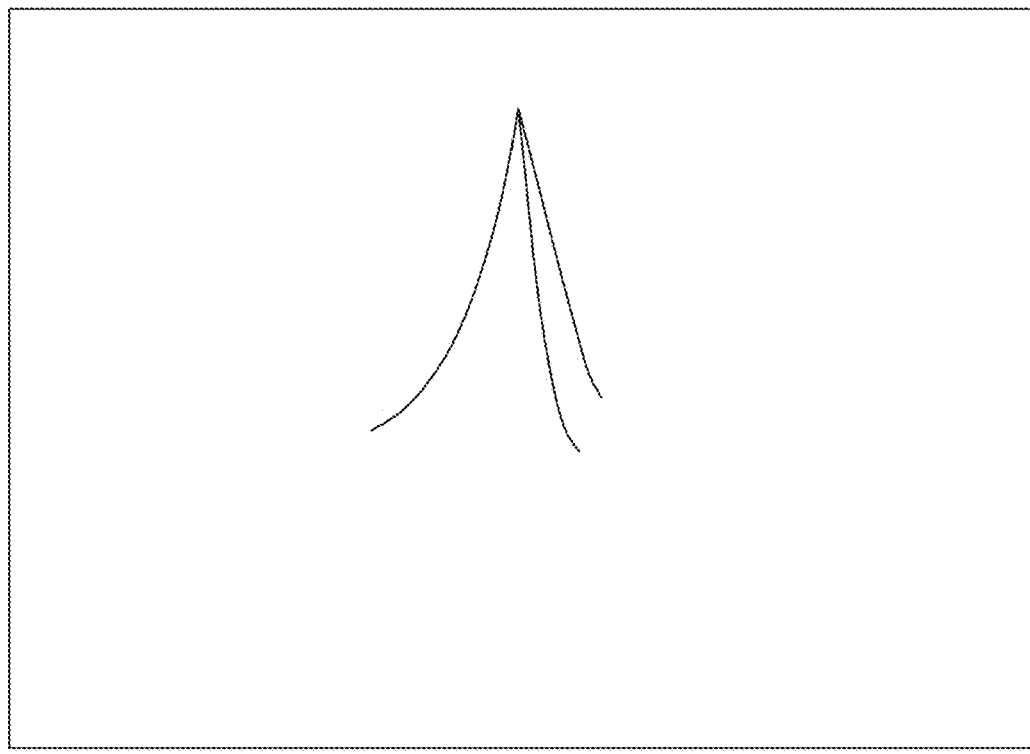
Figure 14C:
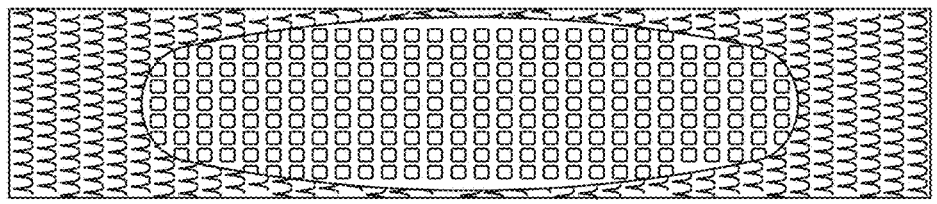

FIG. 12a shows a photograph of one of these arrays.

Device Application

On Day 0, the wound closure devices were placed on the skin of the porcine using the following procedure: the adhesive strip attached to the distal end of one of the arrays was pressed down upon using the fingers of one hand, to enable attachment to the skin. Pressure was then applied over the closest array using the thumb. While the thumb remained press down on the first array, the distal end of the other array was pinched between two fingers and gently stretched laterally to enable closure of the wound and enable eversion of the wound. This same process was repeated in placing the second wound closure device. After placement of the two wound closure devices, the wound area was covered with Tegaderm®.

Results

The wounds were observed daily for 12 days, with scoring for inflammation, infection, dehiscence, erythema, and edema. Furthermore, photos were taken to document the healing process. On Day 9, the devices/sutures were removed. Pictures showing the wounds on Day 1 (one day after placement of devices/sutures), Day 6, and Day 9 (10 days after placement of devices/sutures) are presented in FIGS. 23-26, and a brief summary of the results is presented below.

Inflammation

On Day 1, inflammation was observed around the wounds that were closed with device B and with sutures, however no such inflammation was induced by wound closure device A. On Day 6, the sutured wound was still inflamed, but no such inflammation was observed around the wounds closed with devices A and B. On Day 9, inflammation was still observed around the wound closed with sutures, however no inflammation was observed around the wounds closed with device A or B.

Infection

No infections were observed on any of the wounds on Day 1, Day 6, or Day 9, regardless of the wound closure method.

Dehiscence

No dehiscence was observed on any of the wounds on Day 1, Day 6, or Day 9, regardless of the wound closure method.

Erythema

Erythema was observed around the sutured wound on Day 1, Day 6, and Day 9, with the Day 9 erythema having a Draize Score of 2, according to the Draize scale of 0-4. On Day 1, but not Days 6 or 9, erythema was also observed around the wound that was closed with device B. Device A did not induce erythema.

Edema

No edema was observed on any of the wounds on Day 1, Day 6, or Day 9, regardless of the wound closure method.

Summary

In summary, the results of the present study showed that devices A and B can both effectively close a wound, with comparable efficiency to that of sutures. Additionally, the wound closure devices disclosed herein provided the added benefit of not inducing lasting inflammation or erythema, wherein both of these adverse reactions were induced and remained for the 10 day observation period in the wound closed by suturing. Thus the devices of the present invention provide an attractive alternative to sutures, for wound closure.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A wound closure device comprising a backing having a longitudinal axis, flexible portions of the backing attached to two or more microstructure arrays, each microstructure array comprising at least two microstructures wherein the two or more microstructure arrays are separated by a non-stretchable isthmus forming a non-stretchable portion of the backing such that the flexible portions of the backing supporting the two or more microstructure arrays and the non-stretchable portion of the backing forming the non-stretchable isthmus are co-planar and such that the non-stretchable isthmus has a width transverse to the longitudinal axis, the width narrower than the two or more microstructure arrays such that the wound closure device is configured to form a gap between the non-stretchable isthmus and an adjacent isthmus of an adjacent wound closure device when the wound closure device is positioned adjacent the adjacent wound closure device, and wherein the wound closure device is capable of being stretched laterally.

2. The wound closure device of claim 1, wherein the two or more microstructure arrays comprise only two microstructure arrays.

3. The wound closure device of claim 1, wherein the wound closure device is capable of maintaining a wound in a closed state.

4. The wound closure device of claim 1, wherein the two or more microstructure arrays are attached to the backing in a configuration such that at least one of the two or more microstructure arrays is capable of penetrating skin on one side of a wound, and another one of the two or more microstructure arrays is capable of penetrating the skin on another side of the wound.

5. The wound closure device of claim 1, wherein the backing comprises an adhesive.

6. The wound closure device of claim 5, wherein the adhesive is located on one or more removable tabs.

7. The wound closure device of claim 1, wherein the backing is in the form of a roll bandage.

8. The wound closure device of claim 1, wherein the at least two microstructures of each of the two or more microstructure arrays are at an angle of from 15-90 degrees relative to the backing.

9. The wound closure device of claim 1, wherein at least one microstructure of the at least two microstructures of each of the two or more microstructure arrays is curved.

10. The wound closure device of claim 1, wherein at least one microstructure of the at least two microstructures of each of the two or more microstructure arrays is straight.

11. The wound closure device of claim 1, wherein a length of the at least two microstructures of each of the two or more microstructure arrays is between 1 µm and 2 mm.

12. The wound closure device of claim 1, further comprising a protective cover configured to cover the wound closure device.

13. The wound closure device of claim 1, wherein the at least two microstructures of each of the two or more microstructure arrays comprise a material selected from a group consisting of silicone, chitin, polymethyl methacrylate (PMMA), metal, and a combination thereof.

14. The wound closure device of claim 13, wherein the metal is titanium or steel.

15. The wound closure device of claim 1, wherein the at least two microstructures of each of the two or more microstructure arrays are selected from the group consisting of microneedles, microblades, microanchors, microfishscale, micropillars, and microhairs.

16. The wound closure device of claim 1, wherein the at least two microstructures of each of the two or more microstructure arrays comprise a shape selected from a group consisting of a rod, cone, square, rectangle, pyramid, and cylinder.

17. The wound closure device of claim 1, wherein the backing is attached to first and second stretchable bases, each of the first and second stretchable bases comprising at least one of the at least two or more microstructure arrays, wherein the at least two microstructures of each of the two or more microstructure arrays extend from a respective one of the first and second stretchable bases, and wherein the first and second stretchable bases are separated by the non-stretchable isthmus.

18. The wound closure device of claim 1, wherein a first side of the backing configured to face away from a wound and that is opposite a second side including the two or more microstructure arrays is smooth and planar.

19. The wound closure device of claim 1, wherein:
the longitudinal axis defines a length of the wound closure device configured to extend across a wound; and
the width of the non-stretchable isthmus transverse to the longitudinal axis is shorter than the length and narrower than the two or more microstructure arrays.

20. A method of treating a wound, comprising attaching at least one wound closure device according to claim 1 to the wound, with or without first treating the wound with chitin and/or chitosan, wherein the method optionally further comprises covering the wound closure device with a cover after application of the wound closure device.

* * * * *